(12) United States Patent
Bennun-Serrano et al.

(10) Patent No.: US 12,163,122 B2
(45) Date of Patent: Dec. 10, 2024

(54) ASPARAGINE FEED STRATEGIES TO IMPROVE CELL CULTURE PERFORMANCE AND MITIGATE ASPARAGINE SEQUENCE VARIANTS

(71) Applicant: Regeneron Pharmaceuticals, Inc., Tarrytown, NY (US)

(72) Inventors: Sandra Bennun-Serrano, Briarcliff Manor, NY (US); Shawn M. Lawrence, Nyack, NY (US); Amy S. Johnson, Briarcliff Manor, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 256 days.

(21) Appl. No.: 17/458,929

(22) Filed: Aug. 27, 2021

(65) Prior Publication Data

US 2022/0064591 A1 Mar. 3, 2022

Related U.S. Application Data

(60) Provisional application No. 63/072,740, filed on Aug. 31, 2020, provisional application No. 63/072,745, filed on Aug. 31, 2020.

(51) Int. Cl.
*C12N 1/38* (2006.01)
*C12N 1/04* (2006.01)
*C12N 5/071* (2010.01)

(52) U.S. Cl.
CPC ............... *C12N 1/38* (2013.01); *C12N 1/04* (2013.01); *C12N 2500/32* (2013.01)

(58) Field of Classification Search
CPC ........ C12N 1/38; C12N 1/04; C12N 2500/32; C12N 2510/02; C12N 5/0682; C12P 21/02; C12P 13/20; C07K 16/00; C07K 2317/14
See application file for complete search history.

(56) References Cited

U.S. PATENT DOCUMENTS

| 10,526,631 B1 | 1/2020 | Solacroup et al. |
| 2013/0096283 A1 | 4/2013 | Khetan et al. |

FOREIGN PATENT DOCUMENTS

WO   2013/006479 A2   1/2013

OTHER PUBLICATIONS

Zhang et al., "Responses of CHO-DHFR cells to ratio of asparagine in feed media: cell growth, antibody production, metabolic waste, glutamate, and energy metabolism," Bioresour. Bioprocess. (2016) 3:5, 12 pages.

*Primary Examiner* — Satyendra K Singh
(74) *Attorney, Agent, or Firm* — Kramer Levin Naftalis & Frankel LLP

(57) ABSTRACT

A method for culturing eukaryotic cells for improved cell culture performance is provided. The method generally comprises propagating or maintaining eukaryotic cells in a defined cell culture medium; wherein the defined cell culture medium is supplemented with asparagine in an amount from about 2.6 mM to about 43.2 mM during early fed-batch cell culture and from about 2.6 mM to about 21.6 mM during late fed-batch cell culture; and maintaining said cells in said asparagine supplemented cell culture medium for at least a portion of the early fed-batch cell culture and at least a portion of the late fed-batch cell culture; wherein the performance of the cell culture is improved by the asparagine supplementation, as compared to a similar method with a lower amount of asparagine supplementation in the early and/or late fed-batch cell culture.

12 Claims, 44 Drawing Sheets

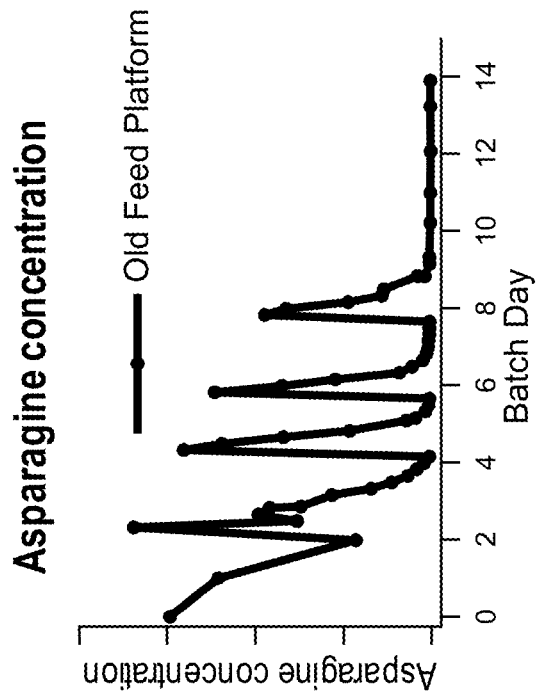
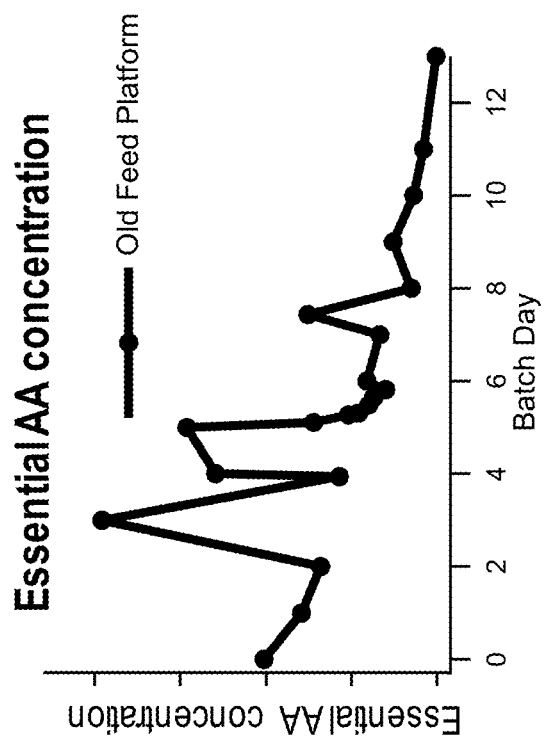
FIG. 1A
FIG. 1B

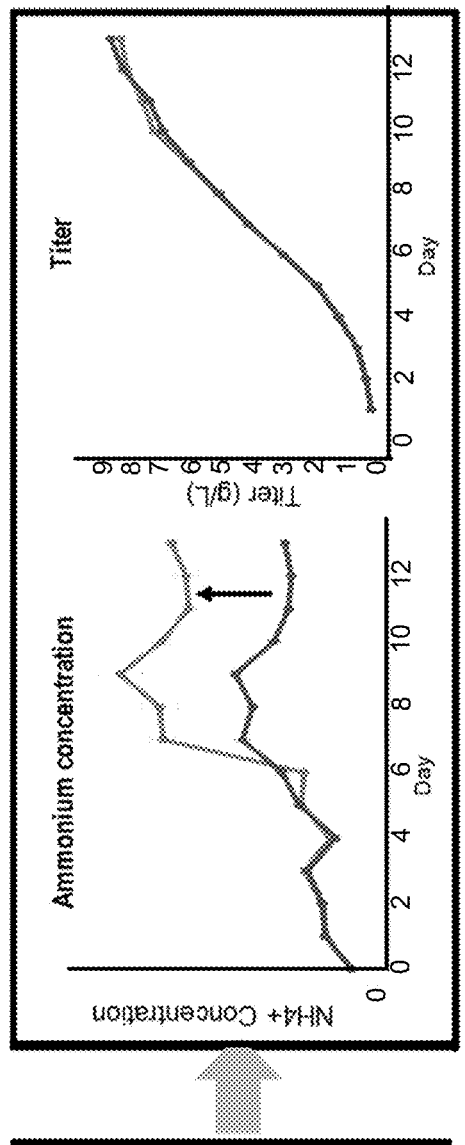
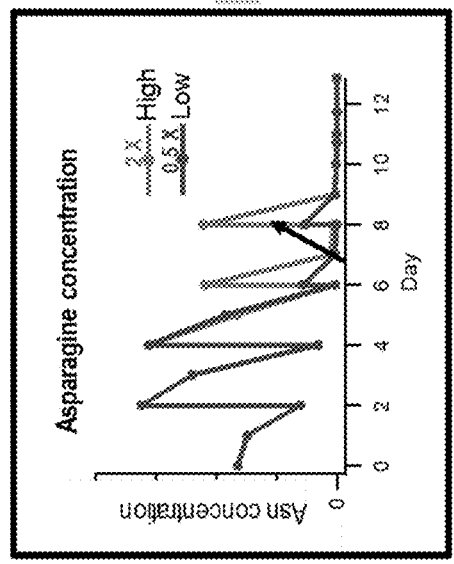
FIG. 4A  FIG. 4B  FIG. 4C

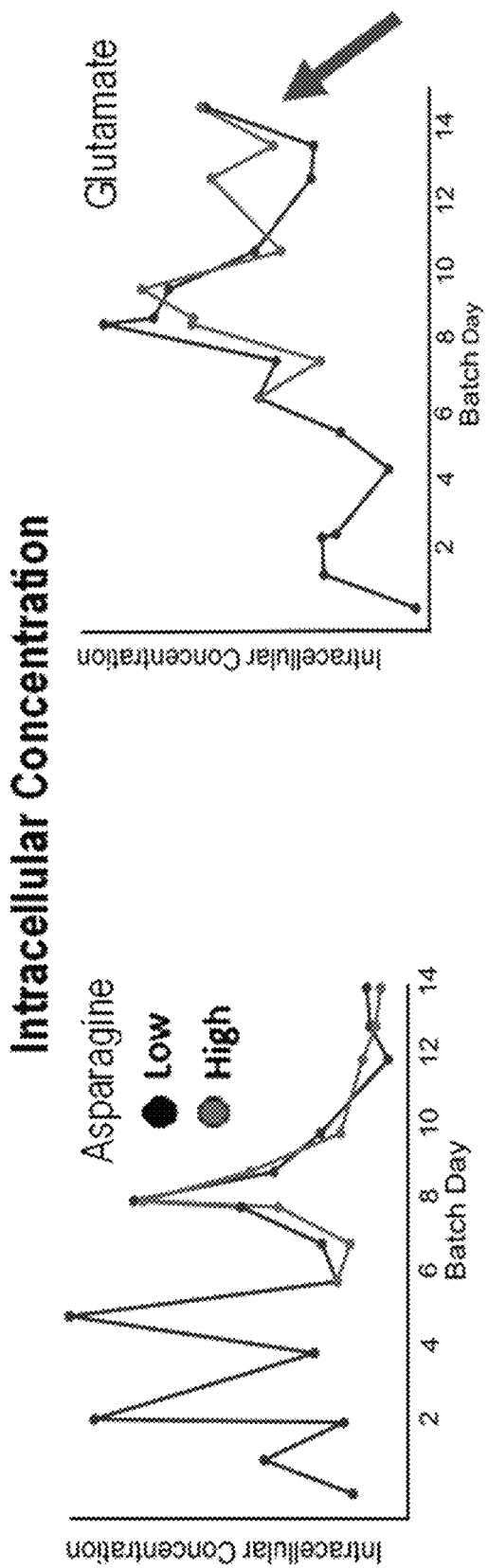

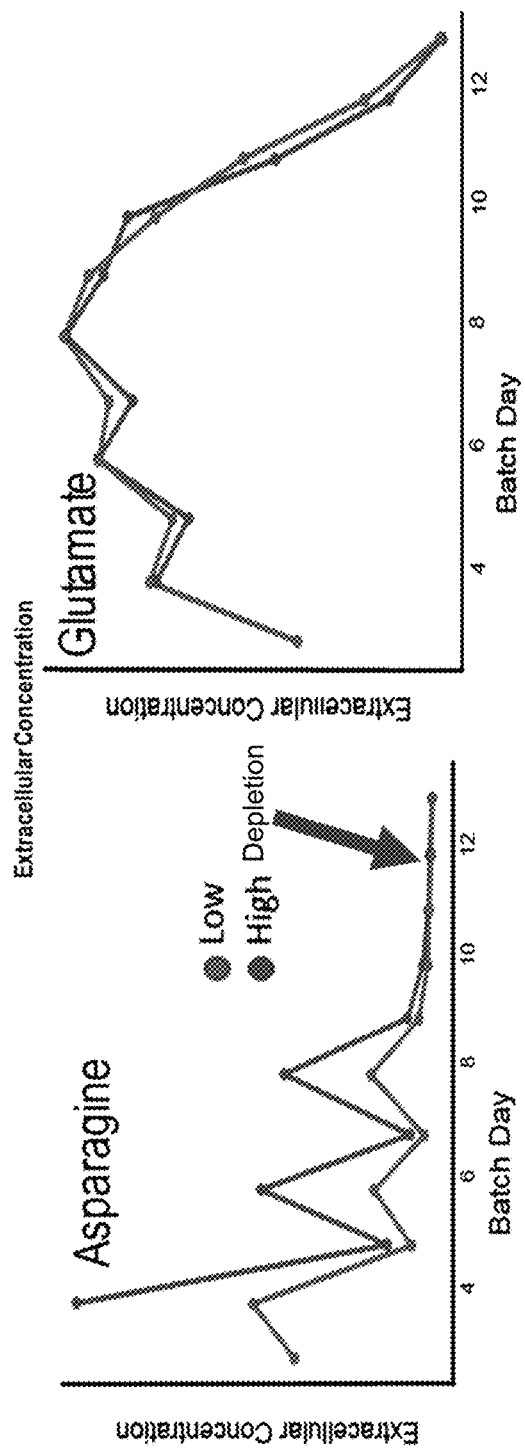
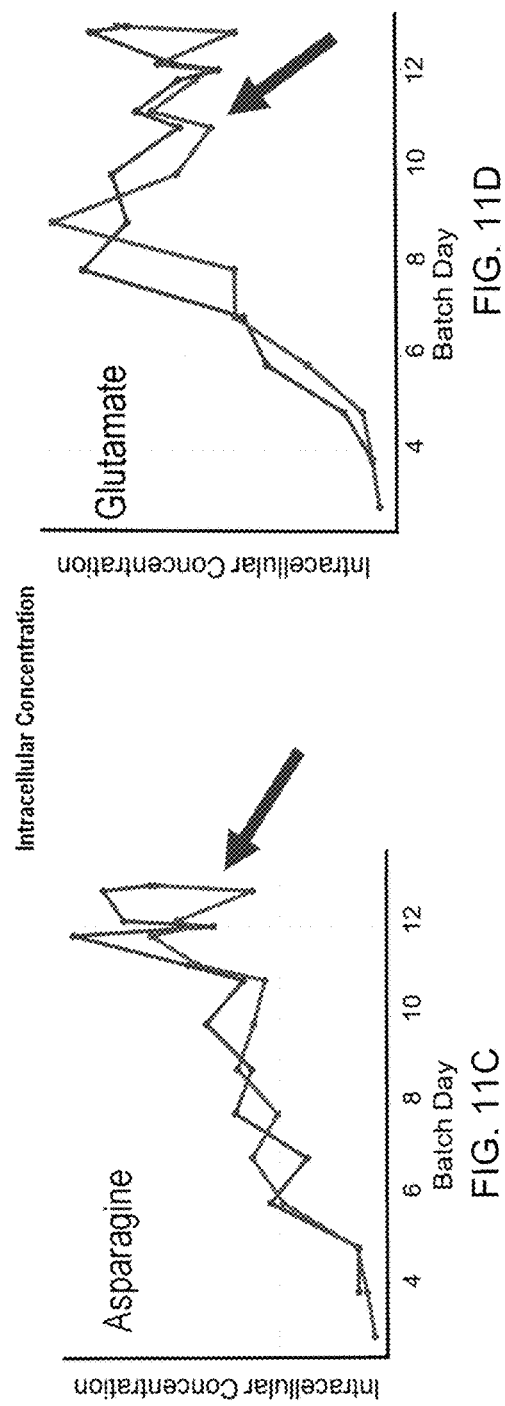
FIG. 11A
FIG. 11B
FIG. 11C
FIG. 11D

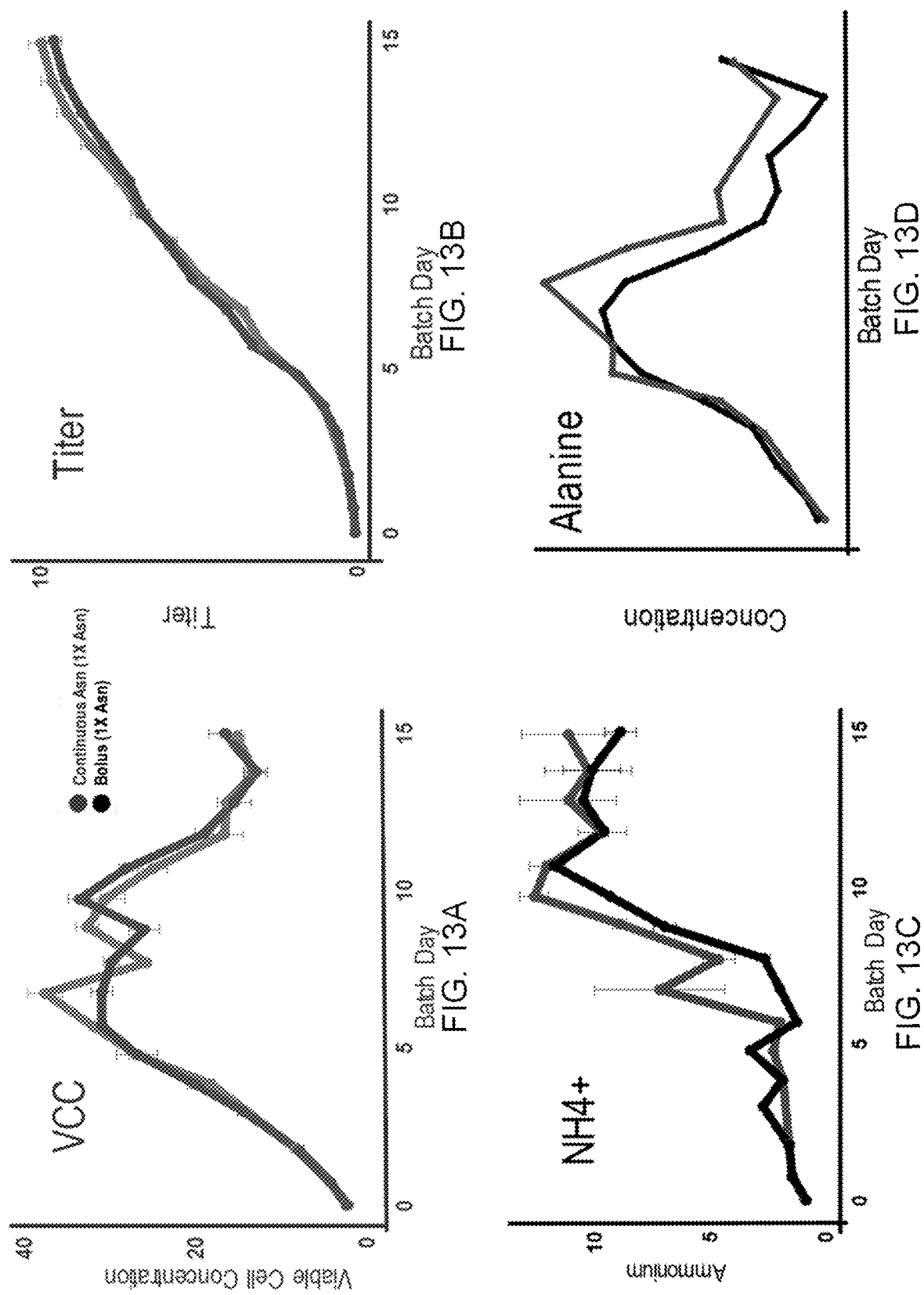

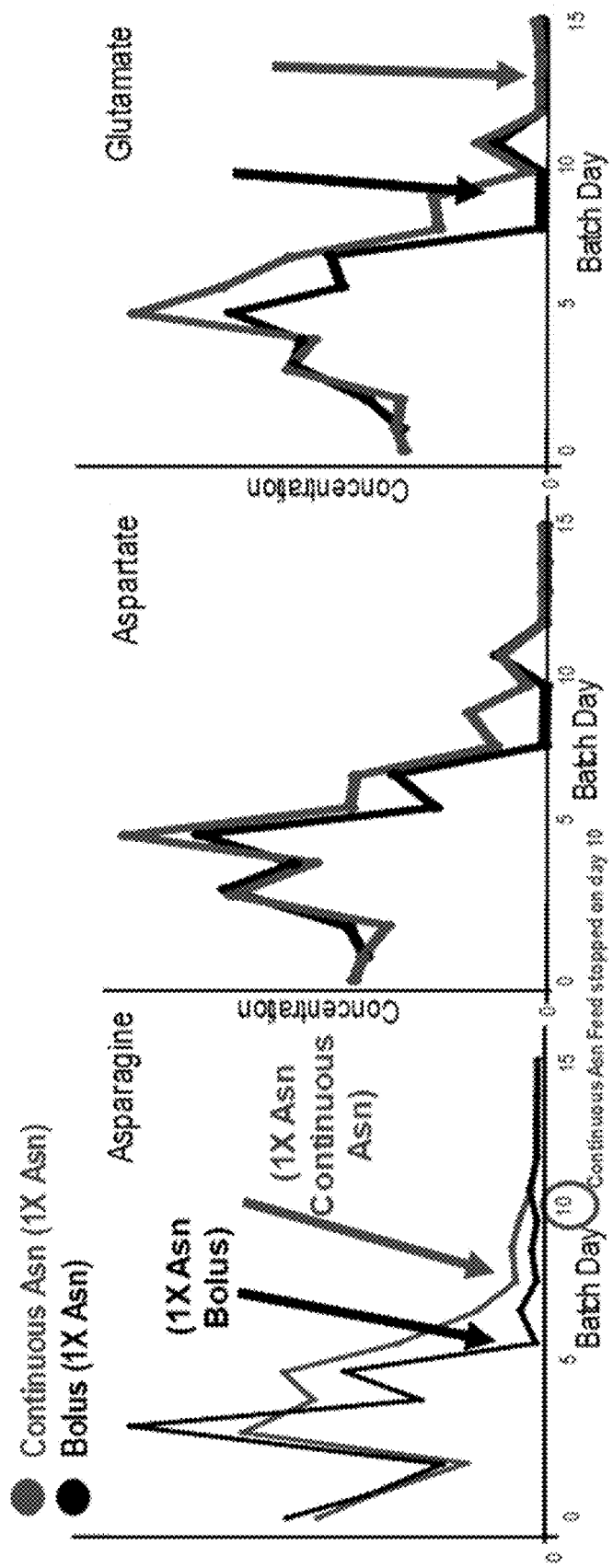

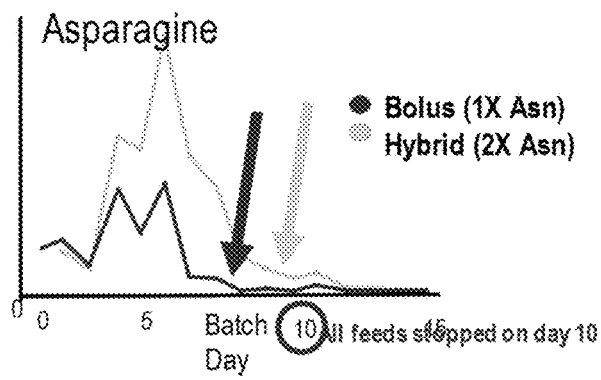
FIG. 16A
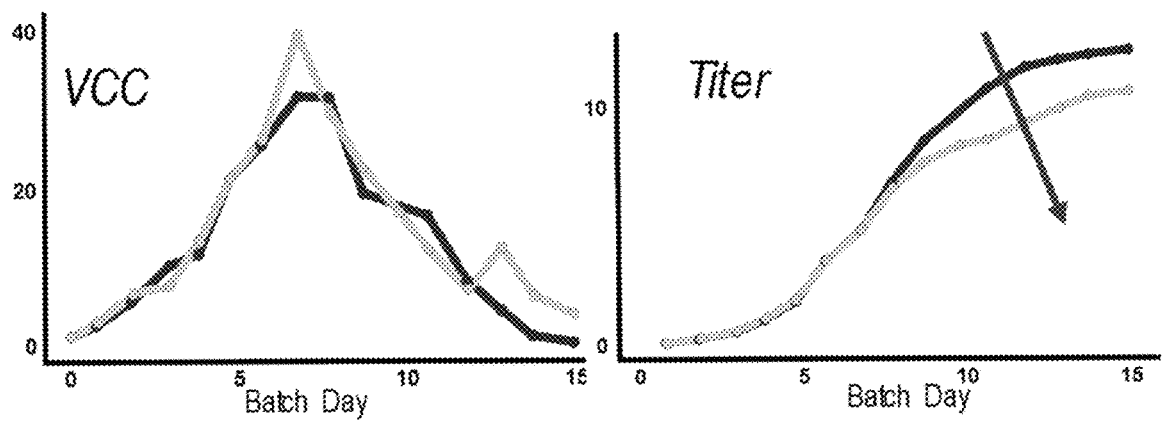
FIG. 16B
FIG. 16C
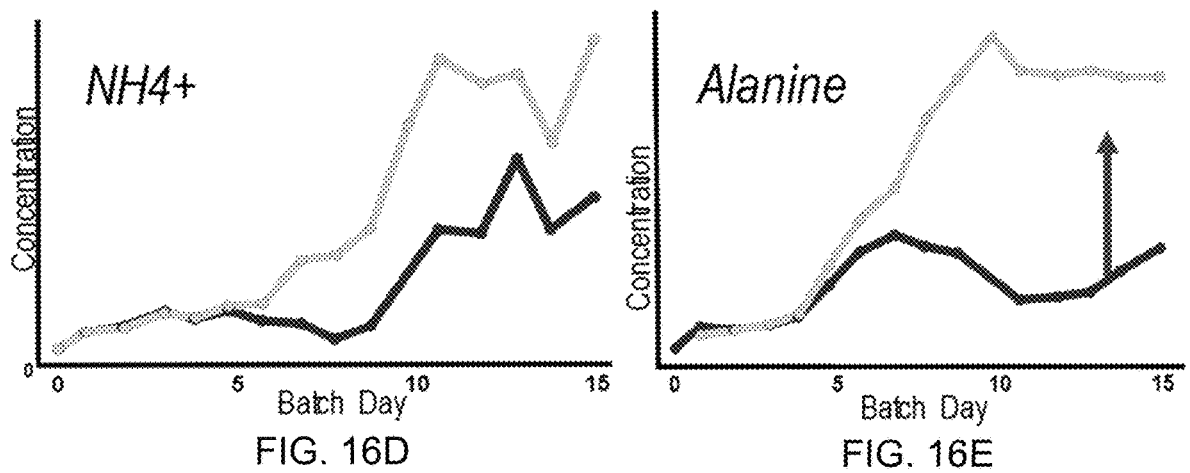
FIG. 16D
FIG. 16E

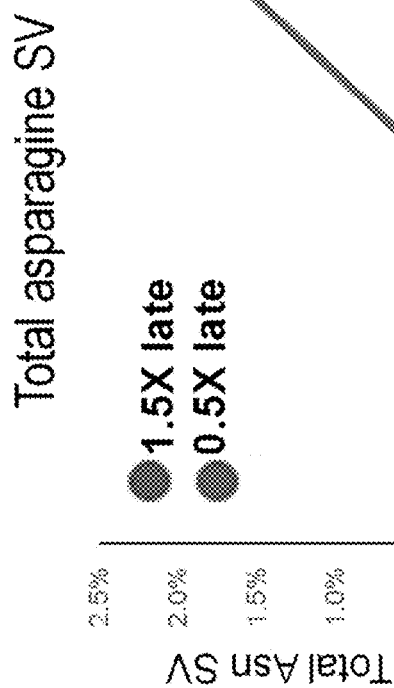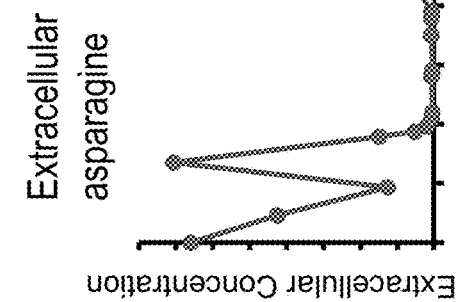

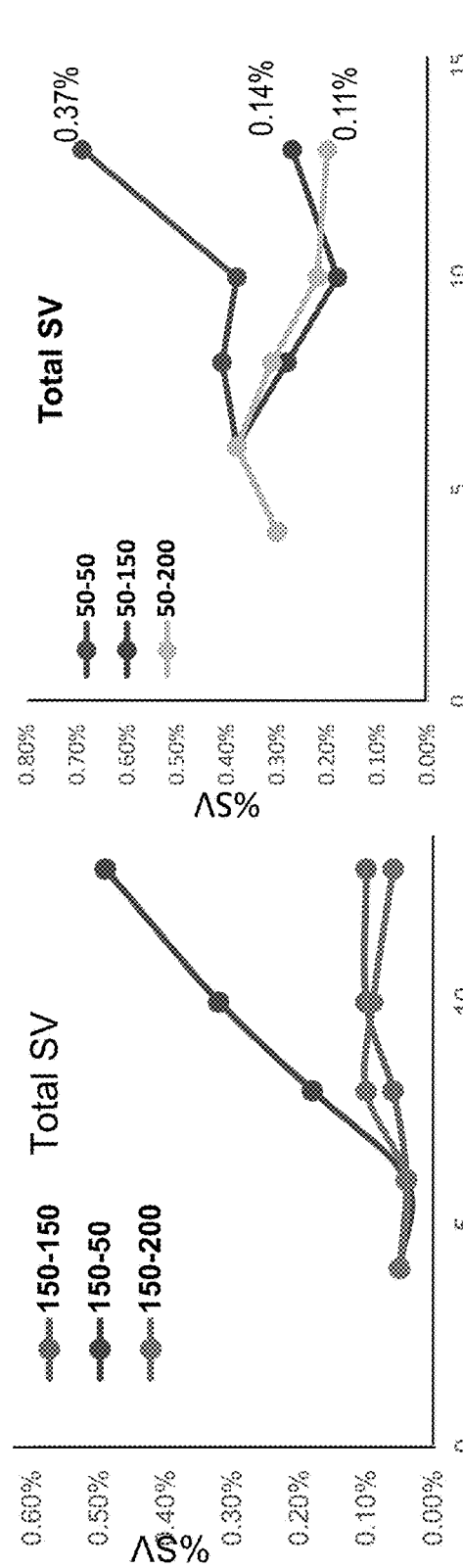
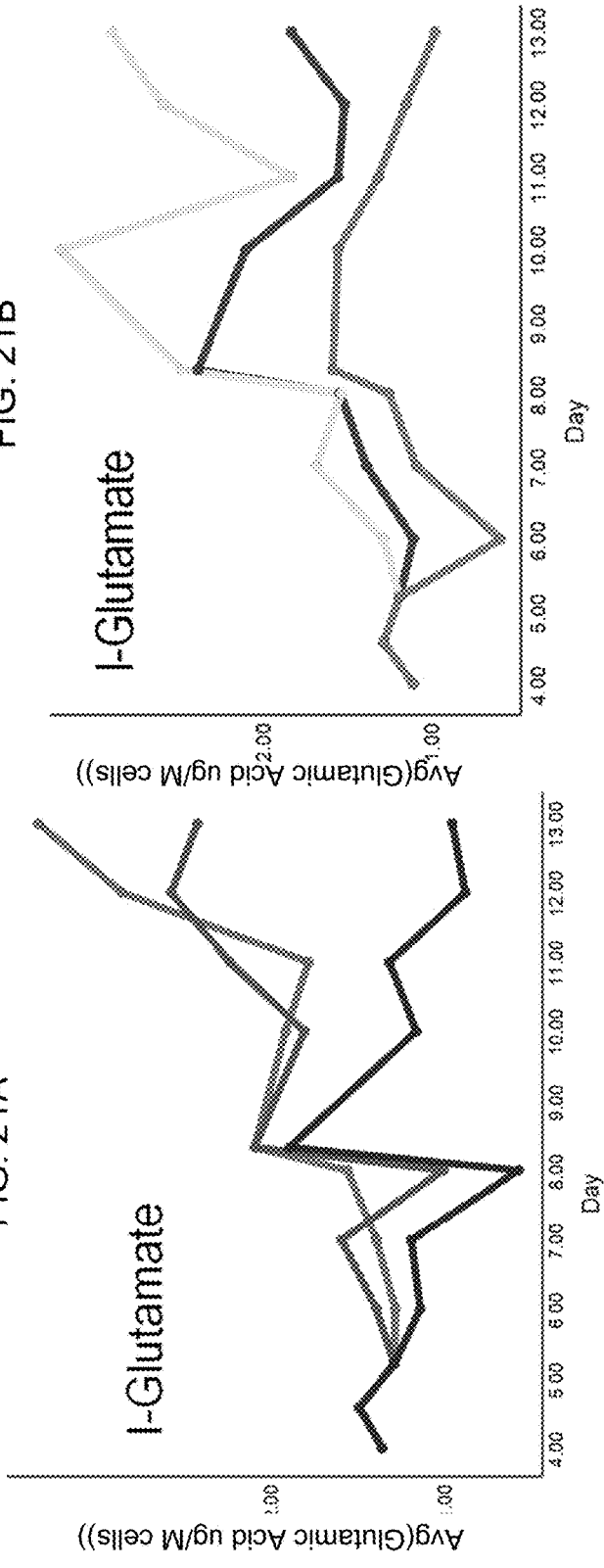
FIG. 21A, FIG. 21B, FIG. 21C, FIG. 21D

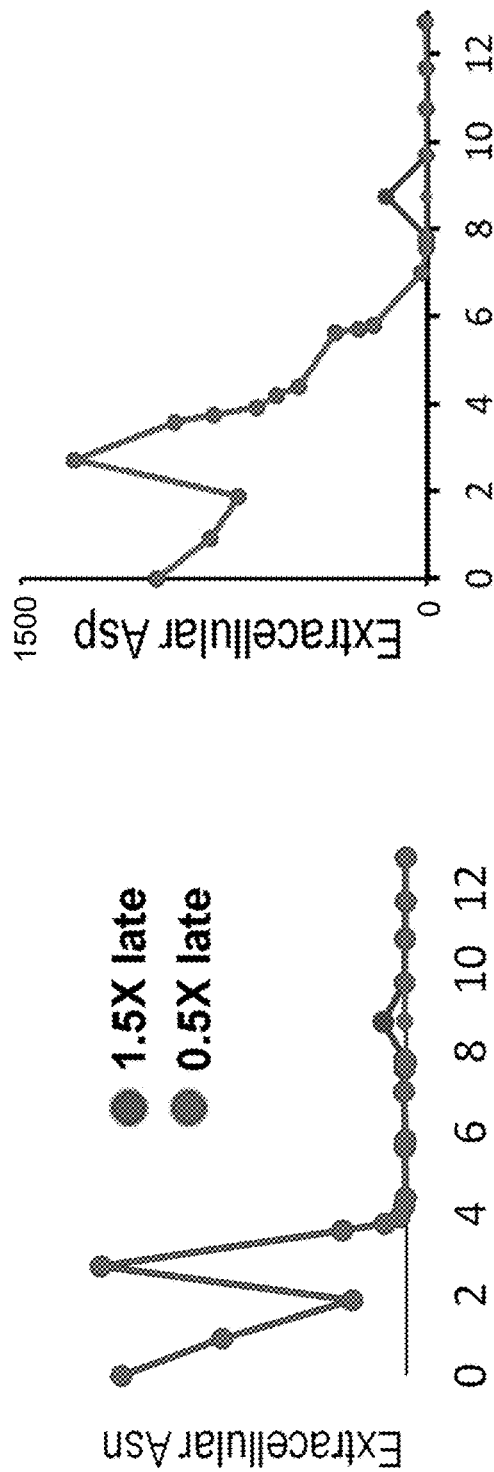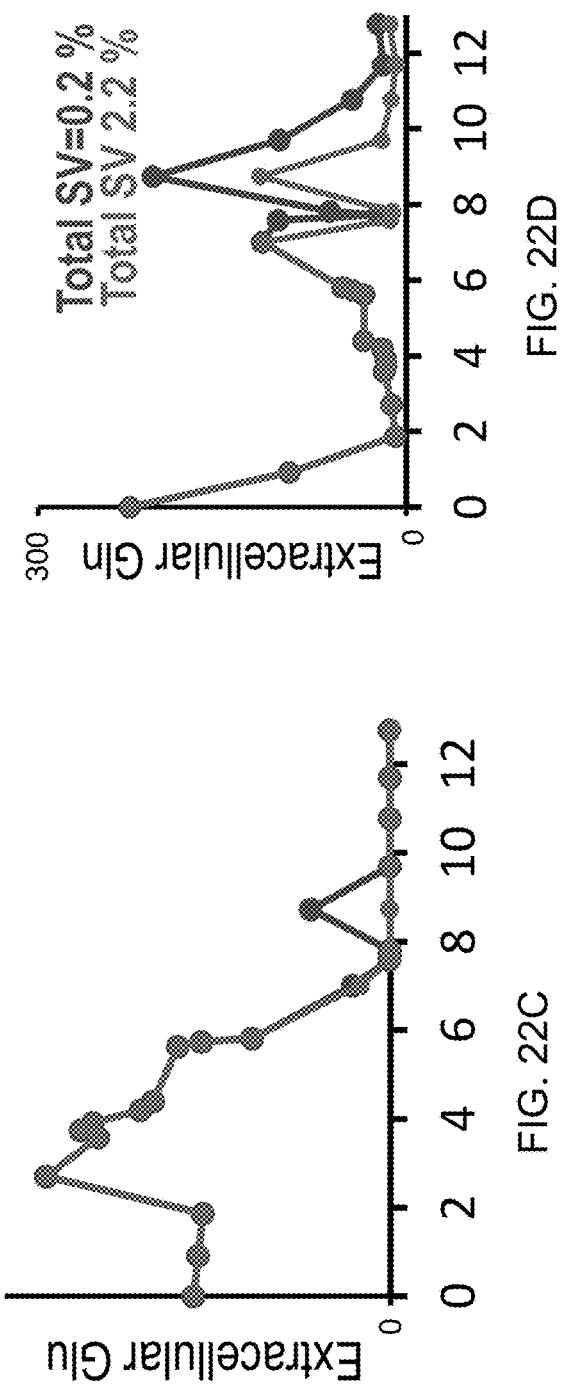
FIG. 22A  FIG. 22B  FIG. 22C  FIG. 22D

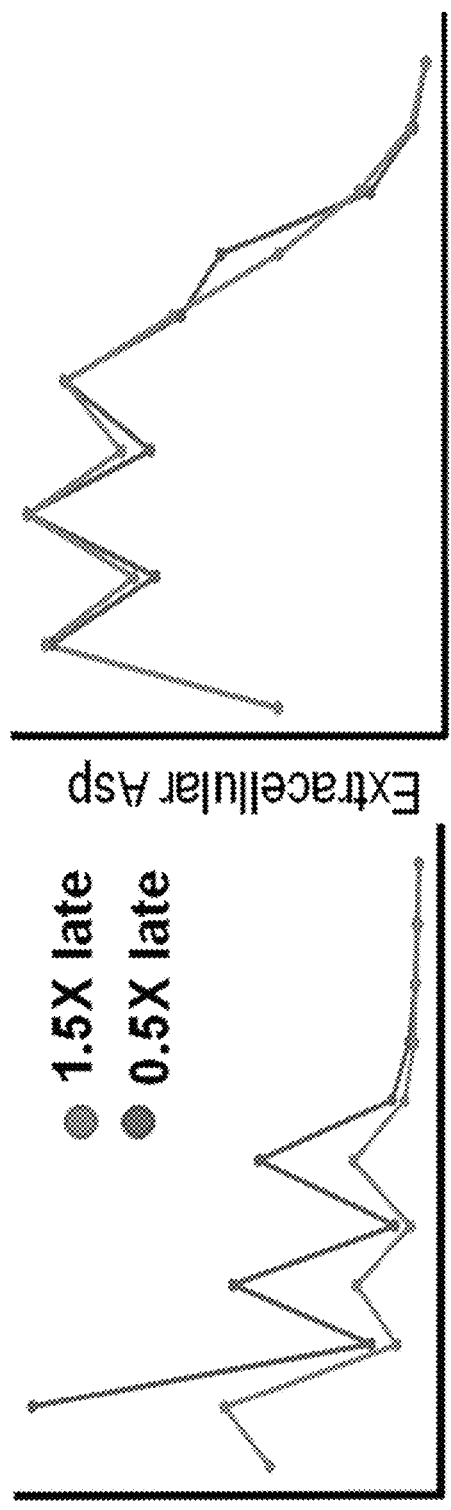
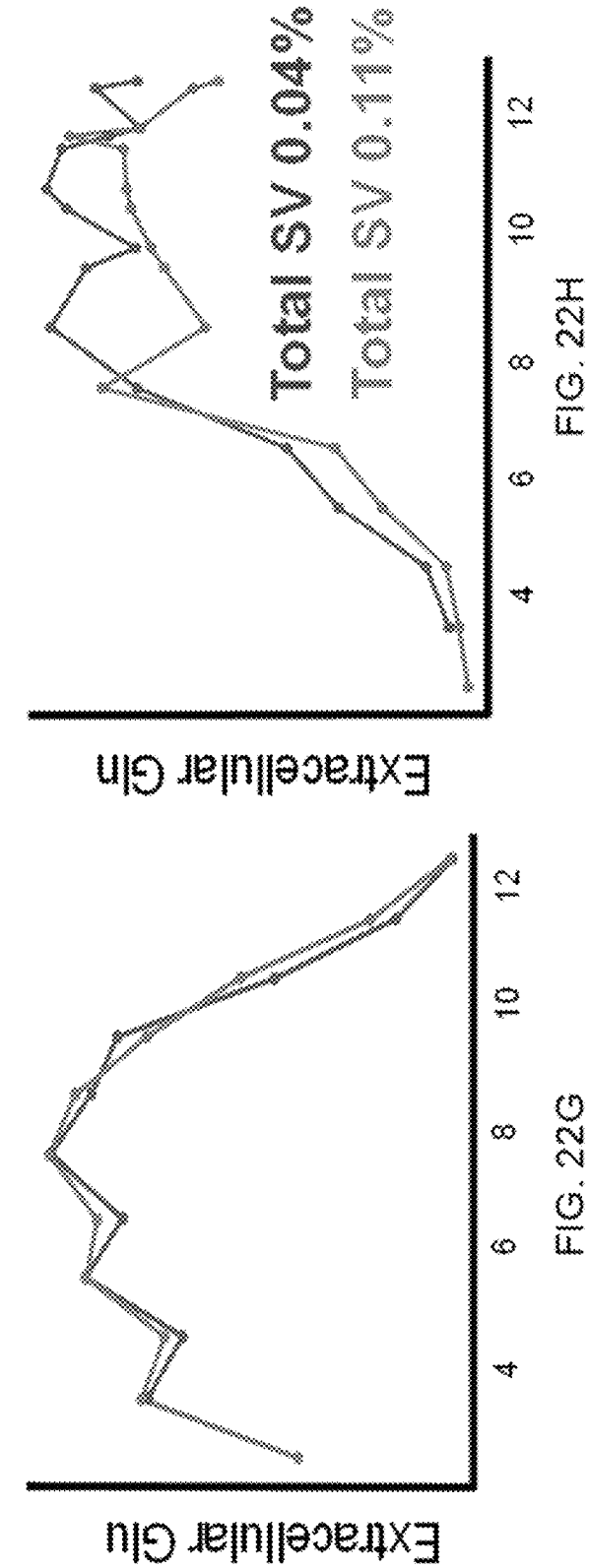
FIG. 22E
FIG. 22F
FIG. 22G
FIG. 22H

ASPARAGINE FEED STRATEGIES TO IMPROVE CELL CULTURE PERFORMANCE AND MITIGATE ASPARAGINE SEQUENCE VARIANTS

CROSS-REFERENCE TO RELATED APPLICATIONS

This application claims the benefit of the filing date of U.S. Provisional Application No. 63/072,740, filed Aug. 31, 2020, and U.S. Provisional Application No. 63/072,745, filed Aug. 31, 2020, the contents of which are herein incorporated by reference in their entireties for all purposes.

FIELD OF THE INVENTION

The invention relates to methods for culturing of cells to improve cell culture performance. The invention specifically relates to methods for culturing cells to improve cell culture performance and mitigate asparagine sequence variants using asparagine supplementation and for the production of protein biopharmaceuticals.

BACKGROUND OF THE INVENTION

Biological agents, particularly proteins and polypeptides, are often developed as novel biopharmaceutical products. Engineered cells that produce high levels of a particular protein of interest have become critically important for successful commercial production of these biopharmaceutical products. Control and optimization of cell culture conditions varies and has great effect on the level and quality of the therapeutic protein produced in cell culture.

It is customary to manufacture proteins via cell culture in a batch or fed-batch process. Early stages of inoculum growth after vial thaw include culturing cells in a seed culture. Typically, cells are grown at an exponential growth rate, such as in seed train bioreactors, in order to progressively increase size and/or volume of the cell population. After cell mass is scaled up through several bioreactor stages, cells are then transferred to a fed-batch, production bioreactor while the cells are still in exponential growth (log phase) (Gambhir, A. et al., 2003, *J Bioscience Bioeng* 95(4):317-327).

Following transfer to fed-batch culture, cells are cultured for a period of time whereas the composition of the medium is monitored and controlled to allow production of the protein or polypeptide of interest. After a particular yield is reached or cell viability, waste accumulation or nutrient depletion determines that the culture should be terminated, the produced protein or polypeptide is isolated. Many significant advances have been made over the past decade intending to improve recombinant protein yield, which currently reaches titers of multiple grams per liter. Advancements in protein manufacturing processes, as well as in cell line engineering, and cell culture medium and feed development, have contributed to the gain in protein yield. For instance, schemes to optimize cell culture medium and feed include nutrient supplementation and the design of chemically defined, serum-free media to support continuous cell growth and optimum product secretion.

However, there is still a need in the art for medium and methods for culturing cells, wherein the medium allows for healthy and robust cell growth and maintenance, and high-titer production of recombinant proteins.

SUMMARY OF THE INVENTION

In one aspect, a method for culturing eukaryotic cells for improved cell culture performance is provided. The method generally comprises propagating or maintaining eukaryotic cells in a defined cell culture medium; wherein the defined cell culture medium is supplemented with asparagine in an amount from about 3.6 mM to about 43.2 mM during early fed-batch cell culture and from about 3.6 mM to about 21.6 mM during late fed-batch cell culture; and maintaining said cells in said asparagine supplemented cell culture medium for at least a portion of the early fed-batch cell culture and at least a portion of the late fed-batch cell culture; wherein at least one cell culture performance parameter is improved by the asparagine supplementation, as compared to a similar method with a lower amount of asparagine supplementation or no asparagine supplementation in early and/or late fed-batch cell culture.

In certain embodiments, the asparagine supplement can be provided to the cell culture (both early phase and late phase) in bolus feed supplements (e.g., one bolus feed supplement during the early phase and one bolus feed supplement during the late phase), multiple bolus feed supplements over the course of at least a portion of the cell culture (e.g., 2, 3, 4, or 5 bolus feed supplements during the early phase and 2, 3, 4, or 5 bolus feed supplements during the late phase), or continuously over the course of at least a portion of the cell culture.

In certain embodiments, the at least one cell culture performance parameter is selected from the group consisting of increased cell viability, increased cell growth rate, increased cell density, increased titer of the recombinant protein of interest, increased yield of the recombinant protein of interest, reduction in depletions of essential amino acids in at least a portion of the cell culture, reduction in the formation of at least one cell culture by-product in at least a portion of the cell culture, and improvement of at least one indicator of protein quality. In certain embodiments, the at least one cell culture by-product is selected from the group consisting of ammonium ions and alanine. In certain embodiments, the at least one indicator of protein quality is a reduction in protein sequence variants.

In certain embodiments, the eukaryotic cell may be a mammalian cell, avian cell, insect cell, or yeast cell. In particular embodiments, the eukaryotic cell may be a CHO cell. In other embodiments, the recombinant protein may be selected an Fc-fusion protein, a receptor-Fc-fusion protein (TRAP), an antibody, an antibody fragment, or a ScFv-Fc fusion protein.

In other aspects, a method for preventing asparagine sequence variants in a polypeptide of interest expressed from mammalian cells in cell culture is provided. In certain embodiments, the method may comprise: propagating or maintaining mammalian cells in a defined cell culture medium; wherein the defined cell culture medium is supplemented with asparagine in an amount from about 3.6 mM to about 43.2 mM during early fed-batch cell culture and from about 3.6 mM to about 21.6 mM during late fed-batch cell culture; and maintaining said cells in said asparagine supplemented cell culture medium for at least a portion of the early and late fed-batch cell culture under conditions sufficient for expression of the polypeptide of interest In certain embodiments, the extracellular asparagine levels are maintained in the cell culture medium during at least early stage fed-batch cell culture above a depletion limit of about 0.1 mM such that the polypeptide of interest expressed by the mammalian cells comprise less than 0.30% of asparagine sequence variants at all individual sequence variant loci.

In other aspects, a method for detecting asparagine sequence variants in a recombinant polypeptide of interest expressed from a eukaryotic cell in cell culture is provided.

In certain embodiments, the method may comprise: propagating or maintaining eukaryotic cells in a defined cell culture medium; expressing a recombinant protein of interest from the eukaryotic cells; measuring intracellular and/or extracellular concentrations of one or more asparagine related amino acids in the defined cell culture medium; and correlating the measured concentrations of one or more asparagine related amino acids to the amount of asparagine sequence variants present in the expressed recombinant protein of interest. The measured concentrations of the one or more asparagine related amino acids is inversely correlated to the amount of asparagine sequence variants.

In yet other aspects, a method for monitoring and controlling cell culture medium conditions is provided. The method generally comprises: measuring one or more cell culture parameters in a cell culture using measuring one or more cell culture parameters in a cell culture in situ using one or more of freezing point depression, electrochemistry, digital imaging, photometry, bioprocess analyzer, or Raman spectroscopy; comparing the measured one or more cell culture parameters to a predetermined set point value for the cell culture parameter to determine if the one or more cell culture parameters are within a predetermined threshold range; and adjusting one or more of the cell culture parameters if a cell culture parameter is determined to be out of the predetermined threshold range. In certain embodiments, ammonium ion concentrations may be monitored and if it is determined that ammonium ion concentrations are outside of a predetermined threshold range for the particular cell culture, asparagine supplement feed may be adjusted such that the cell culture produces less ammonium while still receiving adequate asparagine.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the detailed description are to be regarded as illustrative in nature and not restrictive.

BRIEF DESCRIPTION OF THE DRAWINGS

FIG. 1A illustrates extracellular essential amino acid consumption during fed-batch cell culture using a standard feed strategy, while FIG. 1B illustrates the consumption of asparagine during fed-batch cell culture using a standard feed strategy.

FIG. 3B illustrates an increase in cell culture growth with increasing amounts of asparagine supplements, while

FIG. 4A illustrates a low and high asparagine supplement in late feeds, in accordance with embodiments of the disclosure. FIG. 4C illustrates overall cell culture productivity is not negatively impacted, while FIG. 4B illustrates an increase in by-product formation, in accordance with embodiments of the disclosure.

FIG. 5A illustrates extracellular essential amino acid concentrations in a fed batch cell culture and FIG. 5B illustrates extracellular asparagine concentrations in a fed batch cell culture, in accordance with embodiments of the disclosure. FIG. 5C illustrates an increase in cell culture growth, while FIG. 5D illustrates an increase in cell culture titer, in accordance with embodiments of the disclosure.

FIG. 6A illustrates asparagine consumption following asparagine supplements in early fed-batch cell culture, while

FIGS. 10A-10D, illustrate the effect of asparagine levels in late fed-batch cell culture of another exemplary high consuming cell line, in accordance with embodiments of the disclosure, with FIGS. 10A-10B showing extracellular asparagine (FIG. 10A) and extracellular glutamate (FIG. 10B) concentrations, and FIGS. 10C-10D showing intracellular asparagine (FIG. 10C) and intracellular glutamate (FIG. 10D) concentrations.

FIGS. 11A-11D, illustrate the effect of asparagine levels in late fed-batch cell culture of an exemplary low consuming cell line, in accordance with embodiments of the disclosure, with FIGS. 11A-11B showing extracellular asparagine (FIG. 11A) and extracellular glutamate (FIG. 11B) concentrations, and FIGS. 11C-11D showing intracellular asparagine (FIG. 11C) and intracellular glutamate (FIG. 11D) concentrations.

FIGS. 13A-13D, illustrate the effect of bolus and continuous asparagine feeds, in accordance with embodiments of the disclosure, with FIG. 13A showing viable cell count, FIG. 13B showing titer, FIG. 13C showing ammonium formation, and FIG. 13D showing alanine formation. FIGS. 13E-13G, shows that continuous asparagine supplement feed delays extracellular asparagine (FIG. 13E), aspartate (FIG. 13F) and glutamate (FIG. 13G) depletions, in comparison to bolus asparagine supplement feeds having the same total asparagine supplement amounts, in accordance with embodiments of the disclosure.

FIG. 14A shows the consumption of asparagine, while FIGS. 14B-14C shows the consumption of asparagine related metabolites (aspartate, FIG. 14B and glutamate FIG. 14C). FIG. 14D shows the formation of cell culture by-product, ammonium.

FIGS. 16A-16E, illustrate a hybrid feed approach (continuous asparagine supplement feed in combination with bolus asparagine supplement feed) in another exemplary cell line, in accordance with an embodiment of the disclosure, with FIG. 16A illustrating extracellular asparagine, FIG. 16B illustrating viable cell count, FIG. 16C illustrating titer, FIG. 16D illustrating ammonium formation, and FIG. 16E illustrating alanine formation.

FIGS. 19B-19D illustrate extracellular asparagine (FIG. 19B), aspartate (FIG. 19C), and glutamate (FIG. 19D), while FIGS. 19E-19G illustrate exemplary intracellular asparagine (FIG. 19E), aspartate (FIG. 19F), and glutamate (FIG. 19G).

FIGS. 20A-20D illustrate correlations between asparagine, asparagine related amino acids and asparagine sequence variants for another exemplary cell line (high consuming cell line), in accordance with embodiments of the disclosure. FIGS. 20B-20D illustrate extracellular asparagine (FIG. 20B), intracellular aspartate (FIG. 20C), and intracellular glutamate (FIG. 20D).

FIGS. 21A-21F illustrate asparagine sequence variant trends for an exemplary cell line, in accordance with embodiments of the disclosure. FIGS. 21A and 21C illustrate a high asparagine early feed strategy (FIG. 21A, sequence variant amounts as determined by mass spec, FIG. 21C, concentrations of intracellular glutamate). FIGS. 21B and 21D illustrate a low asparagine early feed strategy (FIG. 21B, sequence variant amounts as determined by mass spec, FIG. 21D, concentrations of intracellular glutamate). FIG. 21E shows intracellular glutamate levels for one exemplary cell line, with FIG. 21F show intracellular glutamate profile for another exemplary cell line.

FIGS. 22A-22H illustrate correlations between asparagine, asparagine related amino acids and asparagine sequence variants for exemplary cell lines. FIGS. 22A-22D illustrate extracellular asparagine (FIG. 22A), extracellular aspartate (FIG. 22B), extracellular glutamate (FIG. 22C) and extracellular glutamine (FIG. 22D) for an exemplary cell line for a high and low asparagine feed strategy. FIGS. 22E-22H illustrate extracellular asparagine (FIG. 22E), extracellular aspartate (FIG. 22F), extracellular glutamate (FIG. 22G) and extracellular glutamine (FIG. 22H) for another exemplary cell line for a high and low asparagine feed strategy.

FIG. 23A shows glutamine production via high asparagine feed strategies in an exemplary cell line. Similarly, FIG. 23B shows glutamine production via high asparagine feed strategies in an exemplary cell line. And finally, FIG. 23C shows that when no asparagine is supplemented on day 6 and 8, asparagine sequence variants are detected and extracellular glutamine falls below depletion limits (i.e., insufficient glutamine is produced via asparagine feed strategies).

DETAILED DESCRIPTION OF THE INVENTION

It accordance with aspects of the disclosure, it has been unexpectedly found that performing cell culture operations with optimized asparagine feed strategies can improve cell culture performance, including improvements in cell growth and protein production by a cell in a cell culture, relative to cell culture operations without such optimized asparagine feed strategies.

By way of non-limiting example, improvements in cell culture performance may be determined through evaluation of cell growth rate, cell density, cell viability, protein production, production of cell growth by-products (e.g., ammonium ion concentration, alanine concentration, etc.), and various combinations thereof. The improvement may be evaluated relative to cell culture operations without optimized asparagine feed strategies, as disclosed herein.

Asparagine is a non-essential amino acid, often consumed at high levels by cells in culture, which plays a central role in cell culture metabolism. In certain aspects of the disclosure, the role of asparagine in cell culture performance of fed-batch cell culture was investigated along with metabolic investigations of intracellular and extracellular asparagine and related metabolites.

As illustrated in FIGS. 1A and 1B, it was found that extracellular essential amino acids (FIG. 1A) are highly consumed and mainly depleted at the end of fed-batch cell culture, while extracellular asparagine, a non-essential amino acid, (FIG. 1B) is depleted across the timeline of fed-batch cell culture following a standard, bolus asparagine feed strategy.

Figure 2B:
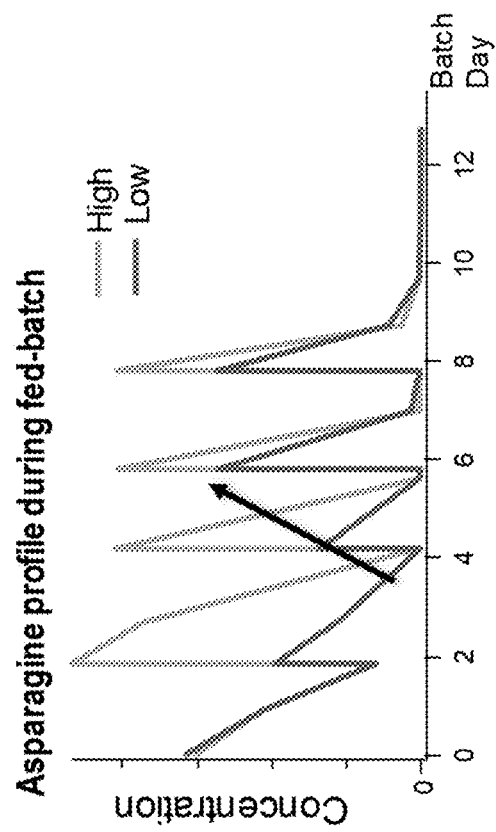
FIGS. 2A and 2B illustrate extracellular amino acid (FIG. 2A) and asparagine (FIG. 2B) consumption during fed-batch cell culture using various feed strategies, according to embodiments of the disclosure.
Figure 2A:
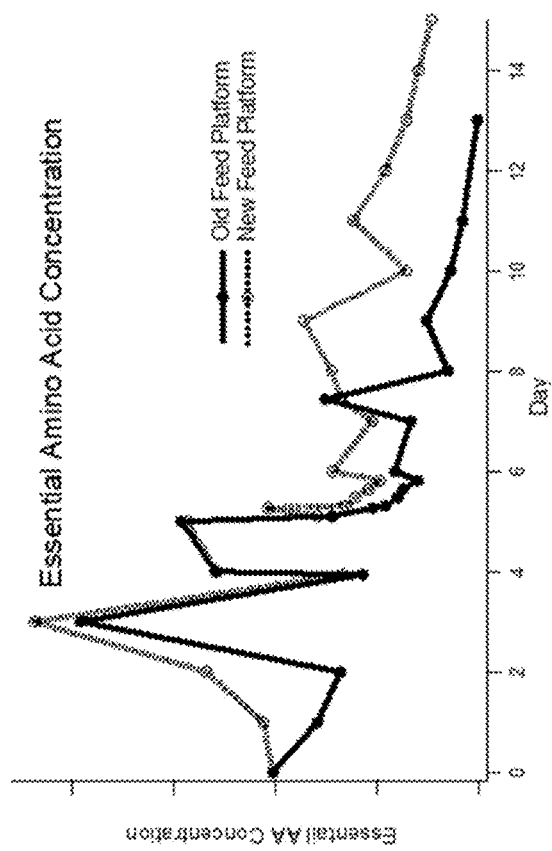

Embodiments of the present disclosure are directed to cell culture methods utilizing asparagine supplements to minimize, delay and prevent amino acid depletions, while improving cell culture performance. For instance, with reference to FIGS. 2A-2B, it was found that extracellular essential amino acid depletions can be prevented by essential amino acid supplementation (FIG. 2A), but that higher amounts of asparagine supplementation during growth phase (early stage) and stationary/decay phase (late stage) of the production phase of fed-batch cell culture does not prevent extracellular asparagine depletions in exemplary high producing cell lines, suggesting that asparagine consumption rates exceed stoichiometric demands (FIG. 2B). As such, in accordance with embodiments of the disclosure, the impact of asparagine supplementation during and after early stage, growth phase and late stage, stationary/decay phase of fed-batch cell culture was evaluated to select balanced asparagine feeding strategies, as described herein.

The section headings used herein are for organizational purposes only and are not to be construed as limiting the subject matter described. The methods and techniques described herein are generally performed according to conventional methods known in the art and as described in various general and more specific references that are cited and discussed throughout the present specification unless otherwise indicated. See, e.g., Sambrook et al., Molecular Cloning: A Laboratory Manual, 3rd ed., Cold Spring Harbor Laboratory Press, Cold Spring Harbor, N.Y. (2001) and Ausubel et al., Current Protocols in Molecular Biology, Greene Publishing Associates (1992), Harlow and Lane Antibodies: A Laboratory Manual, Cold Spring Harbor Laboratory Press, Cold Spring Harbor, N.Y. (1990), and Julio E. Celis, Cell Biology: A Laboratory Handbook, 2nd ed., Academic Press, New York, N.Y. (1998), and Dieffenbach and Dveksler, PCR Primer: A Laboratory Manual, Cold Spring Harbor Laboratory Press, Cold Spring Harbor, N.Y. (1995). All publications mentioned throughout this disclosure are incorporated herein by reference in their entirety.

Definitions

Unless defined otherwise, all technical and scientific terms used herein have the same meaning as commonly understood by one of ordinary skill in the art to which this invention belongs. Although any methods and materials similar or equivalent to those described herein can be used in the practice of the present invention, particular methods and materials are now described.

The terms "peptide," "polypeptide" and "protein" are used interchangeably throughout and refer to a molecule comprising two or more amino acid residues joined to each other by a peptide bond. Peptides, polypeptides and proteins may also include modifications such as glycosylation, lipid attachment, sulfation, gamma-carboxylation of glutamic acid residues, alkylation, hydroxylation and ADP-ribosylation. Peptides, polypeptides, and proteins can be of scientific or commercial interest, including protein-based drugs. Peptides, polypeptides, and proteins include, among other things, antibodies and chimeric or fusion proteins. Peptides, polypeptides, and proteins are produced by recombinant animal cell lines using cell culture methods.

The term "heterologous polynucleotide sequence", as used herein refers to nucleic acid polymers encoding proteins of interest, such as chimeric proteins (like trap molecules), antibodies or antibody portions (e.g., VH, VL, CDR3) that are produced as a biopharmaceutical drug substance. The heterologous polynucleotide sequence may be manufactured by genetic engineering techniques (e.g., such as a sequence encoding a chimeric protein, or a codon-optimized sequence, an intronless sequence, et cetera) and introduced into the cell, where it may reside as an episome or be integrated into the genome of the cell. The heterologous polynucleotide sequence may be a naturally occurring sequence that is introduced into an ectopic site within the production cell genome. The heterologous polypeptide sequence may be a naturally occurring sequence from another organism, such as a sequence encoding a human ortholog.

"Antibody" refers to an immunoglobulin molecule consisting of four polypeptide chains, two heavy (H) chains and two light (L) chains inter-connected by disulfide bonds. Each heavy chain has a heavy chain variable region (HCVR or VH) and a heavy chain constant region. The heavy chain constant region contains three domains, CH1, CH2 and CH3. Each light chain has a light chain variable region and a light chain constant region. The light chain constant region consists of one domain (CL). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The term "antibody" includes reference to both glycosylated and non-glycosylated immunoglobulins of any isotype or subclass. The term "antibody" includes antibody molecules prepared, expressed, created or isolated by recombinant means, such as antibodies isolated from a host cell transfected to express the antibody. The term antibody also includes bispecific antibody, which includes a heterotetrameric immunoglobulin that can bind to more than one different epitope. Bispecific antibodies are generally described in US Patent Application Publication No. 2010/0331527, which is incorporated by reference into this application.

The term "antigen-binding portion" of an antibody (or "antibody fragment"), refers to one or more fragments of an antibody that retain the ability to specifically bind to an antigen. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) *Nature* 241:544-546), which consists of a VH domain, (vi) an isolated CDR, and (vii) an scFv, which consists of the two domains of the Fv fragment, VL and VH, joined by a synthetic linker to form a single protein chain in which the VL and VH regions pair to form monovalent molecules. Other forms of single chain antibodies, such as diabodies are also encompassed under the term "antibody" (see e.g., Holliger et al. (1993) *PNAS USA* 90:6444-6448; Poljak et al. (1994) *Structure* 2:1121-1123).

Still further, an antibody or antigen-binding portion thereof may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov et al. (1995) *Human Antibodies and Hybridomas* 6:93-101) and use of a cysteine residue, a marker peptide and a C-terminal polyhistidine tag to make bivalent and biotinylated scFv molecules (Kipriyanov et al. (1994) *Mol. Immunol.* 31:1047-1058). Antibody portions, such as Fab and F(ab')2 fragments, can be prepared from whole antibodies using conventional techniques, such as via papain or pepsin digestion of whole antibodies. Moreover, antibodies, antibody portions and immunoadhesion molecules can be obtained using standard recombinant DNA techniques commonly known in the art (see Sambrook et al., 1989).

The term "human antibody" is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (see e.g., Taylor et al. (1992) *Nucl. Acids Res.* 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

"Fc fusion proteins" comprise part or all of two or more proteins, one of which is an Fc portion of an immunoglobulin molecule, which are not otherwise found together in nature. Preparation of fusion proteins comprising certain heterologous polypeptides fused to various portions of antibody-derived polypeptides (including the Fc domain) has been described, e.g., by Ashkenazi et al., *Proc. Natl. Acad. ScL USA* 88: 10535, 1991; Byrn et al., *Nature* 344:677, 1990; and Hollenbaugh et al., "Construction of Immunoglobulin Fusion Proteins", in *Current Protocols in Immunology*, Suppl. 4, pages 10.19.1-10.19.11, 1992. "Receptor Fc fusion proteins" comprise one or more extracellular domain(s) of a receptor coupled to an Fc moiety, which in some embodiments comprises a hinge region followed by a CH2 and CH3 domain of an immunoglobulin. In some embodiments, the Fc-fusion protein contains two or more distinct receptor chains that bind to a one or more ligand(s). For example, an Fc-fusion protein is a trap, such as for example an IL-1 trap (e.g., rilonacept, which contains the IL-1RAcP ligand binding region fused to the IL-1R1 extracellular region fused to Fc of hIgG1; see U.S. Pat. No. 6,927,004), or a VEGF trap (e.g., aflibercept, which contains the Ig domain 2 of the VEGF receptor Flt1 fused to the Ig domain 3 of the VEGF receptor Flk1 fused to Fc of hIgG1; see U.S. Pat. Nos. 7,087,411 and 7,279,159).

Asparagine Supplementation

In certain aspects of the disclosure, it was found that supplementing fed-batch cell culture with asparagine impacts cell culture performance. However, it was also found that regardless of the amount of asparagine supplementation, depletions of asparagine during fed-batch cell culture cannot be avoided. In this regard, without being limited, in certain aspects of the disclosure, it was unexpectedly found that while asparagine depletions during fed-bath cell culture can have negative impacts on cell culture performance, asparagine fed at too high levels can also negatively impact cell culture performance, e.g., in the form of byproduct formation such as ammonium.

In certain embodiments, a method for culturing eukaryotic cells for improved cell culture performance is provided. The method generally comprises propagating or maintaining eukaryotic cells in a defined cell culture medium; wherein the defined cell culture medium is supplemented with asparagine in an amount from about 2.6 mM to about 28.6 mM during early fed-batch cell culture and from about 2.6 mM to about 21.6 mM during late fed-batch cell culture; and maintaining said cells in said asparagine supplemented cell culture medium for at least a portion of the early fed-batch cell culture and at least a portion of the late fed-batch cell culture; wherein the performance of the cell culture is improved by the asparagine supplementation, as compared to a similar method with a lower amount of asparagine supplementation in the early and/or late fed-batch cell culture.

As will be described in further detail herein, the asparagine supplement can be provided to the cell culture (both early phase and late phase) in bolus feed supplements (e.g., one bolus feed supplement during the early phase and one bolus feed supplement during the late phase), multiple bolus feed supplements over the course of at least a portion of the cell culture (e.g., 2, 3, 4, or 5 bolus feed supplements during the early phase and 2, 3, 4, or 5 bolus feed supplements during the late phase), or continuously over the course of at least a portion of the cell culture.

In certain embodiments, the asparagine supplement may be provided as part of the bulk feed, or as a separate supplement feed to the bulk feed. More particularly, the supplement may be provided to the cell culture (both early phase and late phase) in bolus or continuous feeds, as part of the bulk feed or as a separate supplement feed to the bulk feed.

In certain embodiments, cell culture density and/or titer is increased, as compared to a similar method with a lower amount of asparagine supplementation in early and/or late fed-batch cell culture. In certain aspects, the cell culture may maintain a viable cell count of at least about 10-50 Mcells/ml, e.g., about 10-35 Mcells/ml, during at least a portion of the late fed-batch cell culture following asparagine supplementation.

In certain embodiments, the eukaryotic cell is a high asparagine consuming cell line, such that the cell consumes at least about 1.8 mM/day to about 9.3 mM/day of asparagine. In other embodiments, the eukaryotic cell is a low asparagine consuming cell line, such that the cell consumes at least about 0.32 mM/day to about 1.8 mM/day of asparagine.

In certain embodiments, the method further comprises expressing a recombinant protein of interest from the eukarvotic cells during the fed-batch cell culture. The titer of the recombinant protein of interest may be at least 3%, 5%, 8%, 9%, 10%, 11%, 12%, 13%, 14%, 15%, or at least 20% higher than the titer compared to cell(s) cultured in non-asparagine supplemented culture. The yield of the recombinant protein of interest may be increased by at least 0.1 g/L, at least 0.5 g/L, at least 1 g/L, at least 1.2 g/L, at least 1.4 g/L, at least 1.6 g/L, at least 1.8 g/L, at least 2 g/L, at least 2.2 g/L, at least 2.4 g/L, or at least 2.5 g/L compared to a similar method wherein cell(s) are cultured in non-asparagine supplemented culture. In certain embodiments, the eukaryotic cell is a high producing cell line, such that the recombinant protein of interest is produced at a yield of at least 4 g/L, at least 5 g/L, at least 6 g/L, at least 7 g/L, at least 8 g/L, at least 9 g/L, or at least 10 g/L, at least 11 g/L, at least 12 g/L, at least 13 g/L, at least 14 g/L.

In certain embodiments, the defined cell culture medium is supplement with asparagine in an amount from about 2.6 mM to about 28.6 mM, from about 3.0 mM to about 25.0 mM, from about 5.0 mM to about 23.0 mM, from about 6.0 mM to about 22.0 mM, from about 7.2 mM to about 21.6 mM, about 10.6 mM, etc., during early fed-batch cell culture and from about 2.6 mM to about 21.6 mM, about 2.6 mM to about 20.0 mM, about 2.6 mM to about 18.0 mM, about 2.6 mM to about 16.0 mM, about 2.6 mM to about 14.4 mM, about 5.3 mM, etc., during late fed-batch cell culture. In other embodiments, the defined cell culture medium is supplemented with asparagine in an amount from about 7.2 mM to about 21.6 mM during early fed-batch and about 2.6 mM to about 14.4 mM during late fed-batch. In other embodiments, the defined cell culture medium is supplemented with asparagine in an amount of about 10.6 mM during early stage fed-batch and about 5.3 mM during late stage fed-batch.

In certain embodiments, the cells may be maintained under asparagine supplemented cell culture conditions for at least 2 days, at least 3 days, at least 4 days, at least 5 days, or for the duration of the fed-batch cell culture. The asparagine supplement may be provided at least once, at least twice, at least three times, at least four times, at least five times, daily or continuously for at least a portion of the early fed-batch cell culture. Likewise, the asparagine supplement may be provided at least once, at least twice, at least three times, at least four times, at least five times, daily or continuously for at least a portion of the late fed-batch cell culture.

In certain embodiments, the cells may be maintained under asparagine supplemented cell culture conditions in a cell culture having a volume of at least 500 liters, at least 750 liters, at least 1,000 liters, at least 1,500 liters, at least 2,000 liters, at least 2,500 liters, at least 5,000 liters, at least 7,500 liters, at least 10,000 liters, at least 12,500 liters, at least 15,000 liters, at least 20,000 liters, at least 25,000 liters, between 500 liters and 25,000 liters, etc.

In certain embodiments, the asparagine supplement may be provided continuously in early and/or late fed-batch cell culture. In certain aspects, continuous asparagine supplementation in cell culture results in delays of extracellular amino acid depletions of asparagine, aspartic acid, and glutamic acid of at least 1 day, at least 2 days, at least 3 days, or at least 4 days or more, as compared to a similar method with asparagine supplementation provided in early and/or late fed-batch cell culture as a bolus feed.

More particularly, in certain embodiments, as described herein, the asparagine supplement may be provided continuously for at least 2 days, at least 3 days, at least 4 days, at least 5 days, or for the duration of the early fed-batch cell culture. Similarly, in certain embodiments, the asparagine supplement may be provided continuously for at least 2 days, at least 3 days, at least 4 days, at least 5 days, or for the duration of the late fed-batch cell culture.

Without being limited, in certain embodiments, the asparagine supplement may be provided continuously beginning on or after day 2 of the fed-batch cell culture, and thereafter for at least a portion of the early fed-batch cell culture, or on or after day 5 of the fed-batch cell culture, and thereafter for at least a portion of the late fed-batch cell culture. Such late fed-batch continuous asparagine supplement may be discontinued on or after day 10 of the late fed-batch cell culture.

Asparagine Supplementation to Mitigate Asparagine Sequence Variants

In other aspects, it was found that asparagine (Asn) depletions during fed-batch cell culture can result in occurrence of asparagine sequence variants (SV) in a polypeptide of interest expressed from mammalian cells in the cell culture. By way of background, as disclosed in U.S. Pat. No. 9,096,879, which is herein incorporated by reference, it is known that depletion of a particular amino acid during recombinant expression of a polypeptide of interest in mammalian cells can trigger misincorporation of amino acids. For instance, the depletion of a particular amino acid during recombinant expression of a polypeptide of interest in mammalian cells may result in that amino acid being substituted by a second amino acid during translation of a polypeptide of interest in a mammalian cell. Asn→Ser asparagine sequence variants (i.e., misincorporation of serine in place of asparagine during translation of the polypeptide of interest) are observed, but may be minimized by supplementing cell culture media with asparagine.

In this regard, it was found that supplementation of fed-batch cell culture with asparagine can minimize formation of asparagine SV. In accordance with embodiments of the disclosure, it was unexpectedly found that asparagine SV may be minimized by maintaining extracellular asparagine levels in cell culture medium during at least early stage fed-batch cell culture above a depletion limit of about 1.0 mM, about 0.5 mM, about 0.25 mM, about 0.2 mM, about 0.1 mM, etc. In certain embodiments, extracellular asparagine levels in cell culture medium may be maintained above such depletion limit during at least the first 6 days of early stage fed-batch cell culture, at least the first 5 days of early stage fed-batch cell culture, at least the first 4 days of early stage fed-batch cell culture, at least first 3 days of early stage fed-batch cell culture, at least the first 2 days of early stage fed-batch cell culture, etc. By way of example, the duration of maintaining above such depletion limit may include providing asparagine supplement at least once, at least twice, at least three times, daily, continuously, etc., during early stage fed-batch cell culture.

In accordance with certain embodiments of the disclosure, supplementation of fed-batch cell culture with asparagine can mitigate, i.e., prevent occurrence of asparagine SV to amounts of less than about 0.50% of asparagine SV in the polypeptide of interest, amounts of less than about 0.45% of asparagine SV in the polypeptide of interest, amounts of less than about 0.40% of asparagine SV in the polypeptide of interest, amounts of less than about 0.35% of asparagine SV in the polypeptide of interest, amounts of less than about 0.30% of asparagine SV in the polypeptide of interest, amounts of less than about 0.25% of asparagine SV in the polypeptide of interest, amounts of less than about 0.20% of asparagine SV in the polypeptide of interest, amounts of less than about 0.15% of asparagine SV in the polypeptide of interest, amounts of less than about 0.10% of asparagine SV in the polypeptide of interest, no amount of asparagine SV detected, etc.

In certain embodiments, supplementation of fed-batch cell culture with asparagine can mitigate asparagine SV formation to such levels after, e.g., day 4 of the cell culture, day 5 of the cell culture, day 6 of the cell culture, day 7 of the cell culture, day 8 of the cell culture, day 9 of the cell culture, day 10 of the cell culture, day 11 of the cell culture, day 12 of the cell culture, day 13 of the cell culture, day 14 of the cell culture, during late fed-batch cell culture, etc.

In certain embodiments, the cell culture may be supplemented with asparagine as generally described herein, e.g., in an amount from about 2.6 mM to about 28.6 mM, e.g., from about 7.2 mM to about 21.6 mM, from about 10.6 mM, etc., during early fed-batch cell culture and from about 2.6 mM to about 21.6 mM, e.g., from about 2.6 mM to about 14.4 mM, from about 5.3 mM, etc., during late stage fed-batch cell culture. In certain embodiments, the asparagine supplement may be provided as part of a bulk feed or as a separate asparagine supplement feed.

In certain aspects, it was unexpectedly found that asparagine SV formation may be mitigated if sufficient asparagine supplementation is provided during early stage fed-batch cell culture to prevent asparagine depletion through at least day 4 of fed-batch cell culture (e.g., in certain embodiments, the second bolus feed). In certain embodiments, supplementation in early stage fed-batch cell culture followed by sufficient asparagine supplementation thereafter and during late stage fed-batch cell culture to prevent aspartate (Asp) and glutamate (Glu) depletions (or to produce enough glutamine (Gln), i.e., >100 mg/L) while balancing formation of excess ammonium provided for optimized mitigation of asparagine SV.

In certain embodiments, it was unexpectedly found that providing sufficient asparagine supplementation during early stage fed-batch cell culture to maintain levels above depletions limits (e.g., through at least day 4 of fed-batch cell culture), and thereafter providing sufficient asparagine supplementation during late stage fed-batch cell culture to minimize undesired by-product formation (e.g., ammonium). By way of non-limiting example, asparagine supplementation during early stage and late stage fed-batch cell culture may meet any of the following criteria to provide for a low risk for asparagine SV.

| Non-limiting Exemplary Early Stage Fed Batch Conditions | | |
| --- | --- | --- |
| Amino Acid | 0.1 mM Depletion Limit | Min. Feed Guideline (mg/L) D4/Second feed |
| L-Asparagine•H2O | 15 mg/L | 100 mg/L |

| Non-limiting Exemplary Late Stage Fed Batch Conditions | | |
| --- | --- | --- |
| Amino Acid | 0.1 mM Depletion Limit | Min. Feed Guideline (mg/L) D8-end of fed-batch |
| L-Glutamic Acid | 15 mg/L | 100 mg/L |
| L-Aspartic Acid | 13 mg/L | 100 mg/L |
| L-Asparagine•H2O | 15 mg/L | 15 mg/L |
| L-Glutamine | 15 mg/L | 100 mg/L |

Asparagine Related Amino Acids

In other aspects of the disclosure, it has been found that targeted asparagine depletion can impact non-essential amino acids that are related to asparagine through cellular metabolic pathways. By way of background, asparagine (Asn), aspartate (Asp), glutamate (Glu), and glutamine (Gln) can be interconverted into each other through cellular metabolic pathways. If asparagine is needed, cells may increase their utilization of aspartate and glutamate to synthesize supplemental asparagine. Higher intracellular/extracellular concentrations of aspartate, glutamate and glutamine may indicate that the cells have enough intracellular asparagine to support cellular needs. However, decreases in concentrations of aspartate, glutamate, and glutamine could indicate asparagine limitations.

Asparagine Related Amino Acids as Surrogate Markers for Asparagine Sequence Variants (SV)

In other aspects, it has been found that asparagine related amino acids, including aspartate (Asp), glutamate (Glu), and glutamine (Gln) can be used as surrogate markers of asparagine sequence variants formed during production of polypeptides of interest. In accordance with certain embodiments of the disclosure, it has been found that intracellular and extracellular concentrations of asparagine related amino acids can serve as qualitative indicators of the formation of asparagine sequence variants.

Without intending to be limited by theory, higher levels of intracellular and/or extracellular concentrations of asparagine related amino acids will generally indicate that cells have adequate intracellular asparagine to support cellular needs. Such adequate intracellular asparagine will lead to minimal asparagine sequence variants in the produced polypeptide of interest. Conversely, lower levels of intracellular and/or extracellular concentrations of asparagine related amino acids will generally indicate that cells have inadequate intracellular asparagine to support cellular needs. Such inadequate intracellular asparagine will lead to increased asparagine sequence variants in the produced polypeptide of interest. As such, asparagine related amino acids can be used as surrogate markers of asparagine sequence variants based on a general inverse correlation. The strength of correlation of these surrogates depends on the impact of targeted asparagine supplementation on extracellular and intracellular amino acid profiles of related amino acids, which in turn may be dictated in part by cell line and asparagine concentration.

In certain embodiments, intracellular and extracellular asparagine and asparagine related amino acid concentrations may be used as surrogate markers for asparagine sequence variants. Without intending to be limited, it has been unexpectedly found that asparagine SVs may be particularly minimized by supplementing sufficient asparagine in early stage fed-batch cell culture, and formation of asparagine SVs may be monitored using intracellular and extracellular asparagine and asparagine related amino acid concentrations. By way of example, formation of asparagine SVs may be monitored in situ by monitoring intracellular or extracellular concentrations of asparagine or asparagine related amino acids. In certain embodiments, extracellular asparagine (Asn) may be monitored in early stage fed-batch cell culture as a surrogate of asparagine SVs, while extracellular asparagine (Asn), aspartate (Asp), glutamate (Glu), and glutamine (Gln) may be monitored in late stage fed-batch cell culture. In alternative embodiments, intracellular Asn, Asp, Glu, and Gln may be monitored in late stage fed-batch cell culture.

In certain embodiments, methods for detecting, measuring, or screening for asparagine sequence variants in a polypeptide of interest are provided. The methods generally comprise propagating or maintaining eukaryotic cells in a defined cell culture medium; expressing a recombinant protein of interest from the eukaryotic cells; measuring intracellular and/or extracellular concentrations of asparagine or one or more asparagine related amino acids in the defined cell culture medium; and correlating the measured concentrations of asparagine or one or more asparagine related amino acids to the presence of asparagine sequence variants present in the expressed recombinant protein of interest. In some embodiments, the measured concentrations of asparagine or the one or more asparagine related amino acids is inversely correlated to the presence of asparagine sequence variants.

In certain embodiments, the defined cell culture medium may be supplemented with asparagine, as described herein. In certain embodiments, the asparagine related amino acid may be selected from aspartate (Asp), glutamate (Glu), glutamine (Gln), and combinations thereof. In some embodiments, the asparagine related amino acid is glutamate. In some embodiments, the asparagine related amino acid may be measured intracellularly.

In some embodiments, the one or more asparagine related amino acids may be measured during late fed-batch cell culture, e.g., after day 5, after day 6, after day 7, after day 8, after day 9, after day 10, etc. of the fed-batch cell culture.

In certain aspects, the methods for detecting, measuring, or screening for asparagine sequence variants using asparagine related amino acids as surrogate markers may provide high throughput screening and optimization techniques for identifying optimal cell culture parameters for particular polypeptides of interest. For example, the method may be used to target optimal asparagine feed levels that minimize asparagine sequence variants for a particular polypeptide of interest.

Optimization of Asparagine Supplementation, In-Situ Monitoring and Control

In certain embodiments, methods for monitoring and controlling cell culture parameters, including asparagine supplementation are provided. Such methods may monitor and control various cell culture process parameters to provide optimal asparagine supplementation for a target cell line and/or polypeptide of interest. Exemplary cell culture process parameters that may be monitored and controlled include, but are not limited to, asparagine concentrations, asparagine related amino acid concentrations, viable cell count, dead cell count, protein titer, ammonium ions, alanine, osmolality, and combinations thereof.

In certain aspects, the monitoring and control methods of the disclosure may be used to optimize and prevent asparagine depletion in the cell culture medium while simultaneously controlling the formation of cell culture byproducts, such as ammonium ions and alanine. Such monitoring and control can thereby provide improved control of cell culture performance parameters, e.g., viable cell count and protein titer.

In certain embodiments, a method for monitoring and controlling cell culture medium conditions is provided. The method may generally comprise measuring one or more cell culture parameters in a cell culture using in situ freezing point depression, electrochemistry, digital imaging, photometry, bioprocess analyzer, or Raman spectroscopy; comparing the measured one or more cell culture parameters to a predetermined set point value for the cell culture parameter to determine if the one or more cell culture parameters are within a predetermined threshold range; and adjusting one or more of the cell culture parameters if a cell culture parameter is determined to be out of the predetermined threshold range. In certain embodiments, ammonium ion concentrations may be monitored and if it is determined that ammonium ion concentrations are outside of a predetermined threshold range for the particular cell culture, asparagine supplement feed may be adjusted such that the cell culture produces less ammonium while still receiving adequate asparagine. Such a method may be used to provide the optimal and maximal amount of asparagine supplementation, while minimizing the production of cellular by-products such as ammonium ion and alanine.

In certain embodiments, the monitoring and control methods of the disclosure may utilize in situ freezing point depression, electrochemistry, digital imaging, photometry, bioprocess analyzer, or Raman spectroscopy or other suitable in situ cell culture parameter measurement methodology and chemometric modeling techniques for real-time assessment of cell culture parameters, combined with signal processing techniques, for precise and continuous feedback and model predictive control of cell culture process parameters. In situ freezing point depression, electrochemistry, digital imaging, photometry, bioprocess analyzer, or Raman spectroscopy of bioreactor contents allows for the analysis of one or more process variables without having to physically remove a sample for testing. Such techniques can provide for real-time feed-back control of cell culture process parameters, including asparagine supplementation.

In one embodiment, a predetermined maximum set point value for ammonium ion and/or alanine may be set. Likewise, a predetermined set point value for asparagine supplementation continuous flow rate may be set. At the desired point during the fed-batch cell culture (e.g., early stage fed-batch time frame, day 1, day 2, day 3, day 4, late stage fed-batch timeframe, day 5, day 6, day 7, day 8, day 9, day 10, etc.) the continuous feed asparagine supplementation may be started. One or more of the concentrations of asparagine, an asparagine related amino acid, ammonium ion and/or alanine may be monitored during cell culture operations by freezing point depression, electrochemistry, digital imaging, photometry, bioprocess analyzer, or Raman spectroscopy. In certain embodiments, to ensure that the raw spectral data is continuously up to date, the data from the freezing point depression, electrochemistry, digital imaging, photometry, bioprocess analyzer, or Raman spectroscopy may be acquired about every 10 minutes to 2 hours. In another embodiment, the data may be acquired about every 15 minutes to 1 hour. In still another embodiment, the data may be acquired about every 20 minutes to 30 minutes.

The monitoring of the one or more cell culture process parameters may be analyzed by any commercially available analyzers that allows for in situ analysis. The in situ analyzer should be capable of obtaining raw data within the cell culture (for example, the analyzer should be equipped with a probe that may be inserted into the bioreactor). Suitable analyzers include, but are not limited to, RamanRXN2 and RamanRXN4 analyzers (Kaiser Optical Systems, Inc. Ann Arbor, Mich.) or in BioProfile Flex automated cell culture analyzer.

The raw spectral data obtained by the in situ analyzer may be compared to offline measurements of the particular process parameter to be monitored or controlled (for example, offline asparagine concentration measurements) in order to correlate the data within the process parameter. The offline measurement data may be collected through any appropriate analytical method. Additionally, any type of multivariate software package, for example, SIMCA 13 (MKS Data Analytic Solutions, Umea, Sweden), may be used to correlate the data to offline measurements of the particular process variable to be monitored or controlled. However, in some embodiments, it may be necessary to pretreat the raw data with filters to remove any varying baselines. For example, the raw data may be pretreated with any type of point smoothing technique or normalization technique. Normalization may be needed, e.g., to correct for any power variation and exposure time. In one embodiment, the raw data may be treated with point smoothing, such as 1st derivative with 21 $cm^{-1}$ point smoothing, and normalization, such as Standard Normal Variate (SNV) normalization.

Chemometric modeling may also be performed on the obtained spectral data. In certain embodiments, one or more multivariate methods including, but not limited to, Partial Least Squares (PLS), Principal Component Analysis (PCA), Orthogonal Partial least squares (OPLS), Multivariate Regression, Canonical Correlation, Factor Analysis, Cluster Analysis, Graphical Procedures, and the like, can be used on the spectral data. In one embodiment, the obtained spectral data is used to create a PLS regression model. A PLS regression model may be created by projecting predicted variables and observed variables to a new space. In this aspect, a PLS regression model may be created using the measurement values obtained from the Raman analysis and the offline measurement values. The PLS regression model provides predicted process values, for example, predicted nutrient concentration values.

After chemometric modeling, a signal processing technique may be applied to the predicted process values (for example, the predicted asparagine concentration values). In one embodiment, the signal processing technique includes a noise reduction technique. In certain embodiments, one or more noise reduction techniques may be applied to the predicted process parameters. Any noise reduction technique known to those skilled in the art may be utilized. For example, the noise reduction technique may include data smoothing and/or signal rejection. Smoothing is achieved through a series of smoothing algorithms and filters while signal rejection uses signal characteristics to identify data that should not be included in the analyzed spectral data. In one embodiment, the predicted process values are noise mitigated by a noise reduction filter. The noise reduction filter provides final filtered process values (for example, final filtered nutrient concentration values). In this aspect, the noise reduction technique combines raw measurements with a model-based estimate for what the measurement should yield according to the model. In one embodiment, the noise reduction technique combines a current predicted process value with its uncertainties. Uncertainties can be determined by the repeatability of the predicted process values and the current process conditions. Once the next predicted process value is observed, the estimate of the predicted process value (for example, predicted nutrient concentration value) is updated using a weighted average where more weight is given to the estimates with higher certainty. Using an iterative approach, the final process values may be updated based on the previous measurement and the current process conditions. In this aspect, the algorithm should be recursive and able to run in real time so as to utilize the current predicted process value, the previous value, and experimentally determined constants. The noise reduction technique improves the robustness of the measurements received from the Raman analysis and the PLS predictions by reducing noise upon which the automated feedback controller will act.

Upon obtaining the final filtered process values (for example, the final filtered nutrient concentration values), the final values may be sent to an automated feedback controller. The automated feedback controller may be used to control and maintain the process parameters (for example, monitoring of the ammonium concentration and control of the asparagine concentration) at or below the predefined set point. In one embodiment, if ammonium concentrations are detected that are above the maximum set point value, the automated feedback controller may be prompted to reduce the amount of asparagine feed within a threshold range. The automated feedback controller may include any type of controller that is able to calculate an error value as the difference between a desired set point (e.g., the predefined set point) and a measured process parameter and automatically apply an accurate and responsive correction. The automated feedback controller should also have controls that are capable of being changed in real time from a platform interface. For instance, the automated feedback controller should have a user interface that allows for the adjustment of a predefined set point. The automated feedback controller should be capable of responding to a change in the predefined set point.

In one embodiment, the automated feedback controller may be a proportional-integral-derivative (PID) controller. In this aspect, the PID controller is operable to calculate the difference between the predefined set point and the measured process variable (for example, the measured asparagine concentration) and automatically apply an accurate correction. For example, when a nutrient concentration of a cell culture is to be controlled, the PID controller may be operable to calculate a difference between a filtered nutrient value and a predefined set point and provide a correction in nutrient amount. In this aspect, the PID controller may be operatively connected to a nutrient pump on the bioreactor so that the corrective nutrient amount may be pumped into the bioreactor.

Through the use of real time analysis and feedback control, the methods of the disclosure are able to provide optimal asparagine supplementation for a target cell line and/or polypeptide of interest. That is, the method of the present invention is able to provide optimal asparagine supplementation to a cell culture, while minimizing the production of cell culture by-products, including harmful cell culture by-products.

Cell Culture Medium

The terms "cell culture medium" and "culture medium" refer to a nutrient solution used for growing cells, e.g., eukaryotic cells, that typically provides the necessary nutrients to enhance growth of the cells, such as a carbohydrate energy source, essential (e.g. phenylalanine, valine, threonine, tryptophan, methionine, leucine, isoleucine, lysine, and histidine) and nonessential (e.g. alanine, asparagine, aspartic acid, cysteine, glutamic acid, glutamine, glycine, proline, serine, and tyrosine) amino acids, trace elements, energy sources, lipids, vitamins, etc. Cell culture medium may contain extracts, e.g. serum or peptones (hydrolysates), which supply raw materials that support cell growth. Media may contain yeast-derived or soy extracts, instead of animal-derived extracts. Chemically defined medium refers to a cell culture medium in which all of the chemical components are known (i.e. have a known chemical structure). Generally, chemically defined medium is free of animal-derived components, such as serum- or animal-derived peptones and yeast and soy extracts. In one embodiment, the medium is a chemically defined medium.

The medium may also contain components that enhance growth and/or survival above the minimal rate, including hormones and growth factors. The medium is preferably formulated to a pH and salt concentration optimal for cell survival and proliferation.

In certain aspects, the cell culture medium may be serum-free. "Serum-free" applies to a cell culture medium that does not contain animal sera, such as fetal bovine serum. The serum-free media may contain ≤16 g/L of hydrolysates, such as soy hydrolysate. The present disclosure also provides chemically defined media, which is not only serum-free, but also hydrolysate-free. "Hydrolysate-free" applies to cell culture media that contains no exogenous protein hydrolysates such as animal or plant protein hydrolysates such, for example peptones, tryptones and the like.

"Base medium" is the initial medium (e.g., present in the seed train and/or at day 0 of the cell culture production) in which the cells are propagated and contains all the necessary nutrients, which includes a base mixture of amino acids. Various recipes (i.e. formulations) for base media may be manufactured or purchased in commercially available lots. Likewise "base feed medium" contains mixtures of supplemental nutrients that are commonly consumed during a production culture and are utilized in a feeding strategy (for a so-called "fed-batch" culture). Varieties of base feed media are commercially available. A "feed" includes scheduled additions or additions to media at regular intervals, such as according to a protocol, including a continuous feed culture system, as in a chemostat (see C. Altamirano et al., *Biotechnol Prog.* 2001 November-December; 17(6):1032-41), or according to a fed-batch process (Y. M. Huang et al., *Biotechnol Prog.* 2010 September-October; 26(5): 1400-10). For example, a culture may be fed once per day, every other day, every three days, or may be fed when the concentration of a specific medium component, which is being monitored, falls outside a desired range.

Without intending to be limited, the disclosure may be practiced with any one or more of a variety of base media or combinations thereof. Base media are generally known in the art and include inter alia Eagle's MEME (minimal essential media) (Eagle, *Science*, 1955, 112(3168):501-504), Ham's F12 (Ham, *Proc. Nat'l. Acad. Sci. USA*, 1965, 53:288-293), F-12 K medium, Dulbecco's medium, Dulbecco's Modified Eagle Medium (*Proc. Natl. Acad. Sci. USA*, 1952 August; 38(8): 747-752), DMEM/Ham's F12 1:1, Trowell's T8, A2 media (Holmes and Wolf, *Biophys. Biochem. Cytol.*, 1961, 10:389-401), Waymouth media (Davidson and Waymouth, *Biochem. J*, 1945, 39(2):188-199), Williams E media (William's et al., *Exp. Cell Res.*, 1971, 69:105 et seq.), RPMI 1640 (Moore et al., *J Amer. Med. Assoc.*, 1967, 199:519-524), MCDB 104/110 media (Bettger et al., *Proc. Nat'l. Acad. Sci. USA*, 1981, 78(9):5588-5592), Ventrex HL-1 media, albumin-globulin media (Orr et al., *Appl. Microbiol.*, 1973, 25(1):49-54), RPMI-1640 Medium, RPMI-1641 Medium, Iscove's Modified Dulbecco's Medium, McCoy's 5 A Medium, Leibovitz's L-15 Medium, and serum-free media such as EX-CELL™ 300 Series (JRH Biosciences, Lenexa, Kans.), protamine-zinc-insulin media (Weiss et al., 1974, U.S. Pat. No. 4,072,565), biotin-folate media (Cartaya, 1978, U.S. Re30,985), Transferrin-fatty acid media (Baker, 1982, U.S. Pat. No. 4,560,655), transferrin-EGF media (Hasegawa, 1982, U.S. Pat. No. 4,615,977; Chessebeuf, 1984, U.S. Pat. No. 4,786,599), and other media permutations (see Inlow, U.S. Pat. No. 6,048,728; Drapeau, U.S. Pat. No. 7,294,484; Mather, U.S. Pat. No. 5,122,469; Furukawa, U.S. Pat. No. 5,976,833; Chen, U.S. Pat. No. 6,180,401; Chen, U.S. Pat. No. 5,856,179; Etcheverry, U.S. Pat. No. 5,705,364; Etcheverry, U.S. Pat. No. 7,666,416; Ryll, U.S. Pat. No. 6,528,286; Singh, U.S. Pat. No. 6,924,124; Luan, U.S. Pat. No. 7,429,491; and the like).

The cell culture medium may also be fed periodically (as in so-called "fed-batch" cultures), with or without additional ingredients such as polyamines or increased concentrations of components like amino acids, salts, sugars, vitamins, hormones, growth factors, buffers, antibiotics, lipids, trace elements and the like, depending on the requirements of the cells to be cultured or the desired cell culture parameters.

In certain aspects, the cell culture medium may be depleted of amino acids over the course of the recombinant protein production, where no additional amino acid supplementation is provided, or the cell culture medium may be "non-depleted", where amino acid supplementation is provided for the depleted amino acids (as described below).

In one embodiment, the medium additionally contains 100 µM±15 µM ornithine, or 300 µM±45 µM ornithine, or 600 µM±90 µM omithine, or even 900 µM±135 µM ornithine. In another embodiment, the medium contains at least about 29 µM±1 µM ornithine, or at least about, 59 µM±12 µM omithine, 80 µM±13 µM omithine, or at least about 296 µM±44 µM ornithine, or at least about 593 µM±89 µM omithine, or at least about 889 µM±133 µM ornithine.

Putrescine may optionally be added to the supplemented media. Putrescine has been included, at low concentrations, e.g., 0.01-120 mg/L, as a component in some cell culture media formulations; see for example WO 2005/028626, which describes 0.02-0.08 mg/L putrescine; U.S. Pat. No. 5,426,699 (0.08 mg/L); U.S. Pat. No. RE30,985 (0.16 mg/L); U.S. Pat. No. 5,811,299 (0.27 mg/L); U.S. Pat. No. 5,122,469 (0.5635 mg/L); U.S. Pat. No. 5,063,157 (1 mg/L); WO 2008/154014 (~100 µM-~1000 µM); US Pat. App. No. 2007/0212770 (0.5-30 mg/L polyamine; 2 mg/L putrescine; 2 mg/L putrescine+2 mg/L ornithine; 2 mg/L putrescine+10 mg/L omithine).

In some embodiments, the cell culture medium is further supplemented with a combination of ornithine and putrescine, wherein the putrescine can be at a concentration of at least about 150 to 720 µM. In some embodiments, the media is further supplemented with putrescine at a concentration of about 170 to 230 µM. In one embodiment, the medium contains 200 µM±30 µM putrescine in addition to ≥90 µM±15 µM omithine. In one embodiment, the medium contains ≤186 µM±28 µM putrescine in addition to ≤89 µM±13 µM omithine. In another embodiment, the medium contains ≥186 µM±28 µM putrescine in addition to ≥89 µM±13 µM omithine. (See International Publication No. WO2014/144198A1, published on Sep. 18, 2014, which is herein incorporated by reference in its entirety.)

In still other embodiments, ornithine is present in the medium at a concentration ranging from 0.09±0.014 mM to 0.9±0.14 mM, such as 0.09±0.014 mM, 0.3±0.05 mM, 0.6±0.09 mM, or 0.9±0.14 mM ornithine. In some embodiments, the medium also contains at least 0.20±0.03 mM putrescine. In some embodiments, the additional putrescine is at a concentration ranging from 0.20±0.03 mM to 0.714±0.11 mM, such as 0.20±0.03 mM, 0.35±0.06, or 0.714±0.11 mM putrescine.

The still other embodiments, the medium may be supplemented with taurine at a concentration (expressed in millimoles per liter) of at least about 0.1, 0.2, 0.3, 0.4, 0.5, 0.6, 0.7, 0.8, 0.9, 1, 2, 3, 4, 5, 6, 7, 8, 9 or 10 mM.

Various other supplements may be added to the culture medium, and are within the skill of the person in the art to determine additionally appropriate conditions. In certain embodiments, the supplement may be an asparagine supplement as described herein. In some embodiments, the medium is supplemented with a mixture of amino acids selected from the group consisting of aspartic acid, cysteine, glutamic acid, glycine, lysine, phenylalanine, proline, serine, threonine, valine, arginine, histidine, asparagine, glutamine, alanine, isoleucine, leucine, methionine, tyrosine, and tryptophan, in order to be non-depleted or as supplemental nutrients are needed (i.e., bulk feed).

In one embodiment, the media is further supplemented with about 170 µM to 175 µM nucleosides. In one embodiment, the media contains purine derivatives in a cumulative concentration of at least 40 µM, at least 45 µM, at least 50 µM, at least 55 µM, at least 60 µM, at least 65 µM, at least 70 µM, at least 75 µM, at least 80 µM, at least 85 µM, at least 90 µM, at least 95 µM, at least 100 µM, or at least 105 µM. In one embodiment, the media contains about 100 µM to 110 µM of purine derivatives. Purine derivatives include hypoxanthine and the nucleosides adenosine and guanosine. In one embodiment, the media contains pyrimidine derivatives in a cumulative concentration of at least 30 µM, at least 35 µM, at least 40 µM, at least 45 µM, at least 50 µM, at least 55 µM, at least 60 µM, or at least 65 µM. In one embodiment, the media contains about 65 µM to 75 µM of pyrimidine derivatives. Pyrimidine derivatives include the nucleosides thymidine, uridine, and cytidine. In one particular embodiment, the media contains adenosine, guanosine, cytidine, uridine, thymidine and hypoxanthine.

In addition to the inclusion of any of the above additives, in one embodiment, the media is further supplemented with micromolar amounts of fatty acids (or fatty acid derivatives) and tocopherol. In one embodiment, the fatty acids include any one or more of linoleic acid, linolenic acid, thioctic acid, oleic acid, palmitic acid, stearic acid, arachidic acid, arachidonic acid, lauric acid, behenic acid, decanoic acid, dodecanoic acid, hexanoic acid, lignoceric acid, myristic acid, and octanoic acid. In one embodiment, the media contains tocopherol, linoleic acid, and thioctic acid.

In one embodiment, the media also may be further supplemented with a mixture of vitamins, which includes other nutrients and essential nutrients, at a cumulative concentration of at least about 700 µM or at least about 2 mM. In one embodiment, the mixture of vitamins contains one or more of D-biotin, choline chloride, folic acid, myo-inositol, niacinamide, pyridoxine HCl, D-pantothenic acid (hemiCa), riboflavin, thiamine HCl, vitamin B12, and the like. In one embodiment, the mixture of vitamins includes all of D-biotin, choline chloride, folic acid, myo-inositol, niacinamide, pyridoxine HCl, D-pantothenic acid (hemiCa), riboflavin, thiamine HCl, and vitamin B12.

In a particular embodiment, the cell culture media may be chemically defined, and may comprise: amino acid mixtures as discussed herein, $CaCl_2 \cdot 2H_2O$; KCl; $MgSO_4$; NaCl; $Na_2HPO_4$ or other phosphate salts; pyruvate; D-biotin; choline chloride; folic acid; myo-inositol; niacinamide; pyridoxine HCl; D-pantothenic acid; riboflavin; thiamine HCl; vitamin B12; ρ-aminobenzoic acid; ethanolamine HCl; poloxamer 188; DL-a-tocopherol phosphate; linoleic acid; $Na_2SeO_3$; thioctic acid; one or more buffers, and glucose; and optionally adenosine; guanosine; cytidine; uridine; thymidine; and hypoxanthine 2Na.

In one embodiment, the starting osmolarity of the media of the disclosure is 200-500, 250-400, 275-350, or about 300 mOsm. During growth of the cells in the media of the disclosure, and in particular following any feedings according to a fed-batch protocol, the osmolarity of the culture may increase up to about 350, 400, 450, 500 or up to about 550 mOsm.

In some embodiments wherein the osmolarity of the medium is less than about 300, the osmolarity may be adjusted to about 300 with the addition of one or more salts in excess of the amount specified. In one embodiment, osmolarity is increased to a desired level by adding one or more of an osmolyte selected from sodium chloride, potassium chloride, a magnesium salt, a calcium salt, an amino acid salt, a salt of a fatty acid, sodium bicarbonate, sodium carbonate, potassium carbonate, a chelator that is a salt, a sugar (e.g., galactose, glucose, sucrose, fructose, fucose, etc.), and a combination thereof. In one embodiment, the osmolyte is added over and above its concentration in a component already present in the defined medium (e.g., a sugar is added over and above the concentration specified for a sugar component).

Cell Culture

One aspect of the disclosure provides a cell culture comprising a cell line expressing a recombinant protein of interest in cultured with asparagine supplements, as described herein. Examples of cell lines that are routinely used to produce recombinant proteins include, inter alia, primary cells, BSC cells, HeLa cells, HepG2 cells, LLC-MK cells, CV-1 cells, COS cells, VERO cells, MDBK cells, MDCK cells, CRFK cells, RAF cells, RK cells, TCMK-1 cells, LLCPK cells, PK15 cells, LLC-RK cells, MDOK cells, BHK cells, BHK-21 cells, CHO cells, CHO-K1 cells, NS-1 cells, MRC-5 cells, WI-38 cells, 3T3 cells, 293 cells, Per.C6 cells and chicken embryo cells. In one embodiment, the cell line is a CHO cell line or one or more of several specific CHO cell variants optimized for large-scale protein production, e.g., CHO-K1.

Another aspect of the disclosure relates to a methods of culturing cells using the asparagine supplements as described herein, wherein the use of such asparagine supplements enhances the growth of eukaryotic cells while improving the titer of one or more recombinant proteins of interest by such cells and maintaining cell viability, in particular by use in the early fed-batch cell culture and/or late stage fed-batch cell culture, as compared to a similar method with a lower amount of asparagine supplementation in early and/or late fed-batch cell culture.

In some aspects, recombinant protein titer is improved relative to cells grown with a lower amount of asparagine supplementation in early and/or late fed-batch cell culture. In some embodiments, the protein titer yielded from cell culture grown with a lower amount of asparagine supplementation in early and/or late fed-batch cell culture is at least about 4%, at least about 5%, at least about 6%, at least about 7%, at least about 8%, at least about 9%, at least about 10%, at least about 110, at least about 12%, at least about 13%, at least about 14%, at least about 15%, at least about 16%, at least about 17%, at least about 18%, at least about 19%, at least about 20%, at least about 21%, at least about 22% greater, at least about 23% greater, at least about 24% greater, at least about 25% greater, at least about 26% greater, at least about 27% greater, at least about 28% greater or at least about 29% greater than the protein titer (yield) from cells cultured with a lower amount of asparagine supplementation in early and/or late fed-batch cell culture. In some embodiments, the protein titer yielded form cell cultures with asparagine supplements of the disclosure is greater than that of similar or identical cells cultured with a lower amount of asparagine supplementation in early and/or late fed-batch cell culture.

In some aspects, cell growth (e.g., doubling rate), viable cell density, cell viability, and combinations thereof, are improved relative to cells grown with a lower amount of asparagine supplementation in early and/or late fed-batch cell culture.

In some embodiments, the doubling rate of viable cells cultured with asparagine supplements of the disclosure is at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 35%, at least 40%, at least 45%, at least 50%, at least 55%, at least 60%, at least 70%, at least 80%, at least 90%, at least 100%, or at least 3-fold greater than the doubling rate of cells cultured with a lower amount of asparagine supplementation in early and/or late fed-batch cell culture. In some embodiments, the doubling rate of viable cells cultured with asparagine supplements of the disclosure is about 10%, 11%, 12%, 13%, 14%, 15%, 16%, 17%, 18%, 19%, 20%, 21%, 22%, 23%, 24%, 25%, 26%, 27%, 28%, 29%, or 30% greater than the doubling rate of viable cells cultured with a lower amount of asparagine supplementation in early and/or late fed-batch cell culture.

In some embodiments, the doubling time of actively cycling mammalian cells is less than 30 hours, less than 29 hours, less than 28 hours, less than 27 hours, less than 26 hours, less than 25 hours, less than 24 hours, less than 23 hours, less than 22 hours, less than 21 hours, less than 20 hours, less than 19 hours, or less than 18 hours when cultured with asparagine supplements of the disclosure, as compared to cell cultured with a lower amount of asparagine supplementation in early and/or late fed-batch cell culture. In some embodiments, the doubling time of actively growing mammalian cells is less than 28 hours when cultured with asparagine supplements of the disclosure, as compared to cell cultured with a lower amount of asparagine supplementation in early and/or late fed-batch cell culture. In some embodiments, the doubling time of mammalian cells is about 27±1 hours, about 26±1 hours, about 25±1 hours, about 24±1 hours, about 23±1 hours, about 22±1 hours, or about 21±1 hours when cultured with asparagine supplements of the disclosure, as compared to cell cultured with a lower amount of asparagine supplementation in early and/or late fed-batch cell culture. In some embodiments, the doubling time of actively cycling mammalian cells is about 24±1 hours when cultured with asparagine supplements of the disclosure, as compared to cells cultured with a lower amount of asparagine supplementation in early and/or late fed-batch cell culture. In some embodiments, the doubling time of actively dividing cells when cultured with asparagine supplements of the disclosure is at least 15%, at least 16%, at least 17%, at least 18%, at least 19%, at least 20%, or at least 25% shorter than the doubling time of actively cycling cells cultured with a lower amount of asparagine supplementation in early and/or late fed-batch cell culture.

Regarding cell viability, cells cultured with asparagine supplements of the disclosure show a viability that is at least 10%, at least 15%, at least 20%, at least 25%, at least 30%, at least 35%, at least 40%, at least 45%, at least 50%, at least, 55%, at least 60%, at least 65%, at least 70%, at least 75%, at least 80%, at least 85%, at least 90%, at least 95%, at least 99%, at least 100%, or at least 3-fold greater than the viability of cells cultured with a lower amount of asparagine supplementation in early and/or late fed-batch cell culture.

In the production culturing vessel or bioreactor, a basal culture medium and cells are supplied to a culturing vessel following a seed culture or growth phase. In certain embodiments, the cell supernatant or cell lysate is harvested following the production culture. In other embodiments, the polypeptide or protein of interest is recovered from the culture medium or cell lysate, or whatever the case may be depending on the location of the protein of interest, using techniques well known in the art A "cell line" refers to a cell or cells that are derived from a particular lineage through serial passaging or subculturing of cells. The term "cells" is used interchangeably with "cell population".

The term "cell" includes any cell that is suitable for expressing a recombinant nucleic acid sequence. Cells include those of eukaryotes, such as non-human animal cells, mammalian cells, human cells, avian cells, insect cells, yeast cells, or cell fusions such as, for example, hybridomas or quadromas. In certain embodiments, the cell is a human, monkey, ape, hamster, rat or mouse cell. In other embodiments, the cell is selected from the following cells: CHO (e.g. CHO K1, DXB-11 CHO, Veggie-CHO), COS (e.g. COS-7), retinal cell, Vero, CV1, kidney (e.g. HEK293, 293 EBNA, MSR 293, MDCK, HaK, BHK21), HeLa, HepG2, WI38, MRC 5, Colo25, HB 8065, HL-60, lymphocyte, e.g. Jurkat (T lymphocyte) or Daudi (B lymphocyte), A431 (epidermal), CV-1, U937, 3T3, L cell, C127 cell, SP2/0, NS-0, MMT cell, stem cell, tumor cell, and a cell line derived from an aforementioned cell. In some embodiments, the cell comprises one or more viral genes, e.g. a retinal cell that expresses a viral gene (e.g. a PER.C6® cell). In some embodiments, the cell is a CHO cell. In other embodiments, the cell is a CHO K1 cell.

In the recombinant protein production phase, a "fed-batch cell culture" or "fed-batch culture" refers to a batch culture wherein the animal cells and culture medium are supplied to the culturing vessel initially and additional culture nutrients are slowly fed, continuously or in discrete increments, to the culture during culturing, with or without periodic cell and/or product harvest before termination of culture. Fed-batch culture includes "semi-continuous fed-batch culture" wherein periodically whole culture (which may include cells and medium) is removed and replaced by fresh medium. Fed-batch culture is distinguished from simple "batch culture" whereas all components for cell culturing (including the animal cells and all culture nutrients) are supplied to the culturing vessel at the start of the culturing process in batch culture. Fed-batch culture can be further distinguished from perfusion culturing insofar as the supernatant is not removed from the culturing vessel during the process, whereas in perfusion culturing, the cells are restrained in the culture by, e.g., filtration, and the culture medium is continuously or intermittently introduced and removed from the culturing vessel. However, removal of samples for testing purposes during fed-batch cell culture is contemplated. The fed-batch process continues until it is determined that maximum working volume and/or protein production is reached.

The phrase "continuous cell culture" when used herein relates to a technique used to grow cells continually, usually in a particular growth phase. For example, if a constant supply of cells is required, or the production of a particular polypeptide or protein of interest is required, the cell culture may require maintenance in a particular phase of growth. Thus, the conditions must be continually monitored and adjusted accordingly in order to maintain the cells in that particular phase.

One aspect of the disclosure relates to a fed-batch, production cell culture in which protein is produced and harvested. Prior to production phase, there is typically a growth phase (also known as a seed train or seed culture) wherein all components for cell culturing are supplied to the culturing vessel at the start of the culturing process then cell population is expanded until ready for production scale. As such, the culturing vessel is inoculated with cells at a suitable seeding density for the initial cell growth phase depending on the starting cell line. In some aspects, the asparagine supplements of the disclosure may be used with a fed-batch production cell culture, as further described herein.

Culturing vessels include, but are not limited to well plates, T-flasks, shake flasks, stirred vessels, spinner flasks, hollow fiber, air lift bioreactors, and the like. A suitable cell culturing vessel is a bioreactor. A bioreactor refers to any culturing vessel that is manufactured or engineered to manipulate or control environmental conditions. Such culturing vessels are well known in the art.

Bioreactor processes and systems have been developed to optimize gas exchange, to supply sufficient oxygen to sustain cell growth and productivity, and to remove $CO_2$. Maintaining the efficiency of gas exchange is an important criterion for ensuring successful scale up of cell culture and protein production. Such systems are well-known to the person having skill in the art.

In one embodiment, the media is supplemented at intervals during cell culture according to a fed-batch process. Fed-batch culturing is generally known in the art and employed to optimize protein production (see Y. M. Huang et al., *Biotechnol Prog.* 2010 September-October; 26(5): 1400-10). Fed-batch processes are typically used during the production phase.

Supplemental feed may be performed to include additional nutrients, such as vitamins, amino acids and other nutrients as described hereinabove, at intervals at a frequency of every day, or every 2-3 days, for the duration of the production culture. Supplemented feed may be performed (supplemented media containing nutrients are added) at least 2 times, or at least 8 times, throughout the duration of the production culture for a 2 week or more culture. In another embodiment, the supplemental feed could be performed on each day for the duration of the culture. Alternative culture feeding schedules are also envisioned.

Additional amino acid supplementation may also be performed to provide a non-depleted medium, wherein depleted amino acids are determined according to methods known in the art and described herein. When this regime is employed, additional amino acids are supplemented or added at intervals, preferably at a frequency of every day, or every 2-3 days, for the duration of the production culture, depending on the determination of amino acid depletion. In one embodiment, the mixture of additional amino acids to maintain a non-depleted cell culture medium is added to the culture on or about day 1, on or about day 2, on or about day 3, on or about day 4, on or about day 5, on or about day 6, on or about day 7, on or about day 8, on or about day 9, on or about day 10, on or about day 11, on or about day 12, on or about day 13, and on or about day 14, for a 2 week or more culture. Alternative culture feeding schedules are also envisioned.

Eukaryotic ells, such as CHO cells, may be cultured in small scale cultures, such as in 125 ml containers having about 25 mL of media, 250 mL containers having about 50 to 100 mL of media, 250 mL containers having about 150 to 240 mL of media, 500 mL containers having about 100 to 200 mL of media. Alternatively, the cultures can be large scale such as for example 1000 mL containers having about 300 to 1000 mL of media, 3000 mL containers having about 500 mL to 3000 mL of media, 8000 mL containers having about 2000 mL to 8000 mL of media, and 15000 mL containers having about 4000 mL to 15000 mL of media. Cultures for manufacturing can contain 10,000 L of media or more. Large scale cell cultures, such as for clinical manufacturing of protein therapeutics, are typically maintained for days, or even weeks, while the cells produce the desired protein(s). During this time the culture can be supplemented with a concentrated feed medium containing components, such as nutrients and amino acids, which are consumed during the course of the culture. Concentrated feed medium may be based on any cell culture media formulation. Such a concentrated feed medium can contain most of the components of the cell culture medium at, for example, about 5×, 6×, 7×, 8×, 9×, 10×, 12×, 14×, 16×, 20×, 30×, 50×, 100×, 200×, 400×, 600×, 800×, or even about 1000× of their normal useful amount. Concentrated feed media are often used in fed-batch culture processes.

In some embodiments, the cell culture may be further supplemented with "point-of-use additions", also known as additions, point-of-use ingredients, or point-of-use chemicals, during the course of cell growth or protein production. Point-of-use additions include any one or more of a growth factor or other proteins, a buffer, an energy source, a salt, an amino acid, a metal, and a chelator. Other proteins include transferrin and albumin. Growth factors, which include cytokines and chemokines, are generally known in the art and are known to stimulate cell growth, or in some cases, cellular differentiation. A growth factor is usually a protein (e.g., insulin), a small peptide, or a steroid hormone, such as estrogen, DHEA, testosterone, and the like. In some cases, a growth factor may be a non-natural chemical that promotes cell proliferation or protein production, such as e.g., tetrahydrofolate (THF), methotrexate, and the like. Non-limiting examples of protein and peptide growth factors include angiopoietins, bone morphogenetic proteins (BMPs), brain-derived neurotrophic factor (BDNF), epidermal growth factor (EGF), erythropoietin (EPO), fibroblast growth factor (FGF), glial cell line-derived neurotrophic factor (GDNF), granulocyte colony-stimulating factor (G-CSF), granulocyte macrophage colony-stimulating factor (GM-CSF), growth differentiation factor-9 (GDF9), hepatocyte growth factor (HGF), hepatoma-derived growth factor (HDGF), insulin, insulin-like growth factor (IGF), migration-stimulating factor, myostatin (GDF-8), nerve growth factor (NGF) and other neurotrophins, platelet-derived growth factor (PDGF), thrombopoietin (TPβ), transforming growth factor alpha (TGF-α), transforming growth factor beta (TGF-β), tumor necrosis factor-alpha (TNF-α), vascular endothelial growth factor (VEGF), wnt signaling pathway agonists, placental growth factor (PlGF), fetal Bovine somatotrophin (FBS), interleukin-1 (IL-1), IL-2, IL-3, IL-4, IL-5, IL-6, IL-7, and the like. In one embodiment, the cell culture media is supplemented with the point-of-use addition growth factor insulin. In one embodiment, the concentration of insulin in the media, i.e., the amount of insulin in the cell culture media after addition, is from about 0.1 μM to 10 μM.

Buffers are generally known in the art. The invention is not restricted to any particular buffer or buffers, and any one of ordinary skill in the art can select an appropriate buffer or buffer system for use with a particular cell line producing a particular protein. In one embodiment, a point-of-use addition buffer is $NaHCO_3$. In another embodiment, the buffer is HEPES. In other embodiments, the point-of-use addition buffer comprises both $NaHCO_3$ and HEPES.

Energy sources for use as a point-of-use addition in cell culture are also well known in the art. Without limitation, in one embodiment, the point-of-use addition energy source is glucose. Given the particular and specific requirements of a particular cell line and the protein to be produced, in one embodiment the glucose can be added to a concentration of about 1 to 20 mM in the media. In some cases, glucose can be added at high levels of 20 g/L or higher.

Chelators are likewise well known in the art of cell culture and protein production. Tetrasodium EDTA dehydrate and citrate are two common chelators used in the art, although other chelators may be employed in the practice of this invention. In one embodiment, a point-of-use addition chelator is tetrasodium EDTA dihydrate. In one embodiment, a point-of-use addition chelator is citrate, such as $Na_3C_6H_5O_7$.

In one embodiment, the cell culture medium may additionally be supplemented with one or more point-of-use addition amino acids as an energy source, such as e.g., glutamine. In one embodiment, the cell culture media is supplemented with the point-of-use addition glutamine at a final concentration of about 1 mM to 13 mM.

Other point-of-use additions include one or more of various metal salts, such as salts of iron, nickel, zinc and copper. In one embodiment, the cell culture media is supplemented with any one or more of copper sulfate, zinc sulfate, ferric chloride, and nickel sulfate.

Protein Production

In certain aspects, the present disclosure provides methods for improving cell culture performance, including improving recombinant protein titer in production of a recombinant protein by culturing eukaryotic cells. In some embodiments, the eukaryotic cells comprise a stably integrated nucleic acid encoding the recombinant protein. In other embodiments, the methods of the disclosure provide for improved cell growth (e.g., doubling rate), viable cell density, cell viability, and combinations thereof, In some embodiments, the methods of the disclosure include providing an asparagine supplement of the disclosure; culturing eukaryotic cells in the asparagine supplement; expressing a recombinant protein of interest from the eukaryotic cells, and producing a higher titer of the recombinant protein from the eukaryotic cells cultured in the asparagine supplement, as compared to similar or identical eukaryotic cells cultured a lower amount of asparagine supplementation or non-asparagine supplementation in an early and/or late fed-batch cell culture.

In some embodiments, the protein production yield or titer, which can be expressed in grams of protein product per liter of culture medium, from cells cultured with an asparagine supplement of the disclosure is at least 100 mg/L, at least 1 g/L, at least 1.2 g/L, at least 1.4 g/L, at least 1.6 g/L, at least 1.8 g/L, at least 2 g/L, at least 2.5 g/L, at least 3 g/L, at least, 3.5 g/L, at least 4 g/L, at least 4.5 g/L, at least 5 g/L, at least 5.5 g/L, at least 6 g/L, at least 6.5 g/L, at least 7 g/L, at least 7.5 g/L, at least 8 g/L, at least 8.5 g/L, at least 9 g/L, at least 9.5 g/L, at least 10 g/L, at least 15 g/L, or at least 20 g/L.

In some embodiments, the protein titer yielded from cells cultured with an asparagine supplement of the disclosure is at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23% greater, at least about 24% greater, at least about 25% greater, at least about 26% greater, at least about 27% greater, at least about 28% greater or at least about 29% greater than the protein titer (yield) from similar or identical cells cultured with a lower amount of asparagine supplementation or non-asparagine supplementation in early and/or late fed-batch cell culture.

In some embodiments, the titer (yield) of protein by mammalian cells cultured with asparagine supplements of the disclosure, is at least 100 mg/L, at least 0.5 g/L, at least 1 g/L, at least 1.2 g/L, at least 1.4 g/L, at least 1.6 g/L, at least 1.8 g/L, at least 2 g/L, at least 2.5 g/L greater than the titer of protein by a similar or identical cell cultured with a lower amount of asparagine supplementation or non-asparagine supplementation in early and/or late fed-batch cell culture.

The methods of the disclosure are useful for improving protein production via cell culture processes. The cell lines used in the invention can be genetically engineered to express a recombinant protein of commercial or scientific interest. Genetically engineering the cell line involves transfecting, transforming or transducing the cells with a recombinant polynucleotide molecule, or otherwise altering (e.g., by homologous recombination and gene activation or fusion of a recombinant cell with a non-recombinant cell) so as to cause the host cell to express a desired recombinant polypeptide. Methods and vectors for genetically engineering cells or cell lines to express a polypeptide of interest are well known to those of skill in the art; for example, various techniques are illustrated in Current Protocols in Molecular Biology. Ausubel et al., eds. (Wiley & Sons, New York, 1988, and quarterly updates); Sambrook et al., Molecular Cloning: A Laboratory Manual (Cold Spring Laboratory Press, 1989); Kaufman, R. J., *Large Scale Mammalian Cell Culture,* 1990, pp. 15-69. A wide variety of cell lines suitable for growth in culture are available from the American Type Culture Collection (Manassas, Va.) and commercial vendors.

In some embodiments, the protein product (protein of interest) is an antibody, a human antibody, a humanized antibody, a chimeric antibody, a monoclonal antibody, a multispecific antibody, a bispecific antibody, an antigen binding antibody fragment, a single chain antibody, a diabody, triabody or tetrabody, a Fab fragment or a F(ab')2 fragment, an IgD antibody, an IgE antibody, an IgM antibody, an IgG antibody, an IgG1 antibody, an IgG2 antibody, an IgG3 antibody, an IgG4 antibody, or combinations thereof. In one embodiment, the antibody is an IgG1 antibody. In one embodiment, the antibody is an IgG2 antibody. In one embodiment, the antibody is an IgG4 antibody. In one embodiment, the antibody is a chimeric IgG2/IgG4 antibody. In one embodiment, the antibody is a chimeric IgG2/IgG1 antibody. In one embodiment, the antibody is a chimeric IgG2/IgG1/IgG4 antibody.

In some embodiments, the antibody is selected from the group consisting of an anti-Programmed Cell Death 1 antibody (e.g. an anti-PD1 antibody as described in U.S. Pat. App. Pub. No. US2015/0203579A1), an anti-Programmed Cell Death Ligand-1 (e.g. an anti-PD-L1 antibody as described in in U.S. Pat. App. Pub. No. US2015/0203580A1), an anti-Dll4 antibody, an anti-Angiopoetin-2 antibody (e.g. an anti-ANG2 antibody as described in U.S. Pat. No. 9,402,898), an anti-Angiopoetin-Like 3 antibody (e.g. an anti-AngPtl3 antibody as described in U.S. Pat. No. 9,018,356), an anti-platelet derived growth factor receptor antibody (e.g. an anti-PDGFR antibody as described in U.S. Pat. No. 9,265,827), an anti-Erb3 antibody, an anti-Prolactin Receptor antibody (e.g. anti-PRLR antibody as described in U.S. Pat. No. 9,302,015), an anti-Complement 5 antibody (e.g. an anti-C5 antibody as described in U.S. Pat. App. Pub. No US2015/0313194A1), an anti-TNF antibody, an anti-epidermal growth factor receptor antibody (e.g. an anti-EGFR antibody as described in U.S. Pat. No. 9,132,192 or an anti-EGFRvIII antibody as described in U.S. Pat. App. Pub. No. US2015/0259423A1), an anti-Proprotein Convertase Subtilisin Kexin-9 antibody (e.g. an anti-PCSK9 antibody as described in U.S. Pat. No. 8,062,640 or U.S. Pat. App. Pub. No. US2014/0044730A1), an anti-Growth And Differentiation Factor-8 antibody (e.g. an anti-GDF8 antibody, also known as anti-myostatin antibody, as described in U.S. Pat. Nos. 8,871,209 or 9,260,515), an anti-Glucagon Receptor (e.g. anti-GCGR antibody as described in U.S. Pat. App. Pub. Nos. US2015/0337045A1 or US2016/

0075778A1), an anti-VEGF antibody, an anti-IL1R antibody, an interleukin 4 receptor antibody (e.g., an anti-IL4R antibody as described in U.S. Pat. App. Pub. No. US2014/0271681A1 or U.S. Pat. Nos. 8,735,095 or 8,945,559), an anti-interleukin 6 receptor antibody (e.g. an anti-IL6R antibody as described in U.S. Pat. Nos. 7,582,298, 8,043,617 or 9,173,880), an anti-IL1 antibody, an anti-IL2 antibody, an anti-IL3 antibody, an anti-IL4 antibody, an anti-IL5 antibody, an anti-IL6 antibody, an anti-IL7 antibody, an anti-interleukin 33 (e.g. anti-IL33 antibody as described in U.S. Pat. App. Pub. Nos. US2014/0271658A1 or US2014/0271642A1), an anti-Cluster of differentiation 3 (e.g. an anti-CD3 antibody, as described in U.S. Pat. App. Pub. Nos. US2014/0088295A1 and US20150266966A1, and in U.S. Application No. 62/222,605), an anti-Cluster of differentiation 20 (e.g. an anti-CD20 antibody as described in U.S. Pat. App. Pub. Nos. US2014/0088295A1 and US20150266966A1, and in U.S. Pat. No. 7,879,984), an anti-CD19 antibody, an anti-CD28 antibody, an anti-Cluster of Differentiation-48 (e.g. anti-CD48 antibody as described in U.S. Pat. No. 9,228,014), an anti-Fel d1 antibody (e.g. as described in U.S. Pat. No. 9,079,948), an anti-influenza virus antibody, an anti-Respiratory syncytial virus antibody (e.g. anti-RSV antibody as described in U.S. Pat. App. Pub. No. US2014/0271653A1), an anti-Middle East Respiratory Syndrome virus (e.g. an anti-MERS-CoV antibody as described in U.S. Pat. App. Pub. No. US2015/0337029A1), an anti-Ebola virus antibody (e.g. as described in U.S. Pat. App. Pub. No. US2016/0215040), an anti-Zika virus antibody, an anti-Severe Acute Respiratory Syndrome (SARS) antibody (e.g., an anti-SARS-CoV antibody, an anti-COVID-19 antibody (e.g., an anti-SARS-CoV-2 antibody), an anti-Lymphocyte Activation Gene 3 antibody (e.g. an anti-LAG3 antibody, or an anti-CD223 antibody), an anti-Nerve Growth Factor antibody (e.g. an anti-NGF antibody as described in U.S. Pat. App. Pub. No. US2016/0017029 and U.S. Pat. Nos. 8,309,088 and 9,353,176) and an anti-Activin A antibody. In some embodiments, the bispecific antibody is selected from the group consisting of an anti-CD3×anti-CD20 bispecific antibody (as described in U.S. Pat. App. Pub. Nos. US2014/0088295A1 and US20150266966A1), an anti-CD3×anti-Mucin 16 bispecific antibody (e.g., an anti-CD3×anti-Muc16 bispecific antibody), and an anti-CD3×anti-Prostate-specific membrane antigen bispecific antibody (e.g., an anti-CD3×anti-PSMA bispecific antibody). In one embodiment, the protein of interest comprises a combination of any of the foregoing.

In some embodiments, the protein of interest is selected from the group consisting of an anti-influenza virus antibody, an anti-Respiratory syncytial virus antibody (e.g. anti-RSV antibody as described in U.S. Pat. App. Pub. No. US2014/0271653A1), an anti-Middle East Respiratory Syndrome virus (e.g. an anti-MERS-CoV antibody as described in U.S. Pat. App. Pub. No. US2015/0337029A1), an anti-Ebola virus antibody (e.g. as described in U.S. Pat. App. Pub. No. US2016/0215040), an anti-Zika virus antibody, an anti-Severe Acute Respiratory Syndrome (SARS) antibody (e.g., an anti-SARS-CoV antibody, an anti-COVID-19 antibody (e.g., an anti-SARS-CoV-2 antibody). In one embodiment, the protein of interest comprises a combination of any of the foregoing.

In some embodiments, the protein of interest is selected from the group consisting of alirocumab, sarilumab, fasinumab, nesvacumab, dupilumab, trevogrumab, evinacumab, and rinucumab. In one embodiment, the protein of interest comprises a combination of any of the foregoing.

In some embodiments, the protein of interest is a recombinant protein that contains an Fc moiety and another domain, (e.g., an Fc-fusion protein). In some embodiments, an Fc-fusion protein is a receptor Fc-fusion protein, which contains one or more extracellular domain(s) of a receptor coupled to an Fc moiety. In some embodiments, the Fc moiety comprises a hinge region followed by a CH2 and CH3 domain of an IgG. In some embodiments, the receptor Fc-fusion protein contains two or more distinct receptor chains that bind to either a single ligand or multiple ligands. For example, an Fc-fusion protein is a TRAP protein, such as for example an IL-1 trap (e.g., rilonacept, which contains the IL-1RAcP ligand binding region fused to the Il-1R1 extracellular region fused to Fc of hIgG1; see U.S. Pat. No. 6,927,004, which is herein incorporated by reference in its entirety), or a VEGF trap (e.g., aflibercept or ziv-aflibercept, which contains the Ig domain 2 of the VEGF receptor Flt1 fused to the Ig domain 3 of the VEGF receptor Flk1 fused to Fc of hIgG1; see U.S. Pat. Nos. 7,087,411 and 7,279,159). In other embodiments, an Fc-fusion protein is a ScFv-Fc-fusion protein, which contains one or more of one or more antigen-binding domain(s), such as a variable heavy chain fragment and a variable light chain fragment, of an antibody coupled to an Fc moiety.

Again, the present disclosure is not limited to any particular type of cell for recombinant protein production. Examples of cell types suitable for recombinant protein production include mammalian cells, insect cells, avian cells, bacterial cells, and yeast cells. The cells may be stem cells or recombinant cells transformed with a vector for recombinant gene expression, or cells transfected with a virus for producing viral products. The cells may contain a recombinant heterologous polynucleotide construct that encodes a protein of interest. That construct can be an episome or it can be an element that is physically integrated into the genome of the cell. The cells may also produce a protein of interest without having that protein encoded on a heterologous polypeptide construct. In other words, the cell may naturally encode the protein of interest, such as a B-cell producing an antibody. The cells may also be primary cells, such as chicken embryo cells, or primary cell lines.

Examples of useful cells include CHO, COS, retinal cell, Vero, CV1, kidney, HeLa, HepG2, W138, MRC 5, Colo25, HB 8065, HL-60, lymphocyte, A431, CV-1, U937, 3T3, L cell, C127 cell, SP2/0, NS-0, MMT cell, stem cell, tumor cell, and a cell line derived from an aforementioned cell. In various embodiments, the cell line is a CHO cell derivative, such as CHO-K1, CHO DUX B-11, CHO DG-44, Veggie-CHO, GS-CHO, S-CHO, or CHO lec mutant lines.

A production phase can be conducted at any scale of culture, from shaker flasks or wave bags, to 250 mL bioreactors, to one-liter bioreactors, and to large scale industrial bioreactors. Likewise, a seed train expansion phase can be conducted at any scale of culture, from and shaker flasks or wave bags, to 250 mL bioreactors, to one-liter or larger bioreactors. A large scale process can be conducted in a volume of about 100 liters to 20,000 liters or more. One or more of several means may be used to control protein production, such as temperature shift or chemical induction. A growth phase may occur at a higher temperature than a production phase. For example, a growth phase may occur at a first temperature of about 35° C. to 38° C., and a production phase may occur at a second temperature of about 29° C. to 37° C., optionally from about 30° C. to 36° C. or from about 30° C. to 34° C. In addition, chemical inducers of protein production, such as caffeine, butyrate, tamoxifen, estrogen, tetracycline, doxycycline, and hexamethylene bisacetamide (HMBA), may be added concurrent with, before, or after a temperature shift. If inducers are added after a temperature shift, they can be added from one hour to five days after the temperature shift, such as from one to two days after the temperature shift. Production cell cultures may be run as continuous feed culture system, as in a chemostat (see C. Altamirano et al., 2001 supra), or according to a fed-batch process (Huang, 2010 supra).

EMBODIMENTS OF THE DISCLOSURE

In one embodiment, the disclosure relates to methods for culturing eukaryotic cells for improved cell culture performance, the method comprising: propagating or maintaining eukaryotic cells in a defined cell culture medium; wherein the defined cell culture medium is supplemented with asparagine in an amount from about 3.6 mM to about 43.2 mM during early fed-batch cell culture and from about 3.6 mM to about 21.6 mM during late fed-batch cell culture; and maintaining said cells in said asparagine supplemented cell culture medium for at least a portion of the early and late fed-batch cell culture; wherein at least one cell culture performance parameter is improved by the asparagine supplementation, as compared to a similar method with a lower amount of asparagine supplementation or no asparagine supplementation in early and/or late fed-batch cell culture.

In certain embodiments of the methods for culturing eukaryotic cells for improved cell culture performance of the disclosure, the asparagine supplement is provided as part of a bulk feed or as a separate asparagine supplement feed in early and/or late fed-batch cell culture.

In certain embodiments of the methods for culturing eukaryotic cells for improved cell culture performance of the disclosure, the asparagine supplement is provided continuously or as bolus in early and/or late fed-batch cell culture.

In certain embodiments of the methods for culturing eukaryotic cells for improved cell culture performance of the disclosure, the defined cell culture medium is supplement with asparagine in an amount from about 7.2 mM to about 21.6 mM during early fed-batch cell culture and about 3.6 mM to about 10.8 mM during late fed-batch cell culture.

In certain embodiments of the methods for culturing eukaryotic cells for improved cell culture performance of the disclosure, the methods further comprise expressing a recombinant protein of interest from the eukaryotic cells during the fed-batch cell culture.

In certain embodiments of the methods for culturing eukaryotic cells for improved cell culture performance of the disclosure, the at least one cell culture performance parameter is selected from the group consisting of increased cell viability, increased cell growth rate, increased cell density, increased titer of the recombinant protein of interest, increased yield of the recombinant protein of interest, reduction in depletions of essential amino acids in at least a portion of the cell culture, reduction in the formation of at least one cell culture by-product in at least a portion of the cell culture, and improvement of at least one indicator of protein quality.

In certain embodiments of the methods for culturing eukaryotic cells for improved cell culture performance of the disclosure, the at least one cell culture by-product is selected from the group consisting of ammonium ions and alanine.

In certain embodiments of the methods for culturing eukaryotic cells for improved cell culture performance of the disclosure, the at least one indicator of protein quality is a reduction in protein sequence variants.

In certain embodiments of the methods for culturing eukaryotic cells for improved cell culture performance of the disclosure, the titer of the recombinant protein of interest is at least 3%, 5%, 8%, 9%, 10%, 11%, 12%, 13%, 14%, 15%, or at least 20% higher than the titer compared to cell(s) cultured with a lower amount of asparagine supplementation in early and/or late fed-batch cell culture.

In certain embodiments of the methods for culturing eukaryotic cells for improved cell culture performance of the disclosure, the yield of the recombinant protein of interest is increased by at least 0.1 g/L, at least 0.5 g/L, at least 1 g/L, at least 1.2 g/L, at least 1.4 g/L, at least 1.6 g/L, at least 1.8 g/L, at least 2 g/L, at least 2.2 g/L, at least 2.4 g/L, or at least 2.5 g/L compared to a similar method wherein cell(s) are cultured with a lower amount of asparagine supplementation in early and/or late fed-batch cell culture.

In certain embodiments of the methods for culturing eukaryotic cells for improved cell culture performance of the disclosure, the cell culture maintains a viable cell count of at least about 10-50 Mcells/ml during at least a portion of the late fed-batch cell culture.

In certain embodiments of the methods for culturing eukaryotic cells for improved cell culture performance of the disclosure, the cells are maintained under asparagine supplemented cell culture conditions for at least 2 days, at least 3 days, at least 4 days, at least 5 days, or for the duration of the early and/or late fed-batch cell culture.

In certain embodiments of the methods for culturing eukaryotic cells for improved cell culture performance of the disclosure, the asparagine supplement is provided at least once, at least twice, at least three times, at least four times, at least five times, daily or continuously for at least a portion of the early fed-batch cell culture.

In certain embodiments of the methods for culturing eukaryotic cells for improved cell culture performance of the disclosure, the asparagine supplement is provided at least once, at least twice, at least three times, at least four times, at least five times, daily or continuously for at least a portion of the late fed-batch cell culture.

In certain embodiments of the methods for culturing eukaryotic cells for improved cell culture performance of the disclosure, the asparagine supplement is provided continuously for at least 2 days, at least 3 days, at least 4 days, at least 5 days, or for the duration of the early fed-batch cell culture.

In certain embodiments of the methods for culturing eukaryotic cells for improved cell culture performance of the disclosure, the asparagine supplement is provided continuously for at least 2 days, at least 3 days, at least 4 days, at least 5 days, or for the duration of the late fed-batch cell culture.

In certain embodiments of the methods for culturing eukaryotic cells for improved cell culture performance of the disclosure, the asparagine supplement is provided continuously beginning on day 5 or after of the fed-batch cell culture, and thereafter for at least a portion of the late fed-batch cell culture.

In certain embodiments of the methods for culturing eukaryotic cells for improved cell culture performance of the disclosure, the continuous asparagine supplement is discontinued on or after day 10 of the fed-batch of the cell culture.

In certain embodiments of the methods for culturing eukaryotic cells for improved cell culture performance of the disclosure, the asparagine supplement is provided continuously in early and/or late fed-batch cell culture.

In certain embodiments of the methods for culturing eukaryotic cells for improved cell culture performance of the disclosure, the asparagine supplement is provided as part of a continuous bulk feed.

In certain embodiments of the methods for culturing eukaryotic cells for improved cell culture performance of the disclosure, the asparagine supplement is provided as part of a separate continuous asparagine supplement feed.

In certain embodiments of the methods for culturing eukaryotic cells for improved cell culture performance of the disclosure, the amino acid depletions in the cell culture of asparagine, aspartic acid, and glutamic acid are delayed by at least 1 day, at least 2 days, at least 3 days, or at least 4 days or more, as compared to a similar method with asparagine supplementation provided in early and/or late fed-batch cell culture as a bolus feed.

In certain embodiments of the methods for culturing eukaryotic cells for improved cell culture performance of the disclosure, the eukaryotic cell is a mammalian cell.

In certain embodiments of the methods for culturing eukaryotic cells for improved cell culture performance of the disclosure, the eukaryotic cell is a CHO cell.

In certain embodiments of the methods for culturing eukaryotic cells for improved cell culture performance of the disclosure, the eukaryotic cell is a high asparagine consuming cell line, such that the cell consumes at least about 1.8 mM/day to about 9.3 mM/day of asparagine.

In certain embodiments of the methods for culturing eukaryotic cells for improved cell culture performance of the disclosure, the eukaryotic cell is a low asparagine consuming cell line, such that the cell consumes at least about 0.32 mM/day to about 1.8 mM/day of asparagine.

In certain embodiments of the methods for culturing eukaryotic cells for improved cell culture performance of the disclosure, the eukaryotic cell is a high producing cell line, such that the recombinant protein of interest is produced at a yield of at least 4 g/L, at least 5 g/L, at least 6 g/L, at least 7 g/L, at least 8 g/L, at least 9 g/L, or at least 10 g/L, at least 11 g/L, at least 12 g/L, at least 13 g/L, at least 14 g/L.

In certain embodiments of the methods for culturing eukaryotic cells for improved cell culture performance of the disclosure, the recombinant protein of interest is an antibody, a human antibody, a humanized antibody, a chimeric antibody, a monoclonal antibody, a multispecific antibody, a bispecific antibody, an antigen binding antibody fragment, a single chain antibody, a diabody, triabody or tetrabody, a Fab fragment or a F(ab')2 fragment, an IgD antibody, an IgE antibody, an IgM antibody, an IgG antibody, an IgG1 antibody, an IgG2 antibody, an IgG3 antibody, or an IgG4 antibody.

In certain embodiments of the methods for culturing eukaryotic cells for improved cell culture performance of the disclosure, the recombinant protein of interest comprises an Fc domain.

In certain embodiments of the methods for culturing eukaryotic cells for improved cell culture performance of the disclosure, the recombinant protein of interest is selected from the group consisting of an Fc-fusion protein, a receptor-Fc-fusion protein (TRAP), an antibody, an antibody fragment, and a ScFv-Fc fusion protein.

In certain embodiments of the methods for culturing eukaryotic cells for improved cell culture performance of the disclosure, the recombinant protein of interest is selected from the group consisting of an anti-PD1 antibody, an anti-PDL-1 antibody, an anti-D114 antibody, an anti-ANG2 antibody, an anti-AngPtl3 antibody, an anti-PDGFR antibody, an anti-Erb3 antibody, an anti-PRLR antibody, an anti-TNF antibody, an anti-EGFR antibody, an anti-PCSK9 antibody, an anti-GDF8 antibody, an anti-GCGR antibody, an anti-VEGF antibody, an anti-IL1R antibody, an anti-IL4R antibody, an anti-IL6R antibody, an anti-IL1 antibody, an anti-IL2 antibody, an anti-IL3 antibody, an anti-IL4 antibody, an anti-IL5 antibody, an anti-IL6 antibody, an anti-IL7 antibody, an anti-RSV antibody, an anti-NGF antibody, an anti-CD3 antibody, an anti-CD20 antibody, an anti-CD19 antibody, an anti-CD28 antibody, an anti-CD48 antibody, an anti-CD3/anti-CD20 bispecific antibody, an anti-CD3/anti-MUC16 bispecific antibody, and an anti-CD3/anti-PSMA bispecific antibody.

In certain embodiments of the methods for culturing eukaryotic cells for improved cell culture performance of the disclosure, the recombinant protein of interest is selected from the group consisting of an anti-influenza virus antibody, an anti-Respiratory syncytial virus (RSV) antibody, an anti-Middle East Respiratory Syndrome (MERS) virus, an anti-Ebola virus antibody, an anti-Zika virus antibody, an anti-Severe Acute Respiratory Syndrome (SARS) antibody, and an anti-COVID-19 antibody.

In certain embodiments of the methods for culturing eukaryotic cells for improved cell culture performance of the disclosure, the recombinant protein of interest is selected from at least one alirocumab, sarilumab, fasinumab, nesvacumab, dupilumab, trevogrumab, evinacumab, rinucumab, casirivimab, or imdevimab.

In other embodiments, the disclosure relates to methods for preventing asparagine sequence variants in a polypeptide of interest expressed from mammalian cells in cell culture, the method comprising: propagating or maintaining mammalian cells in a defined cell culture medium; wherein the defined cell culture medium is supplemented with asparagine in an amount from about 3.6 mM to about 43.2 mM during early fed-batch cell culture and from about 3.6 mM to about 21.6 mM during late fed-batch cell culture; and maintaining said cells in said asparagine supplemented cell culture medium for at least a portion of the early and late fed-batch cell culture under conditions sufficient for expression of the polypeptide of interest; wherein extracellular asparagine levels are maintained in the cell culture medium during at least early stage fed-batch cell culture above a depletion limit of about 0.1 mM such that the polypeptide of interest expressed by the mammalian cells comprise less than 0.30% of asparagine sequence variants at all individual SV loci.

In certain embodiments of the methods for preventing asparagine sequence variants in a polypeptide of interest expressed from mammalian cells in cell culture of the disclosure, the polypeptide of interest expressed by the mammalian cells comprise less than 0.30% of asparagine sequence variants at all individual SV loci after day 12 of the cell culture.

In certain embodiments of the methods for preventing asparagine sequence variants in a polypeptide of interest expressed from mammalian cells in cell culture of the disclosure, the asparagine supplement is provided as part of a bulk feed or as a separate asparagine supplement feed in early and/or late fed-batch cell culture.

In certain embodiments of the methods for preventing asparagine sequence variants in a polypeptide of interest expressed from mammalian cells in cell culture of the disclosure, the asparagine supplement is provided continuously or as bolus in early and/or late fed-batch cell culture.

In certain embodiments of the methods for preventing asparagine sequence variants in a polypeptide of interest expressed from mammalian cells in cell culture of the disclosure, the defined cell culture medium is supplement with asparagine in an amount from about 7.2 mM to about 21.6 mM during early fed-batch cell culture and about 3.6 mM to about 10.8 mM during late fed-batch cell culture.

In certain embodiments of the methods for preventing asparagine sequence variants in a polypeptide of interest expressed from mammalian cells in cell culture of the disclosure, the cells are maintained under asparagine supplemented cell culture conditions for at least 2 days, at least 3 days, at least 4 days, at least 5 days, or for the duration of the early and/or late fed-batch cell culture.

In certain embodiments of the methods for preventing asparagine sequence variants in a polypeptide of interest expressed from mammalian cells in cell culture of the disclosure, the asparagine supplement is provided at least once, at least twice, at least three times, at least four times, at least five times, daily or continuously for at least a portion of the early fed-batch cell culture.

In certain embodiments of the methods for preventing asparagine sequence variants in a polypeptide of interest expressed from mammalian cells in cell culture of the disclosure, the asparagine supplement is provided at least once, at least twice, at least three times, at least four times, at least five times, daily or continuously for at least a portion of the late fed-batch cell culture.

In certain embodiments of the methods for preventing asparagine sequence variants in a polypeptide of interest expressed from mammalian cells in cell culture of the disclosure, the asparagine supplement is provided continuously for at least 2 days, at least 3 days, at least 4 days, at least 5 days, or for the duration of the early fed-batch cell culture.

In certain embodiments of the methods for preventing asparagine sequence variants in a polypeptide of interest expressed from mammalian cells in cell culture of the disclosure, the asparagine supplement is provided continuously for at least 2 days, at least 3 days, at least 4 days, at least 5 days, or for the duration of the late fed-batch cell culture.

In certain embodiments of the methods of the disclosure, the asparagine supplement is provided continuously beginning on day 5 or after of the fed-batch cell culture, and thereafter for at least a portion of the late fed-batch cell culture.

In certain embodiments of the methods for preventing asparagine sequence variants in a polypeptide of interest expressed from mammalian cells in cell culture of the disclosure, the continuous asparagine supplement is discontinued on or after day 10 of the fed-batch of the cell culture.

In certain embodiments of the methods for preventing asparagine sequence variants in a polypeptide of interest expressed from mammalian cells in cell culture of the disclosure, the asparagine supplement is provided continuously in early and/or late fed-batch cell culture.

In certain embodiments of the methods for preventing asparagine sequence variants in a polypeptide of interest expressed from mammalian cells in cell culture of the disclosure, the asparagine supplement is provided as part of a continuous bulk feed.

In certain embodiments of the methods for preventing asparagine sequence variants in a polypeptide of interest expressed from mammalian cells in cell culture of the disclosure, the asparagine supplement is provided as part of a separate continuous asparagine supplement feed.

In certain embodiments of the methods for preventing asparagine sequence variants in a polypeptide of interest expressed from mammalian cells in cell culture of the disclosure, the asparagine sequence variant is a misincorporation of serine in place of asparagine during translation of the polypeptide of interest.

In other embodiments, the disclosure relates to methods for detecting asparagine sequence variants in a polypeptide of interest expressed from mammalian cells in cell culture, the method comprising: propagating or maintaining mammalian cells in a defined cell culture medium; expressing a recombinant protein of interest from the eukaryotic cells; measuring intracellular and/or extracellular concentrations of asparagine or one or more asparagine related amino acids in the cell culture or defined cell culture medium; and correlating the measured concentrations of asparagine or one or more asparagine related amino acids to the presence of asparagine sequence variants in the expressed polypeptide of interest.

In certain embodiments of the methods for detecting asparagine sequence variants in a polypeptide of interest expressed from mammalian cells in cell culture of the disclosure, the measured concentrations of asparagine or the one or more asparagine related amino acids is inversely correlated to the presence of asparagine sequence variants.

In certain embodiments of the methods for detecting asparagine sequence variants in a polypeptide of interest expressed from mammalian cells in cell culture of the disclosure, the defined cell culture medium is supplemented with asparagine in an amount from about 3.6 mM to about 43.2 mM during early fed-batch cell culture and from about 3.6 mM to about 21.6 mM during late fed-batch cell culture; and the cells are maintained in said asparagine supplemented cell culture medium for at least a portion of the early and late fed-batch cell culture.

In certain embodiments of the methods for detecting asparagine sequence variants in a polypeptide of interest expressed from mammalian cells in cell culture of the disclosure, the one or more asparagine related amino acid is selected from aspartate (Asp), glutamate (Glu), glutamine (Gln), and combinations thereof.

In certain embodiments of the methods for detecting asparagine sequence variants in a polypeptide of interest expressed from mammalian cells in cell culture of the disclosure, the one or more asparagine related amino acid is glutamate (Glu)

In certain embodiments of the methods for detecting asparagine sequence variants in a polypeptide of interest expressed from mammalian cells in cell culture of the disclosure, the one or more asparagine related amino acids may be measured during late fed-batch cell culture.

In certain embodiments of the methods for detecting asparagine sequence variants in a polypeptide of interest expressed from mammalian cells in cell culture of the disclosure, the one or more asparagine related amino acids may be measured after day 5, after day 6, after day 7, after day 8, after day 9, or after day 10 of the cell culture.

In certain embodiments of the methods for detecting asparagine sequence variants in a polypeptide of interest expressed from mammalian cells in cell culture of the disclosure, the one or more asparagine relate amino acids are measured intracellularly.

In certain embodiments of the methods of the disclosure, the one or more asparagine relate amino acids are measured extracellularly.

In other embodiments, the disclosure relates to methods for monitoring and controlling one or more cell culture parameters, the method comprising: measuring one or more cell culture parameters in a cell culture in situ using one or more of freezing point depression, electrochemistry, digital imaging, photometry, bioprocess analyzer, or Raman spectroscopy; comparing the measured one or more cell culture parameters to a predetermined set point value for the cell culture parameter to determine if the one or more cell culture parameters are within a predetermined threshold range; and adjusting one or more of the cell culture parameters if a cell culture parameter is determined to be out of the predetermined threshold range.

In certain embodiments of the methods for monitoring and controlling one or more cell culture parameters of the disclosure, the one or more cell culture parameters are selected from the group consisting of cell growth rate, cell density, cell viability, asparagine concentration, asparagine related amino acid concentration, ammonium ion concentration, and alanine concentration.

In certain embodiments of the methods for monitoring and controlling one or more cell culture parameters of the disclosure, the one or more cell culture parameters are selected from asparagine concentration and ammonium ion concentration.

In certain embodiments of the methods for monitoring and controlling one or more cell culture parameters of the disclosure, if ammonium ion concentration is determined to be outside of a predetermined threshold range, asparagine feed input is adjusted.

The present disclosure is not limited in scope by the specific embodiments described herein, which are intended as illustrations of individual aspects or embodiments of the invention. Functionally equivalent methods and components are within the scope of the invention. Various modifications of the invention, in addition to those described here, are apparent to those skilled in the art from the foregoing description and accompanying drawings. Such modifications fall within the scope of the invention.

All publications mentioned throughout this disclosure are incorporated herein by reference in their entirety.

EXAMPLES

The following examples are provided for illustrative purposes only and are not intended to limit the scope of the invention.

Fed-Batch Methodology

As described herein, fed-batch feed development is performed via an automated AMBR250, 24 way, parallel bioreactor system. The AMBR250 high throughput workstation offers integrated, parallel control of 24 single-use bioreactors. More particularly, the AMBR250 (24 way) is a completely integrated high throughput system that consists of 24 bioreactors, each with a maximum 250 ml working volume under fully automated control with cell culture processes in parallel. Individual continuous control and monitoring for each bioreactor vessel, including temperature, impeller speed, pH and dissolved oxygen (DO), off-gas analysis is provided. The system offers fully automated media fill, inoculation, sampling and feeding. The system uses bioreactors with impellers, sparger or headspace gassing, pH and DO probes and up to four feed lines.

In performing the feed strategy development of the present disclosure, AMBR250 bioreactors (Sartorious Stedim) are run with a working volume up to 250 mL. Proprietary chemically defined basal and feed media are used. The feed media, and feeding strategies are different from one cell line to another. Glucose is fed daily and levels are controlled based on targets. Bioreactors are inoculated with cell culture. Oxygen is maintained by control and pure oxygen is added through the sparger at varying flow rates during the studies. Similarly, pH is maintained by control with $CO_2$ sparging for the upper pH band, with no controlled lower band pH. Inoculation cell density, dissolved oxygen, temperature, pH and dead band are held constant. Agitation and flow rates of air and oxygen are varied depending on scales.

Unless otherwise indicated, a high asparagine consuming, CHO cell line 1 is utilized in all examples, expressing exemplary polypeptide A.

Extracellular Amino Acid Measurement

As described herein, extracellular levels of amino acids may be measured. In certain embodiments, such levels are measured in accordance with the following procedure. Spent cell culture media samples were derivatized and prepared using the Waters AccQ•Tag method protocol and the Waters AccQ•Tag reagent kit (Waters, Milford, MA). Samples were diluted 10× and spiked with a 100 mg/L sarcosine internal standard prior to derivatization (Millipore Sigma, Burlington, MA). Separation of derivatized amino acids and subsequent measurement was performed using a UPLC equipped with an AccQ•Tag Ultra C18 column (1.7 uM, 2.1×10 mm), data was collected at a 260 nm wavelength. Mobile phases and gradient followed the Waters AccQ•Tag method protocol.

Intracellular Amino Acid Measurement

As described herein, intracellular levels of amino acids may be measured. In certain embodiments, such levels are measured in accordance with the following procedure. Cell are collected from the bioreactors and centrifuged at room temperature, the supernatant is separated from the cell pellet. The cell pellet is washed with 1×PBS, centrifuged. PBS is removed, and cell pellets are cold quenched with liquid nitrogen. Study samples are spiked with stable labelled internal standards, extracted, and subjected to protein precipitation with an organic solvent. After centrifugation, an aliquot of the supernatant is diluted and injected onto an Agilent 1290/AB Sciex QTrap 5500 LC-MS/MS system equipped with a C18 reversed phase UHPLC column. The mass spectrometer is operated in positive mode using electrospray ionization (ESI). The peak areas of the individual analyte parent ions are measured against the peak areas of the parent ions of the corresponding internal standards in pseudo-MRM mode. Quantitation is performed using a weighted least squares regression analysis generated from fortified calibration standards prepared immediately prior to each run. LC-MS/MS raw data are collected and processed using AB SCIEX software Analyst 1.6.2. Data reduction is performed using Microsoft Excel for Office 365 v.16.

Asparagine Sequence Variant Analysis

As described herein, asparagine sequence variants of a polypeptide of interest may be measured. While any suitable method of measurement of such sequence variants may be used, the quantitative amount of asparagine sequence variant may be determined as follows. A rapid and sensitive LC-MS based assay focusing on three peptides out of ~50 possible peptides may be used as a screening tool to identify instances of substitution and to get a quantitative estimate of the extent of substitution. The polypeptide of interest may be purified at small scale using appropriate purification methodology. The polypeptide of interest may then be reduced and denatured, followed by enzymatic digestion. In this manner, trypic maps of the polypeptides of interest may be generated and the protein sequences analyzed to determine if there is any variance from the expected sequences. An HPLC gradient based separation may be carried out subsequently and the individual peptides may be analyzed by Q-TOF MS system. Specific peptides may be analyzed in detail by mass spectrometry. Changes in peptide sequence may be analyzed. By way of example, a 27 Da shift is observed for asparagine to seine substitution.

Example 1—Asparagine Impact on Cell Culture and Feed Strategy Development

Fed-batch cell culture performance and feed strategy was evaluated using exemplary CHO cell lines and varied asparagine supplementation. Fed-batch cell culture performance and feed strategy development may be performed using an AMBR250 bioreactor system and amino acid measurements, as described herein.

Figure 3A:
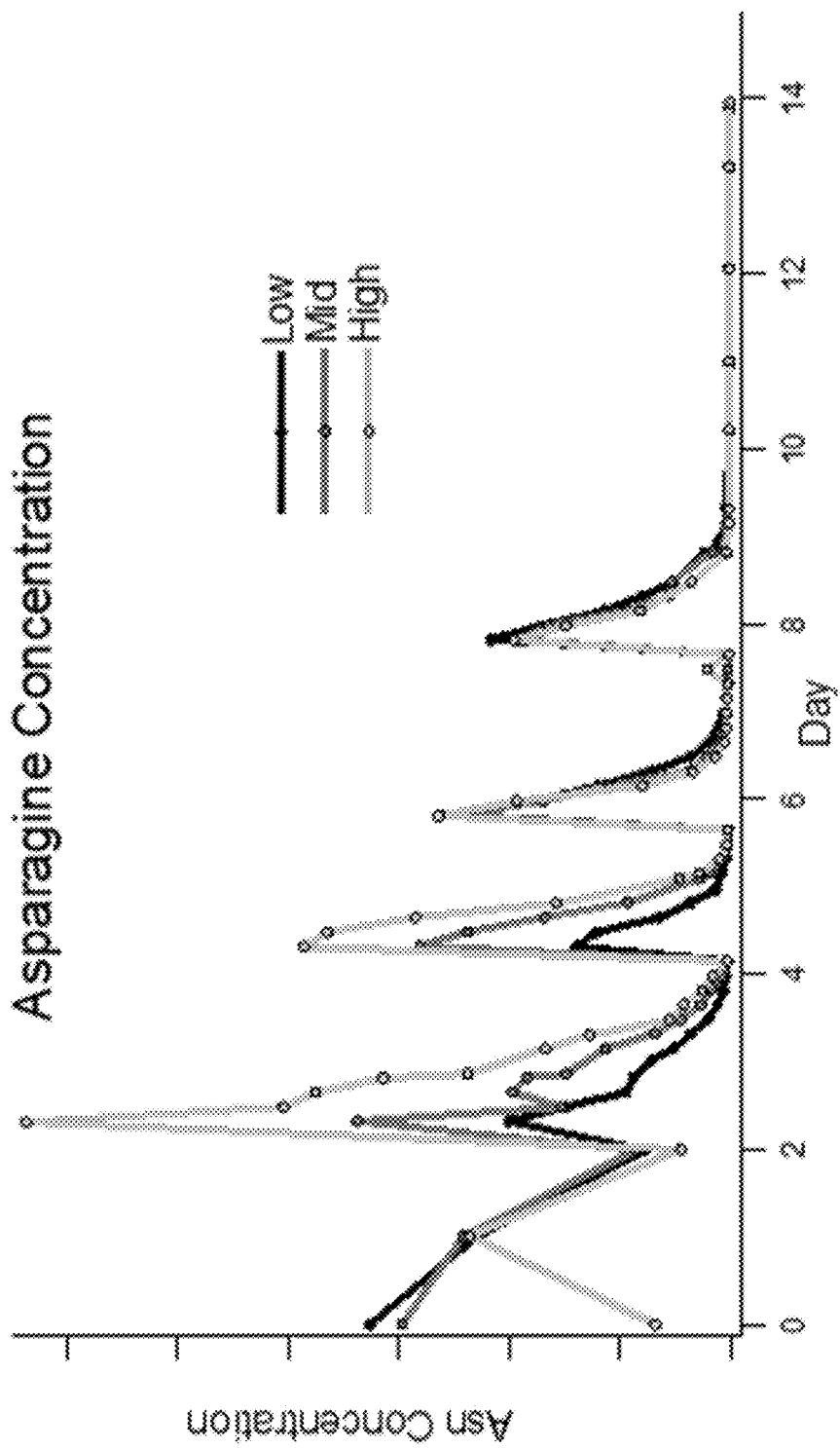
FIG. 3A illustrates a series of early fed-batch asparagine supplements with low, mid and high amount supplements, in accordance with embodiments of the disclosure.
Figure 3B:
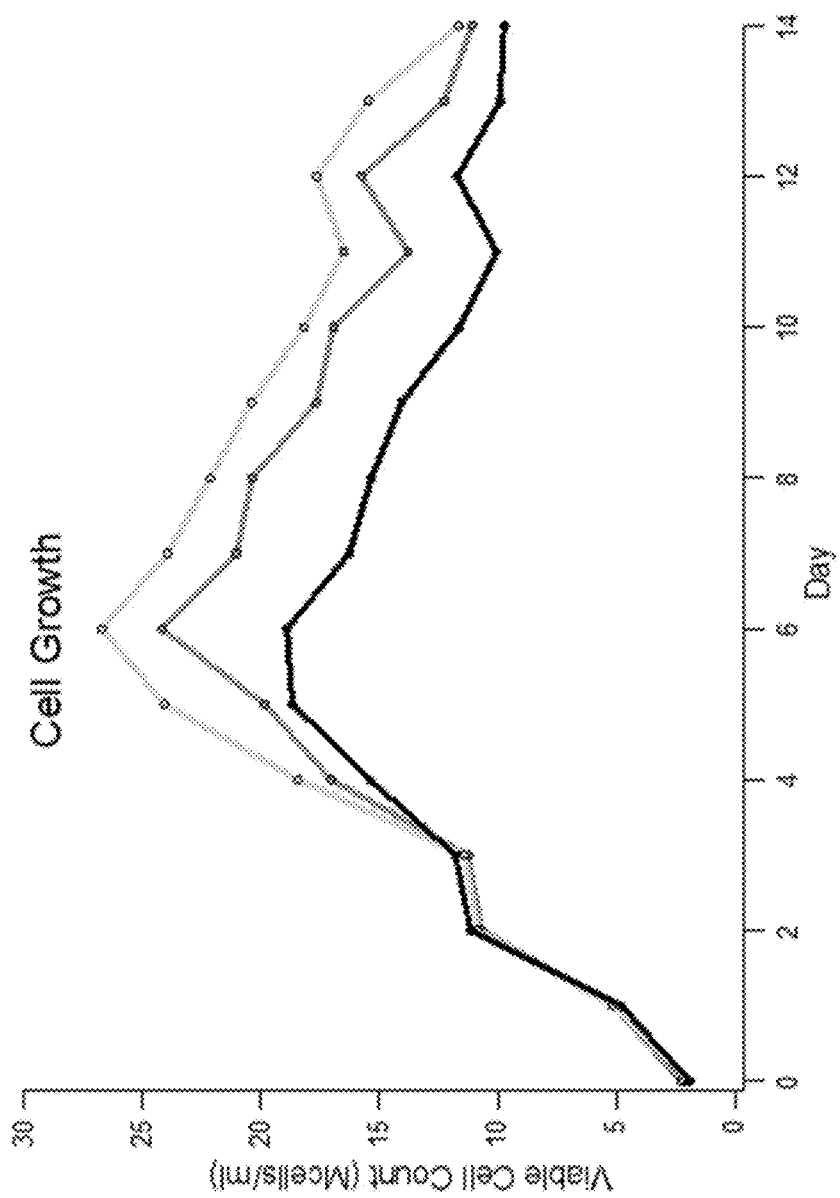
Figure 3C:
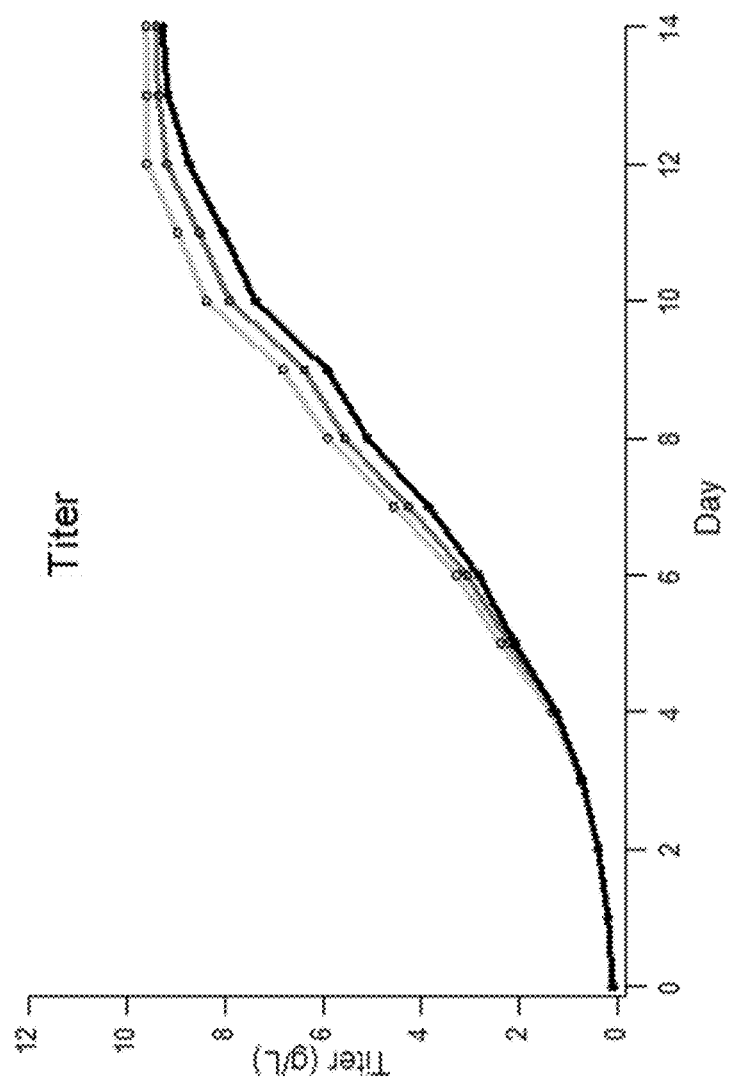
FIG. 3C illustrates an increase in cell culture titer with increasing asparagine supplements, in accordance with embodiments of the disclosure.

With reference to FIGS. 3A-3C, in certain aspects, it was found that increasing asparagine in early fed-batch cell culture leads to increases in cell growth and does not negatively impact culture productivity when balanced against other cell nutrients needs. FIG. 3A illustrates a series of early fed-batch asparagine supplements with low, mid and high amount supplements (ranging from, e.g., about 1.8 mM to about 5.4 mM arginine per feed), but that such asparagine supplements do not prevent late fed-batch asparagine depletions. FIG. 3B illustrates an increase in cell culture growth with increasing amounts of asparagine supplements, while FIG. 3C illustrates an increase in cell culture titer with increasing asparagine supplements until reaching a plateau resulting from depletions of some essential amino acids.

With reference to FIGS. 4A-4C, it was also found that increasing asparagine in late fed-batch cell culture, although increasing by-product formation such as ammonium, does not significantly impact cell culture productivity. More specifically, FIG. 4A illustrates a low and high asparagine supplement in late feeds (ranging from about 1.8 mM to about 7.2 mM per feed), but that such asparagine supplements do not prevent late fed-batch asparagine depletions. While overall cell culture productivity is not negatively impacted (FIG. 4C), higher amounts of asparagine supplement in late fed-batch cell culture may lead to excess by-product formation (FIG. 4B), suggesting that more asparagine may be fed to the cell culture if needed, but that depletions are still difficult to prevent.

Figure 5A:
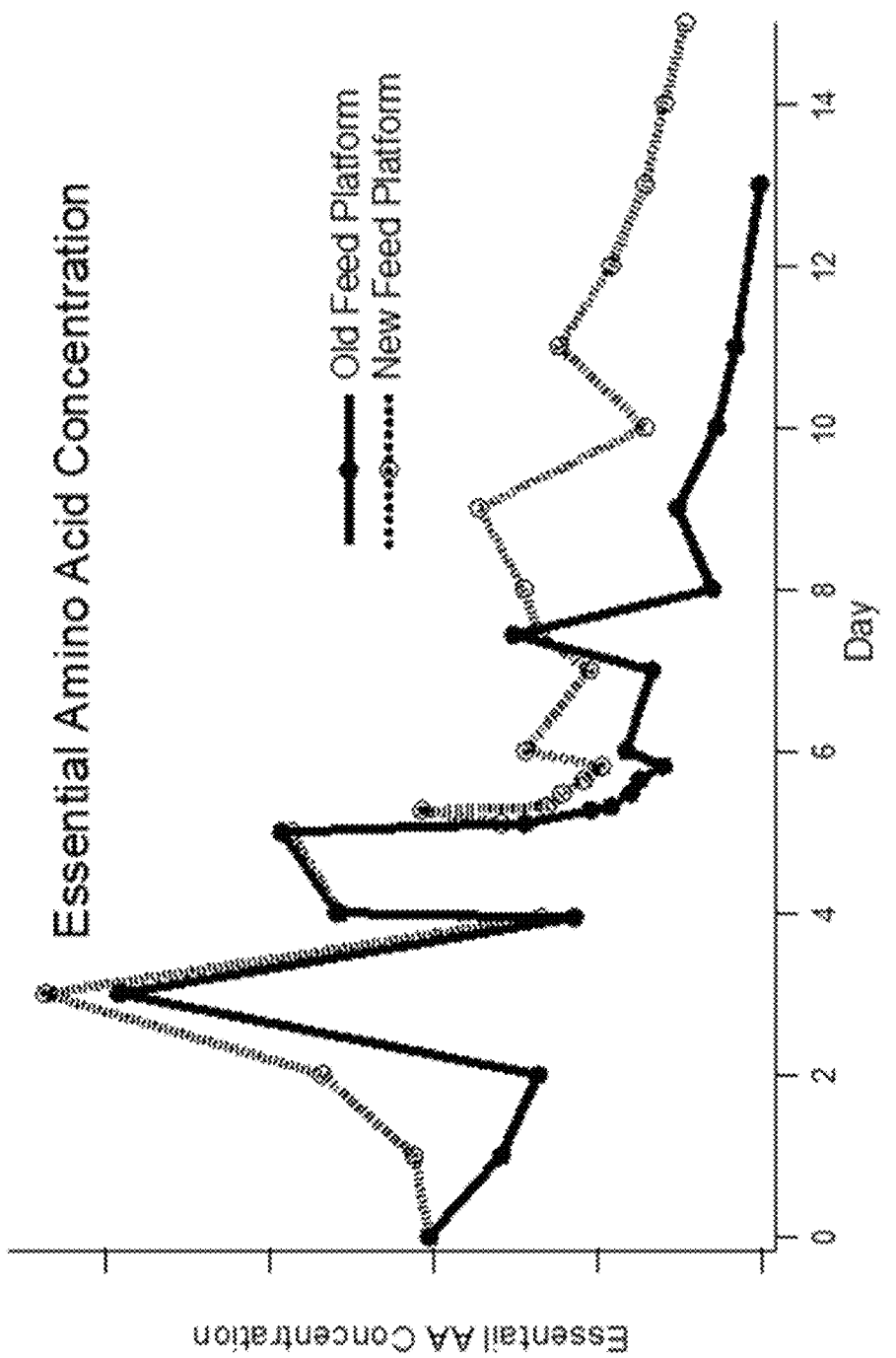
FIG. 5A-5D illustrates an improved asparagine supplementation feed strategy, in accordance with embodiments of the disclosure.
Figure 5B:
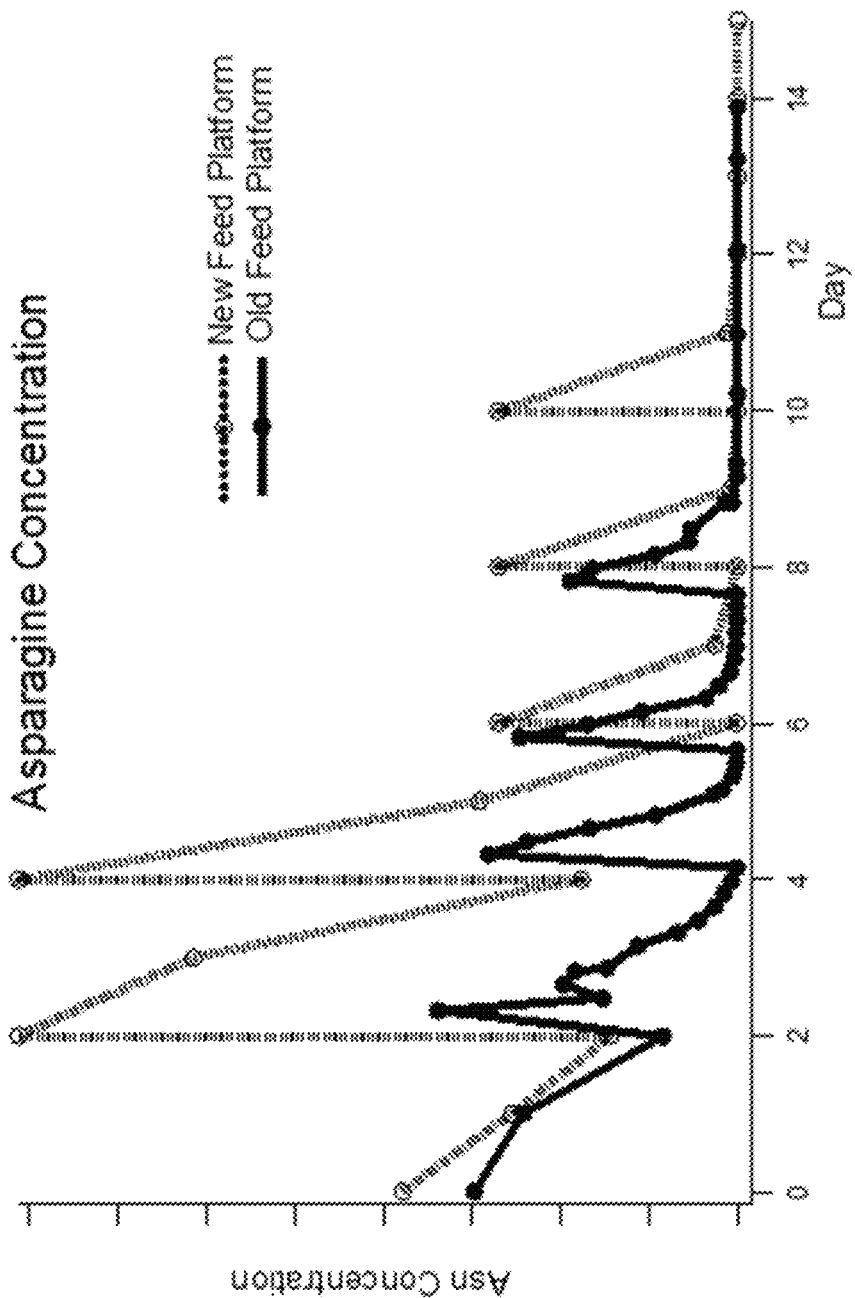
Figure 5C:
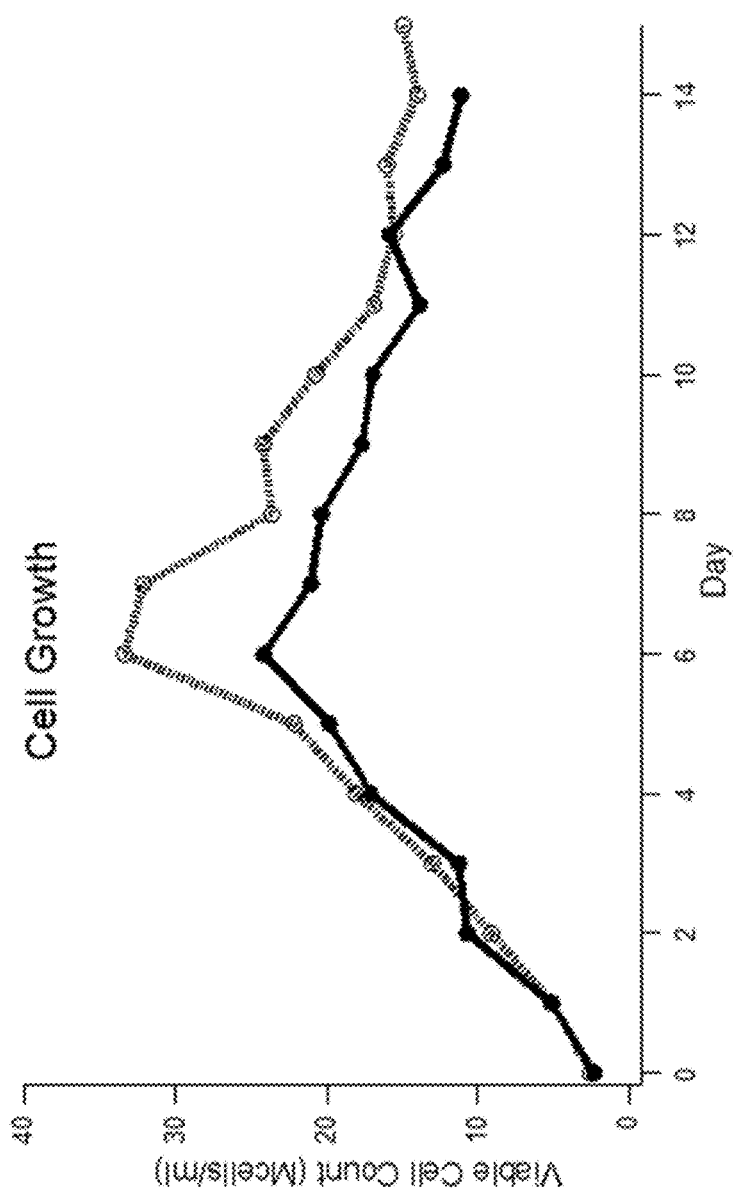
Figure 5D:
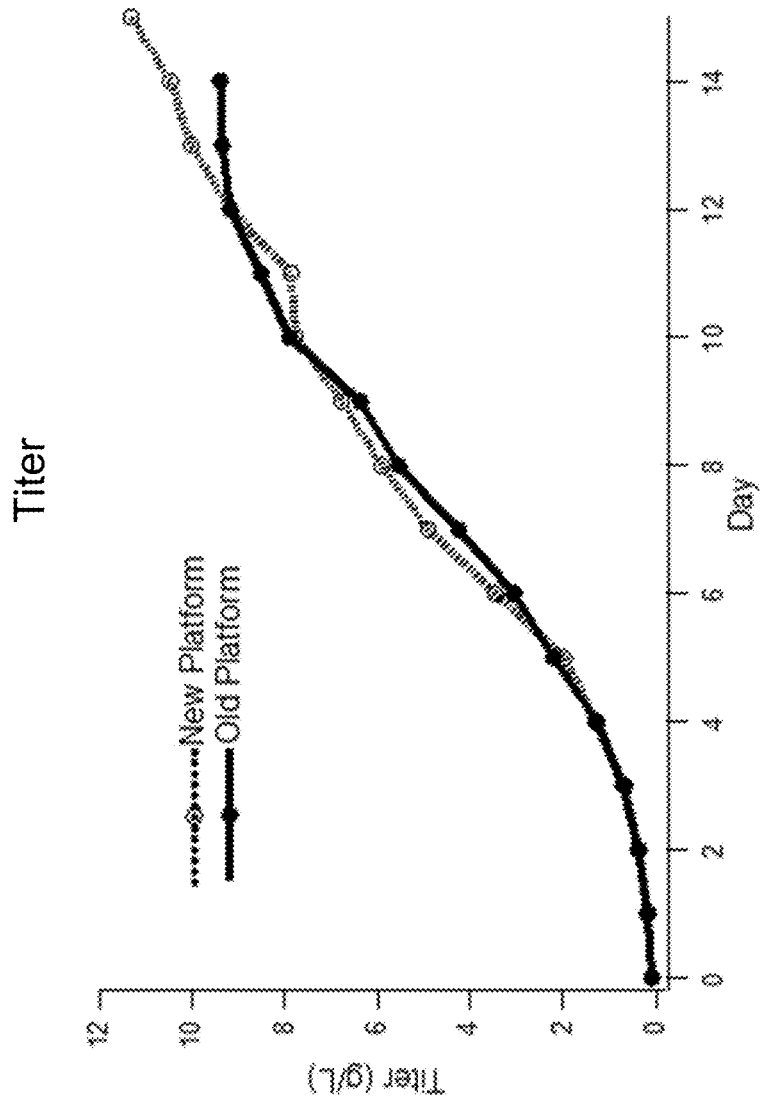
Figure 5E:
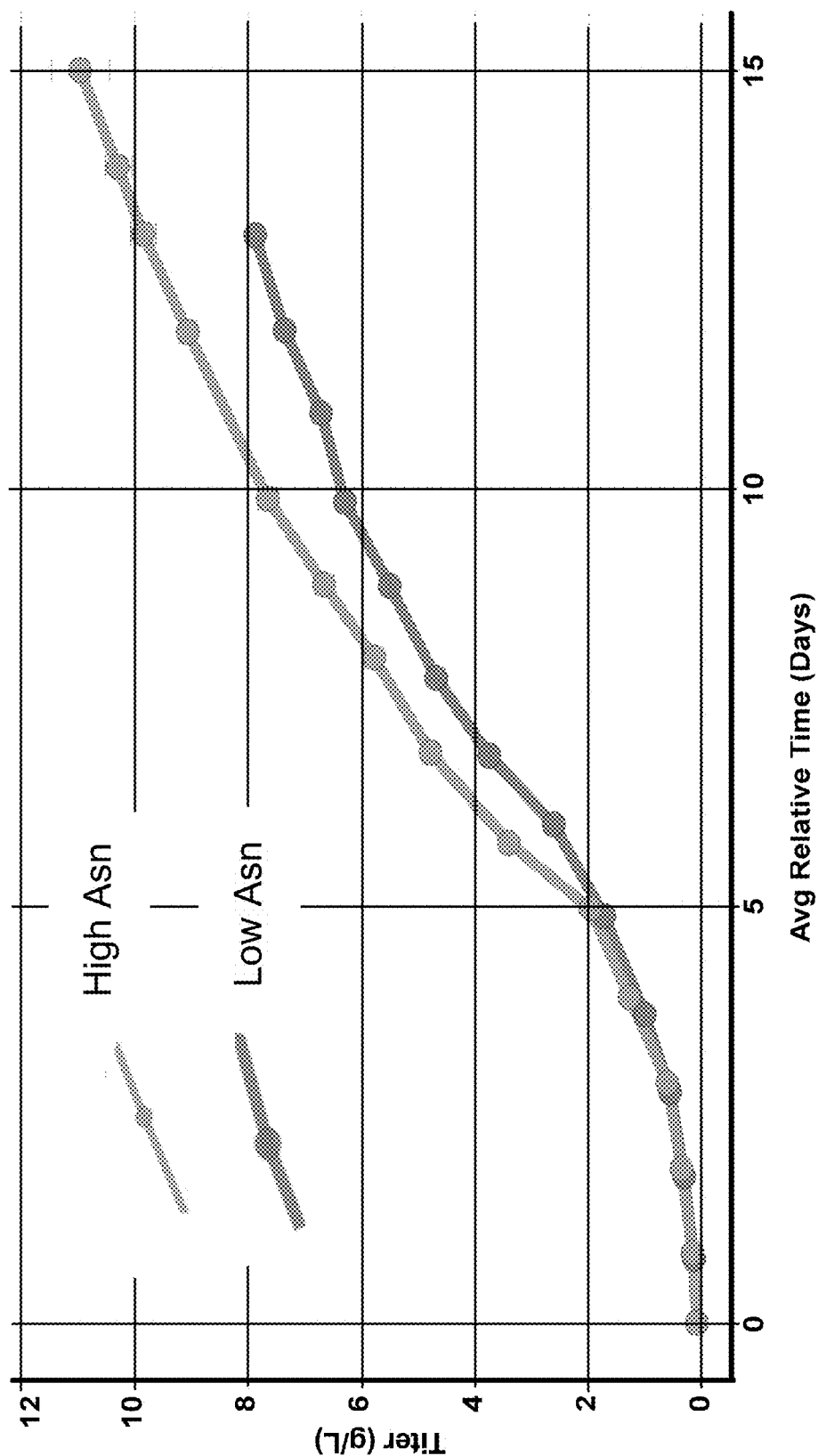
FIGS. 5E-5G, illustrate cell titer (FIG. 5E), viable cell count (FIG. 5F) and cell viability (FIG. 5G) following asparagine supplements in another exemplary cell line, in accordance with embodiments of the disclosure.
Figure 5F:
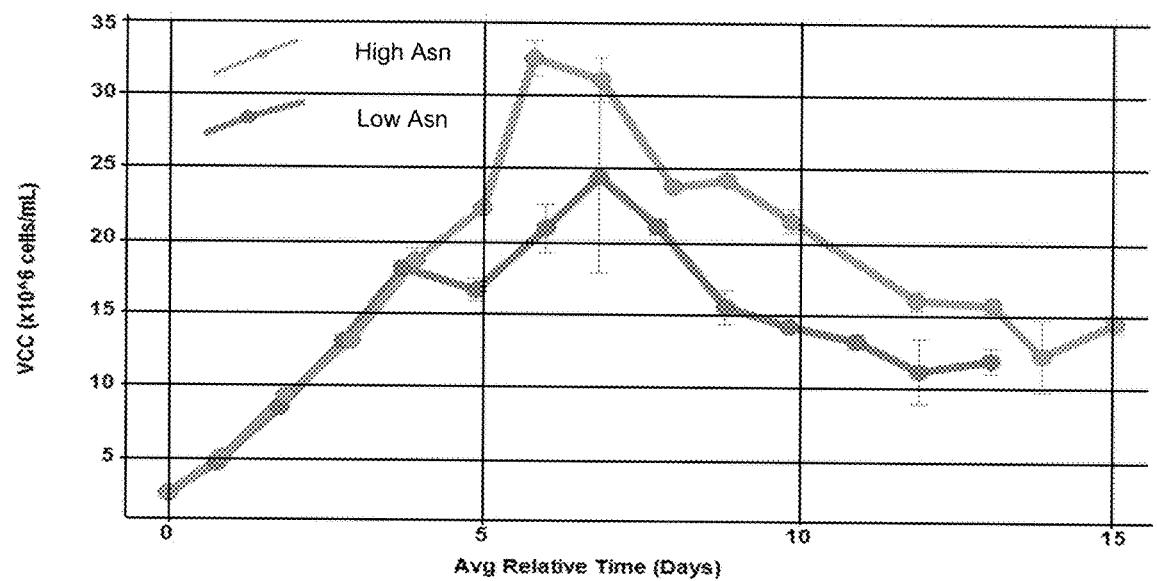
Figure 5G:
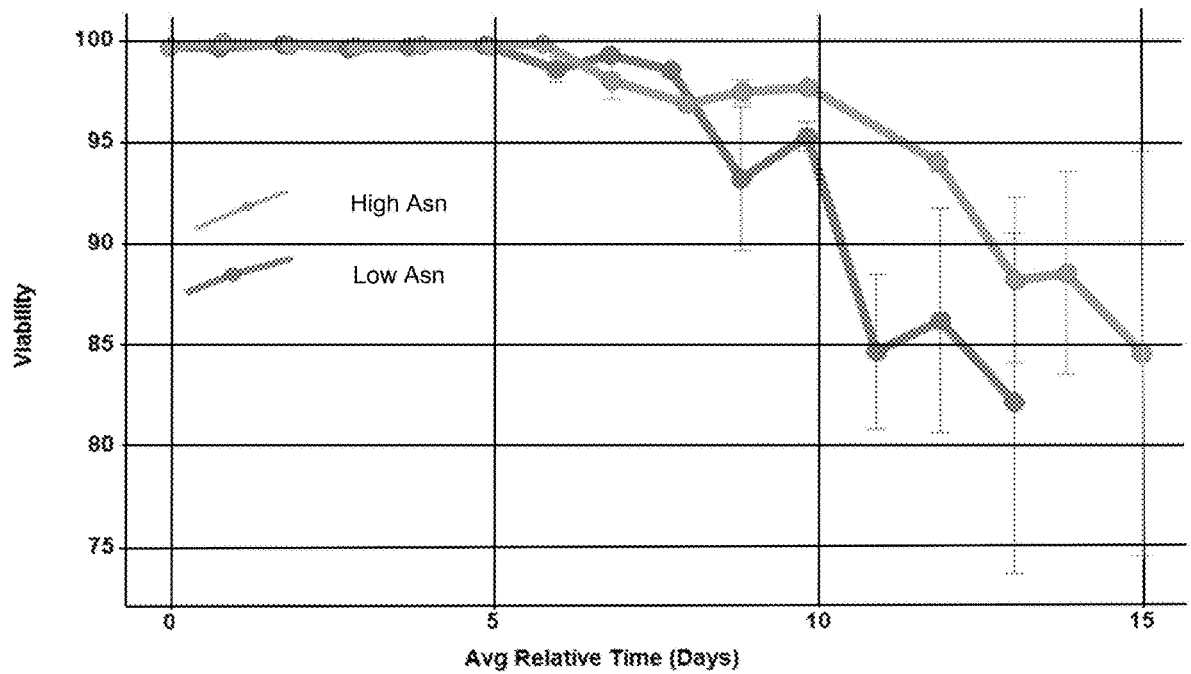

In accordance with embodiments of the disclosure, an improved asparagine supplementation feed strategy (i.e., "new feed platform" with 3× asparagine in early fed-batch feed and 1.5× asparagine in late fed-batch feed) was developed which prevented depletion of essential amino acids and asparagine in early fed-batch cell culture, and provided for an increase in cell culture performance overall. As shown in FIGS. 5A-5D, early fed-batch asparagine supplementation prevented early fed-batch asparagine depletions and increased cell culture growth. Further, as shown, asparagine related increases in cell culture growth with elimination of essential amino acid depletions improved cell culture productivity, with productive fed-batch time being extended and resulting in higher titer. However, higher asparagine supplementation in late fed-batch cell culture still cannot avoid asparagine depletions in late fed-batch. With reference to FIGS. 5E-5G, cell titer, viable cell count and cell viability all improved with higher asparagine supplements in another exemplary cell line.

Figure 6B:
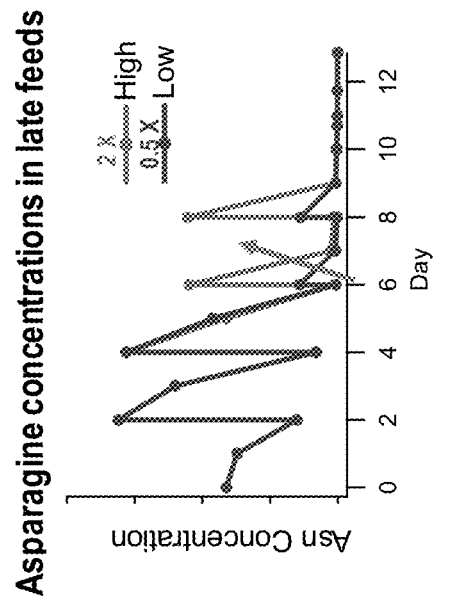
FIG. 6B illustrates asparagine consumption following asparagine supplements in late fed-batch cell culture, in accordance with embodiments of the disclosure.
Figure 6A:
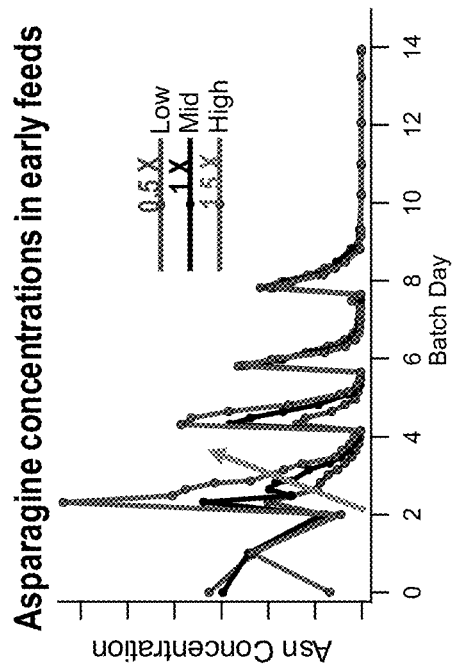

With reference to FIG. 6A, supplementing varying amounts of asparagine in early fed-batch cell culture results in depletions at similar times. However, increasing asparagine supplement amounts increases asparagine consumption rates (see FIG. 7), suggesting that cells are not utilizing asparagine efficiently. With reference to FIG. 6B, supplementing increased asparagine amounts in late fed-batch cell culture does not prevent late fed-batch asparagine depletions, may lead to excess by-product formation, again suggesting that cells are not utilizing asparagine efficiently.

Figure 7:
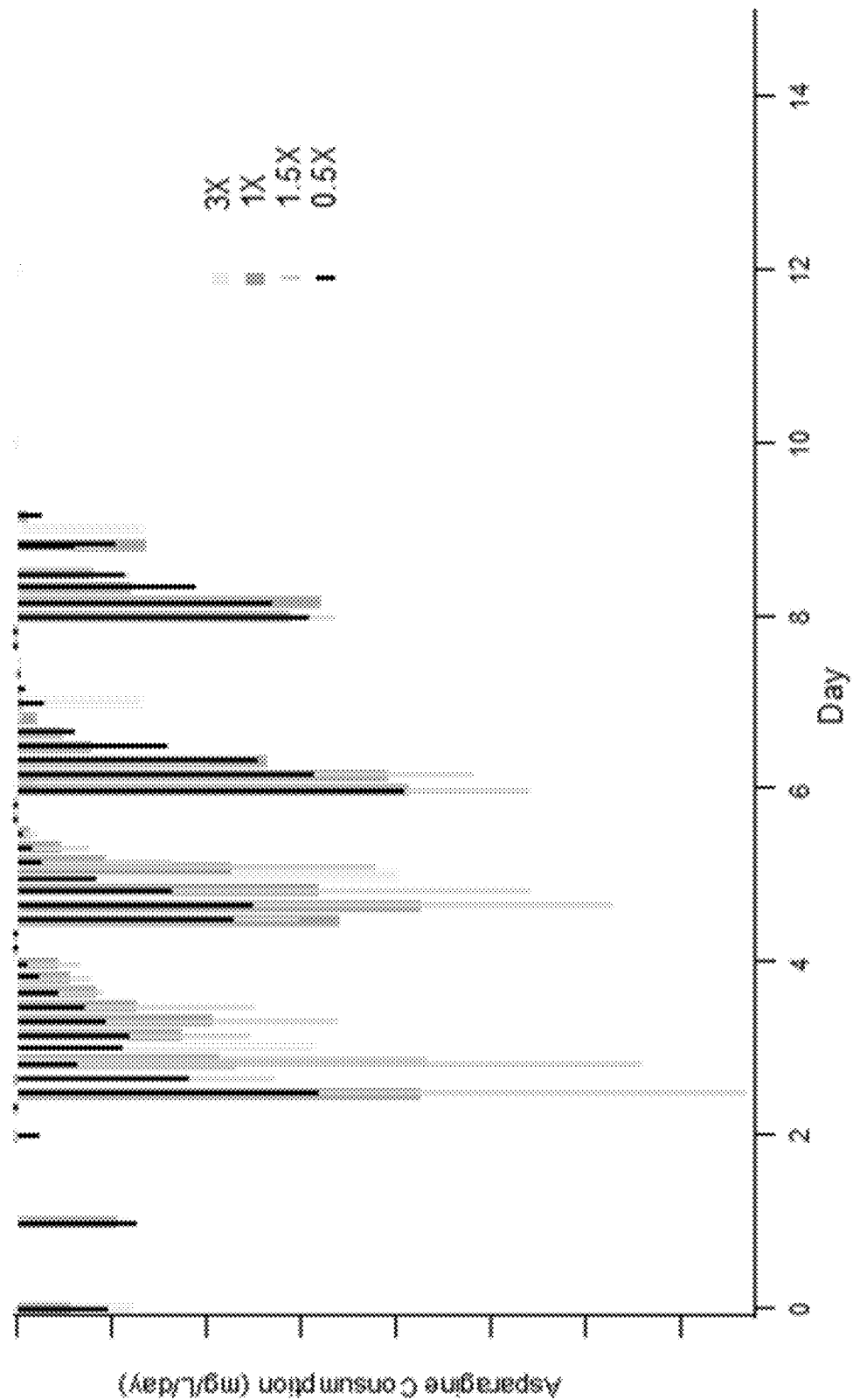
FIG. 7 illustrates asparagine consumptions rates over a range of asparagine feeding strategies for an exemplary high consuming cell line, in accordance with embodiments of the disclosure.

In this regard, FIG. 7 illustrates asparagine consumptions rates over a range of asparagine feeding strategies for an exemplary high consuming cell line. As shown, a new platform feed strategy of the disclosure results in a fed-batch cell culture that consumes less asparagine over the duration of the cell culture, as compared to a prior, known platform feed strategy. Further, as shown, high asparagine feed strategies result in higher asparagine consumption rates, as compared to low asparagine feed strategies. This data suggests that a new platform feed strategy of the disclosure provides for the most efficient use of asparagine.

In summary, Asparagine was identified to be depleted in high consuming cell lines. Supplementation in early fed-batch cell culture impacts cell culture performance. Supplementation in late fed-batch cell culture increases by-product, e.g., ammonium, production. It was unexpectedly found that a balanced asparagine feed strategy that prevents essential amino acid depletions, overcomes asparagine depletions in early fed-batch and minimizes ammonium impact, results in increased cell culture productivity Example 2—Influence of Asparagine in Fed-Batch Cell Culture on Asparagine Related Amino Acids The inter-relation between asparagine and non-essential amino acids related to asparagine through metabolic pathways may be investigated using an AMBR250 bioreactor system and amino acid measurements, as described herein.

Figure 8:
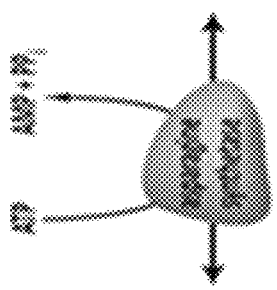
FIG. 8 illustrates the synthesis pathway for asparagine utilizing aspartate and glutamate.
Figure 9A:
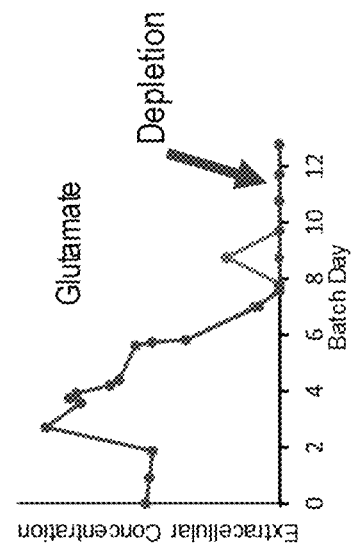
FIGS. 9A-9D, illustrate the effect of asparagine levels in late fed-batch cell culture of an exemplary high consuming cell line, in accordance with embodiments of the disclosure, with FIGS. 9A-9B showing extracellular asparagine (FIG. 9A) and extracellular glutamate (FIG. 9B) concentrations, and FIGS. 9C-9D showing intracellular asparagine (FIG. 9C) and intracellular glutamate (FIG. 9D) concentrations.
Figure 9B:
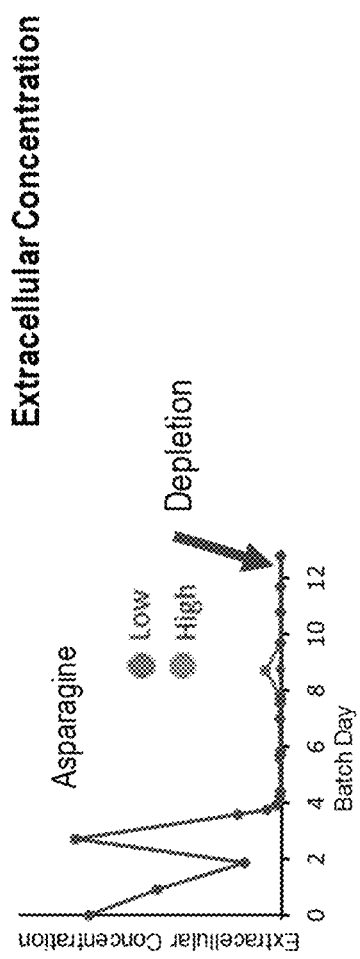
Figure 9C:
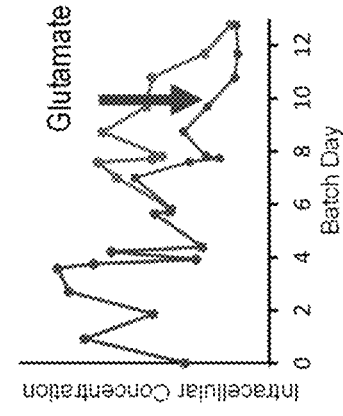
Figure 9D:
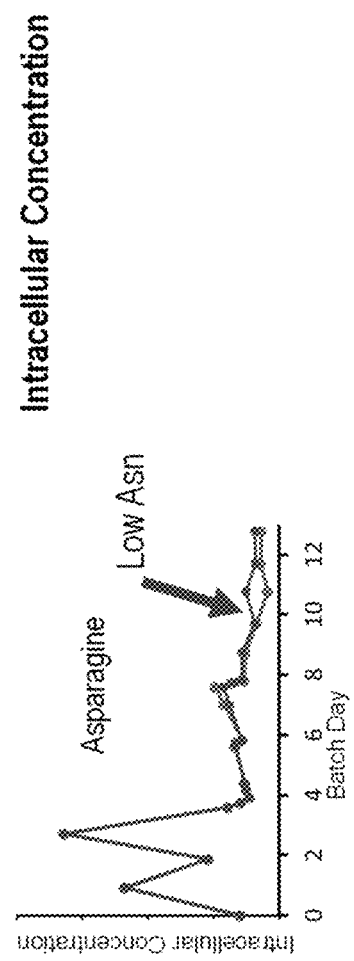

With reference to FIG. 8, if asparagine is needed, cells may increase their utilization of aspartate and glutamate to synthesize supplemental asparagine. Higher intracellular/extracellular concentrations of aspartate, glutamate and glutamine may indicate that the cells have enough intracellular asparagine to support cellular needs. However, decreases in concentrations of aspartate, glutamate, and glutamine could indicate asparagine limitations.

With reference to FIGS. 9A-9D, the effect of asparagine levels in late fed-batch cell culture of an exemplary high consuming cell line 1 is illustrated. As shown, low asparagine impacts the intracellular profile of a related non-essential amino acid (intracellular glutamate decreases with low asparagine).

With reference to FIGS. 10A-10D, the effect of asparagine levels in late fed-batch cell culture of another exemplary high consuming cell line 2 is illustrated. As shown, low asparagine impacts the intracellular profile of a related non-essential amino acid (intracellular glutamate decreases with low asparagine), however, to a lesser extent than that observed with exemplary high consuming cell line 1.

With reference to FIGS. 11A-11D, the effect of asparagine levels in late fed-batch cell culture of an exemplary low consuming cell line is illustrated. As shown, low asparagine does not impact extracellular or intracellular profiles of a related non-essential amino acid for this exemplary cell line (intracellular profiles for glutamate does not decrease with low asparagine). As shown, there are high levels of intracellular asparagine and glutamate at the end of the fed-batch cycle.

Finally, as shown in FIGS. 12A-12F, the effect of high (3× early stage, 1.5× late stage), and very high (6× early stage, 3× late stage), which shows that increases in extracellular asparagine can increase asparagine related amino acids, but can also impact titer and ammonium levels. As shown, higher levels of supplemental asparagine (FIG. 12A) can result in increases of asparagine related amino acids (FIGS.

Figure 12A:
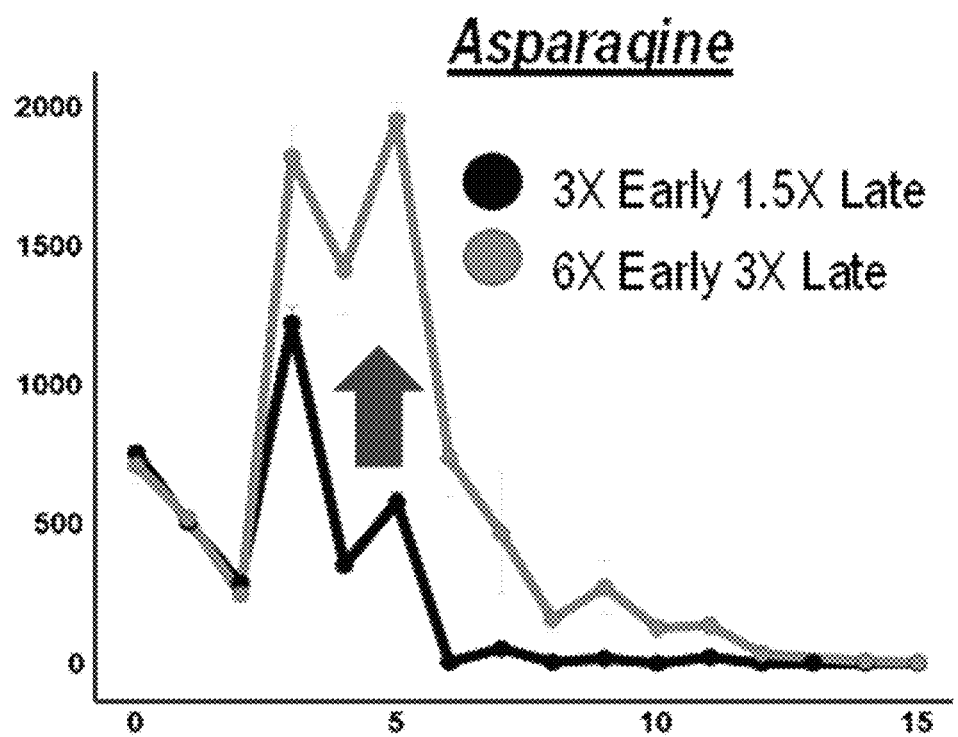
FIGS. 12A-12F, illustrate the effect of high (3× early stage, 1.5× late stage), and very high (6× early stage, 3× late stage) asparagine levels in fed-batch cell culture, in accordance with embodiments of the disclosure, with FIG. 12A showing asparagine concentrations, FIG. 12B showing aspartate concentrations FIG. 12C showing titer, FIG. 12D showing glutamate concentrations, FIG. 12E showing glutamine concentrations, and FIG. 12F showing ammonium concentration.
Figure 12B:
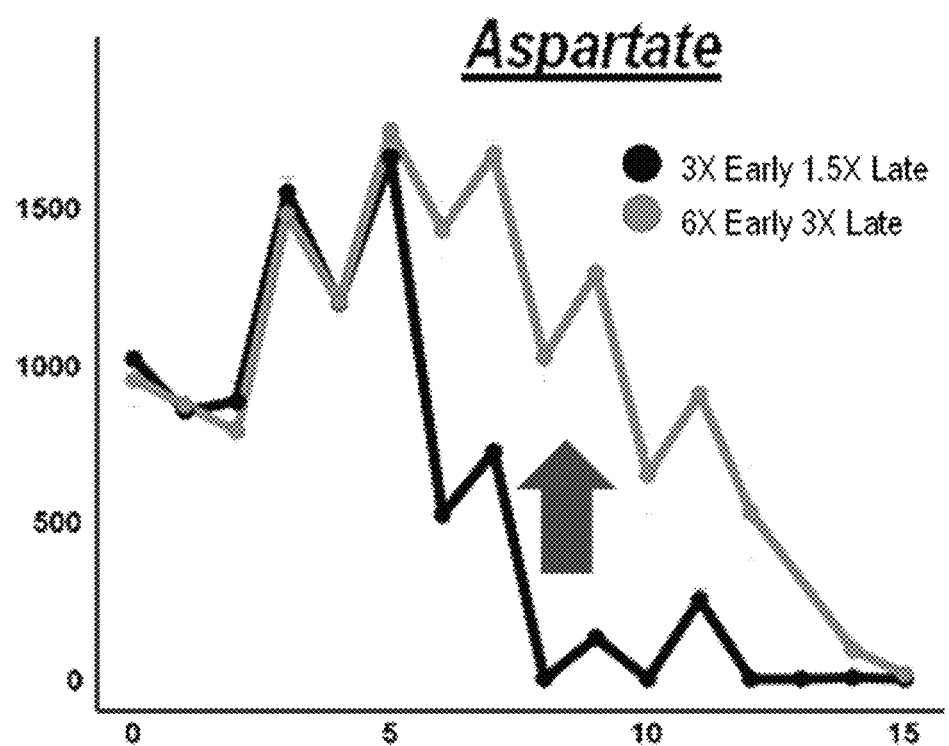
Figure 12C:
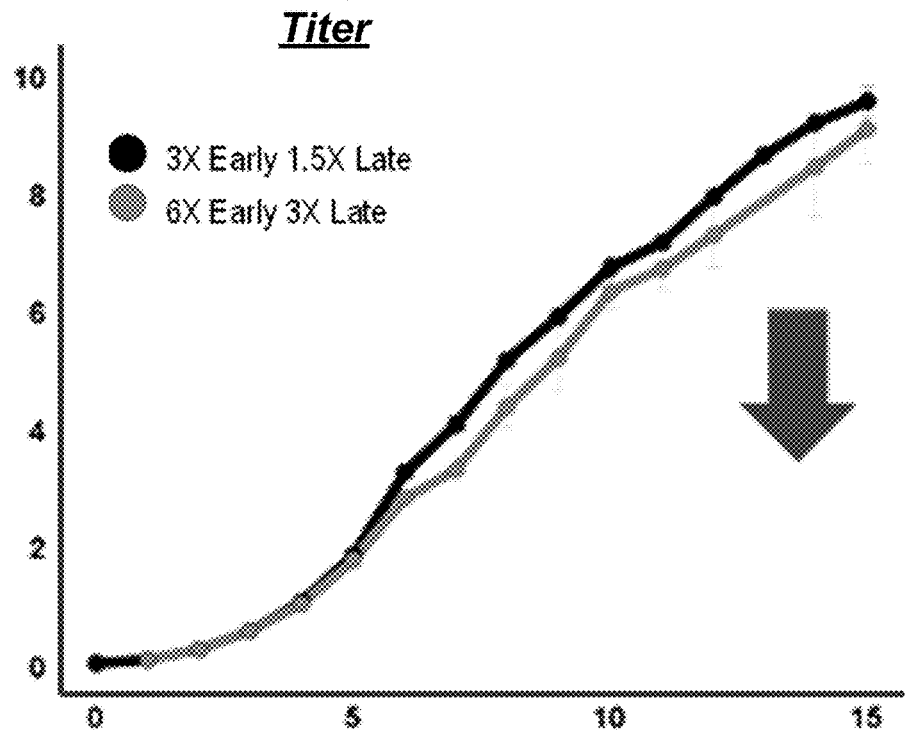
Figure 12D:
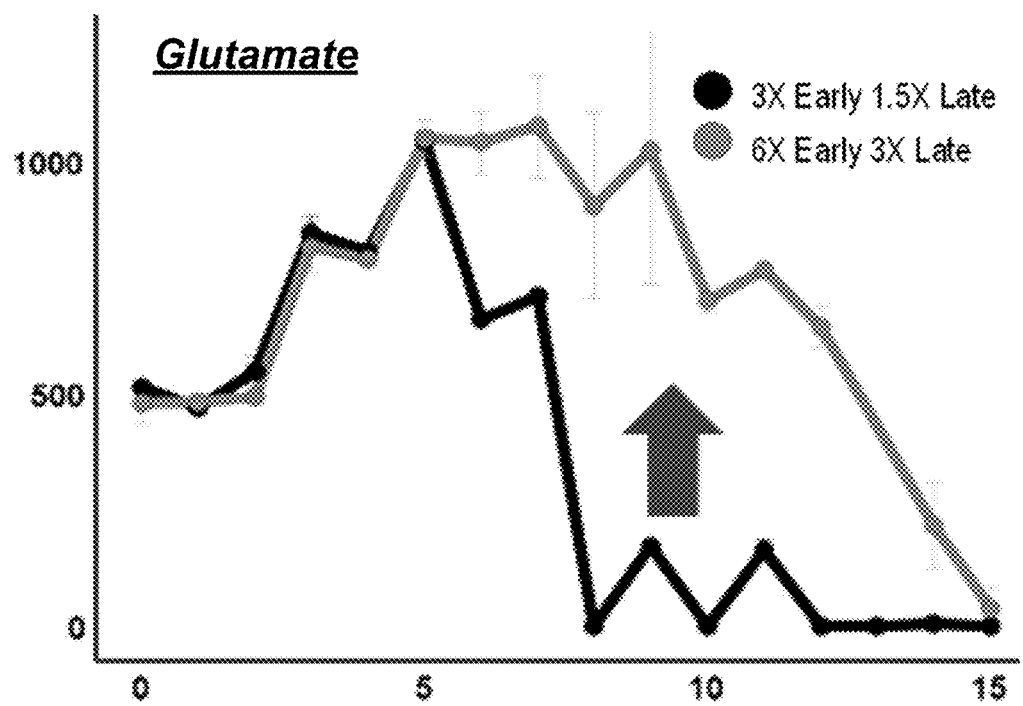
Figure 12E:
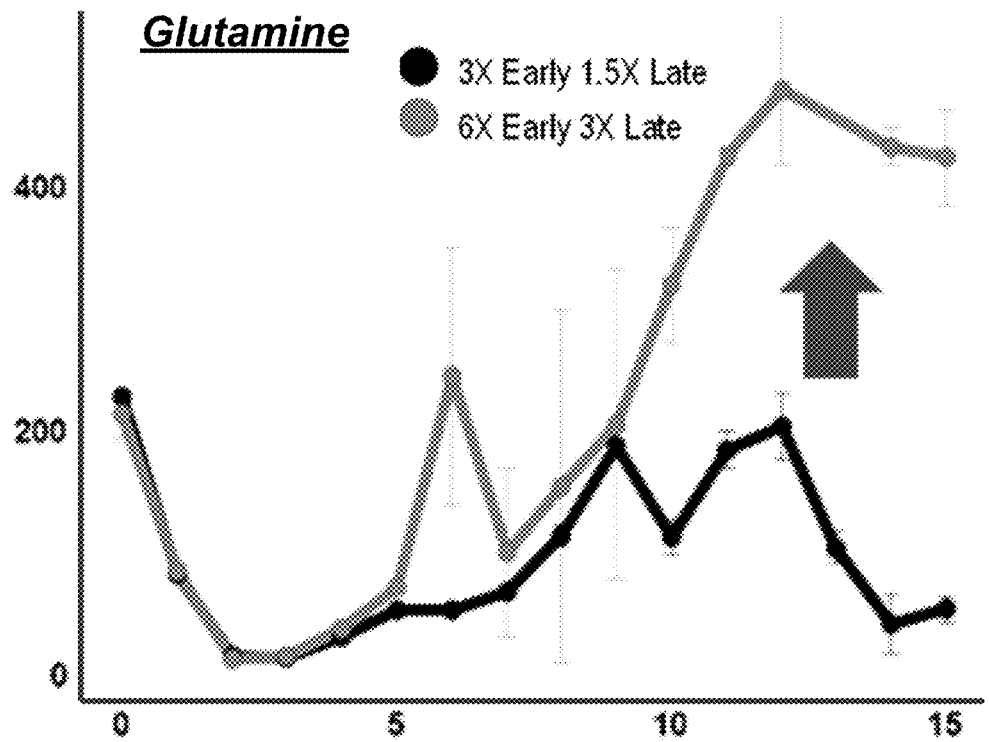
Figure 12F:
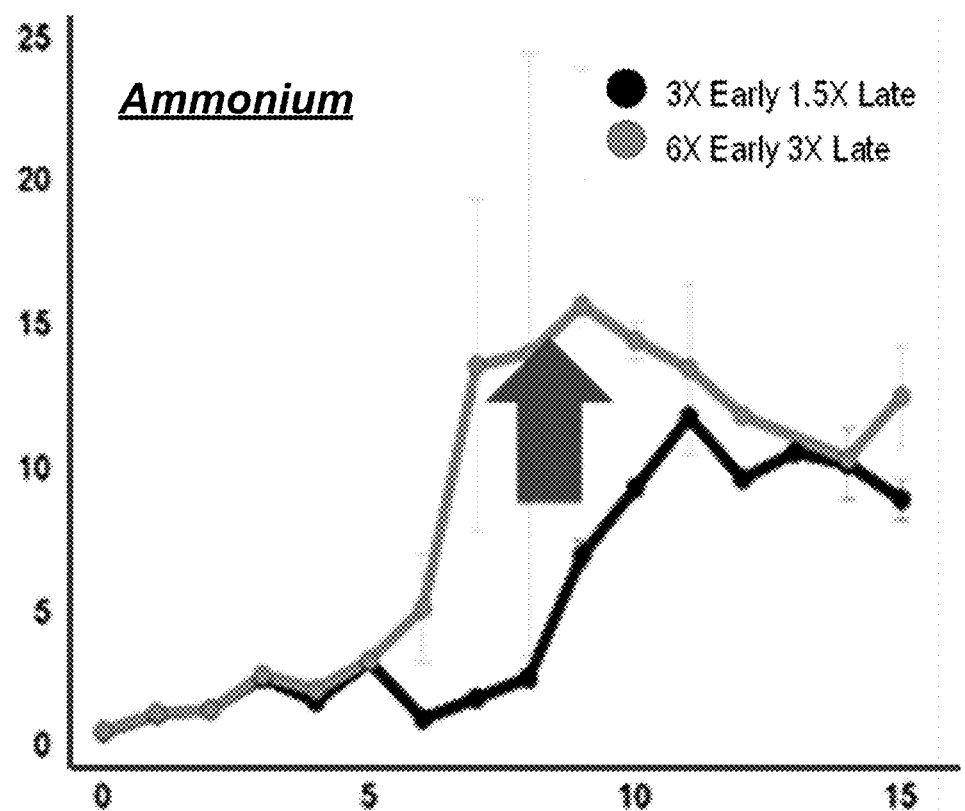

12B, 12D, and 12E), but the resulting increases in undesired cell culture by-products (i.e., FIG. 12F, ammonium) can result in declines in cell culture performance (i.e., FIG. 12C, titer).

Together FIGS. 9A-9D, FIGS. 10A-10D, FIGS. 11A-11D, and FIGS. 12A-12F illustrate that asparagine related amino acid profiles and cell culture performance for different asparagine feed levels vary by cell line, suggesting that asparagine feed requirements may be targeted to the specific needs of a cell line.

In summary, intracellular concentrations of asparagine related amino acids suggest specific asparagine requirements for a particular cell line. More specifically, the impact of asparagine supplementation on extracellular and intracellular amino acid profiles of related amino acids can be targeted to the specific needs of a cell line.

Example 3—Overcoming Asparagine Depletions

Improved asparagine feeding strategies and platforms optimized to overcome asparagine depletions while maintaining cell culture performance may be developed using an AMBR250 bioreactor system and amino acid measurements, as described herein.

Table 1 below illustrates exemplary asparagine feeding strategies investigated.

TABLE 1

| Feeding Approach | Bulk Feed | Asn Feed |
|---|---|---|
| Standard fed-batch (bolus) | Bolus | Bolus |
| Continuous separate Asn Feed | Bolus | Continuous |
| Continuous bulk + Asn Feed | Continuous | Continuous |
| Hybrid Feed | Bolus | Bolus (1X) + Continuous (1X) |

As shown in Table 1, a standard fed-batch bolus asparagine feed was compared to several asparagine feed strategies, i.e., a continuous asparagine supplement feed (separate from bolus cell culture bulk feeds), a continuous combined bulk plus asparagine feed, and a hybrid feed strategy utilizing both a bolus asparagine feed and a continuous asparagine supplement feed (separate from bolus cell culture bulk feeds), such that twice the total asparagine supplement amount is provided to the cell culture.

With reference to FIGS. 13A-13D, it was found that bolus and continuous asparagine feeds have comparable cell culture performance (viable cell count illustrated in FIG. 13A, culture productivity illustrated in FIG. 13B) for the same total asparagine supplement amounts. Further, cell culture byproduct formation (FIG. 13C illustrates ammonium formation, FIG. 13D illustrates alanine formation) is relatively constant in bolus and continuous asparagine feeds. However, with reference to FIGS. 13E-13G, continuous asparagine supplement feed delays extracellular asparagine (FIG. 13E), aspartate (FIG. 13F) and glutamate (FIG. 13G) depletions, in comparison to bolus asparagine supplement feeds having the same total asparagine supplement amounts. In accordance with aspects of the disclosure, it was unexpectedly found that the same total asparagine supplement amount when fed continuously, decreases consumption rates of asparagine, aspartate and glutamate. In this regard, improved amino acid depletion profiles with comparable cell culture performance suggest more efficient asparagine consumption by the cell culture.

Figure 14B:
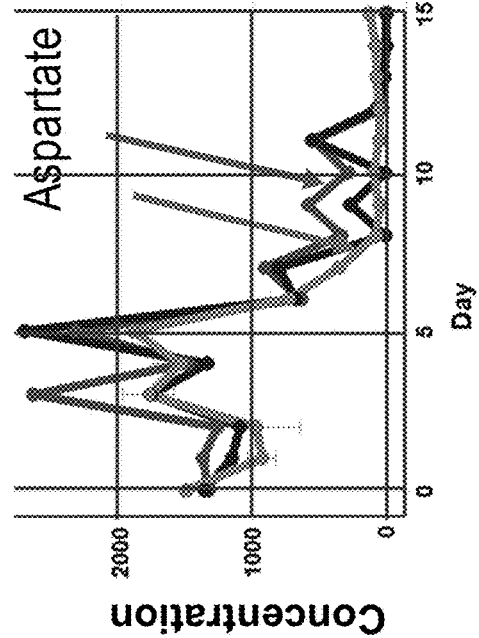
FIGS. 14A-14D, illustrate the effect of bolus and continuous asparagine feeds, in accordance with embodiments of the disclosure.
Figure 14D:
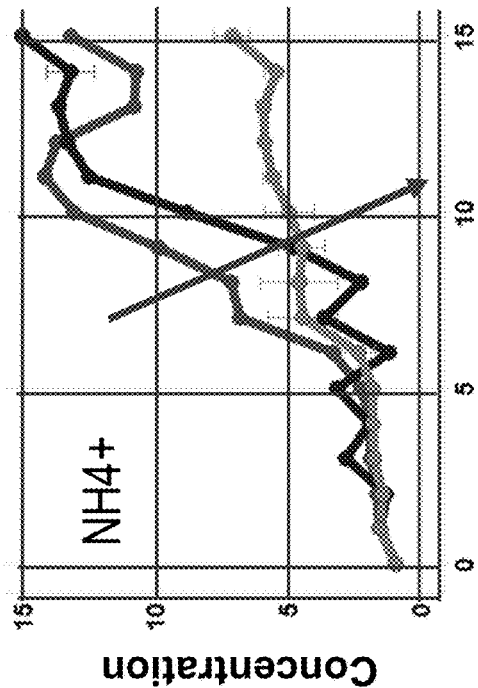
Figure 14A:
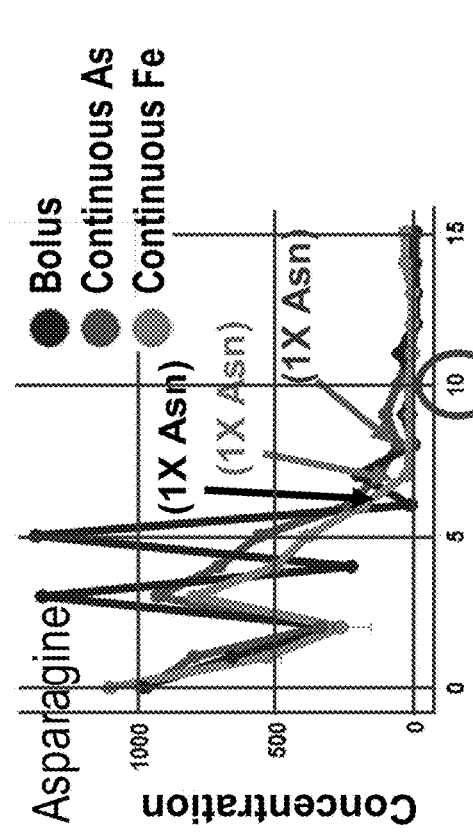
Figure 14C:
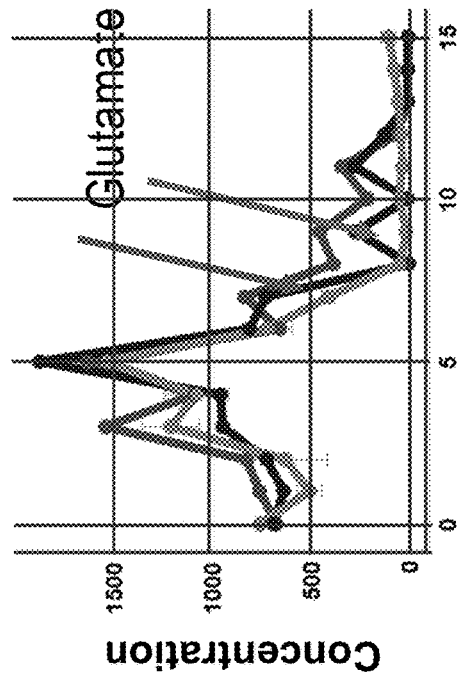

With reference to FIGS. 14A-14D, it was found that supplementation of asparagine via continuous independent asparagine feed (separate from bolus bulk feed), as compared to continuous supplementation of asparagine via continuous bulk feed and standard bolus supplementation, does not prevent extracellular asparagine depletions for the same total asparagine supplement amount (FIG. 14A), but does reduce cell culture by-product formation (FIG. 14D) and modulate consumption rates of asparagine related metabolites (FIG. 14B and FIG. 14C). All illustrated feed strategies have comparable cell culture performance.

A hybrid feed approach (continuous asparagine supplement feed in combination with bolus asparagine supplement feed) was found to delay amino acid depletions, but to increase by-product formation across multiple exemplary cell lines, as compared to bolus asparagine supplementation.

Figure 15A:
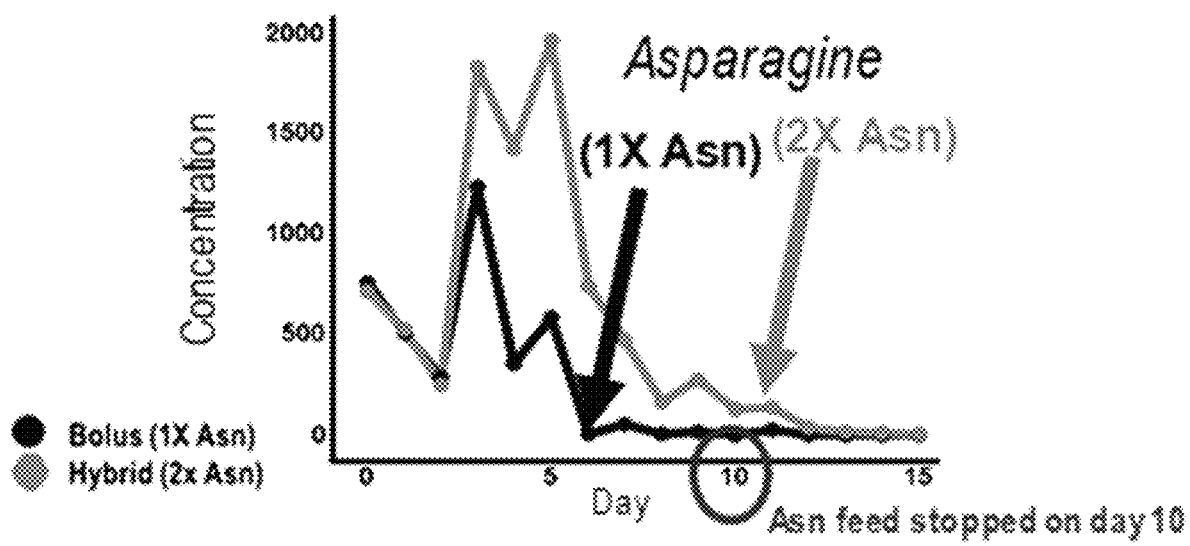
FIGS. 15A-15G, illustrate a hybrid feed approach (continuous asparagine supplement feed in combination with bolus asparagine supplement feed) in an exemplary cell line, in accordance with an embodiment of the disclosure, with FIG. 15A illustrating extracellular asparagine, FIG. 15B illustrating extracellular aspartate, FIG. 15C illustrating extracellular glutamate, FIG. 15D illustrating viable cell count, FIG. 15E illustrating titer, FIG. 15F illustrating ammonium formation, and FIG. 15G illustrating alanine formation.
Figure 15B:
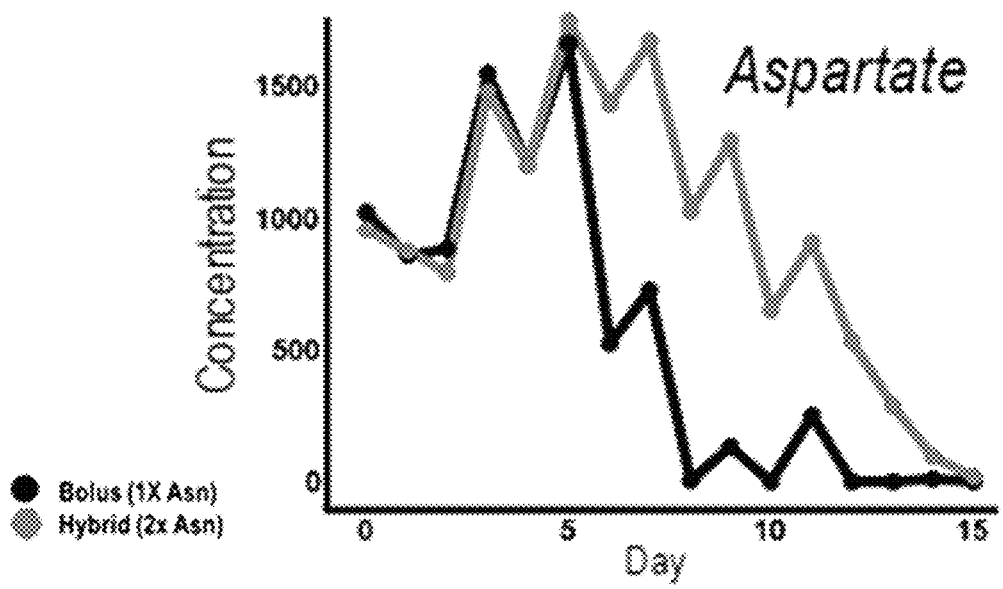
Figure 15C:
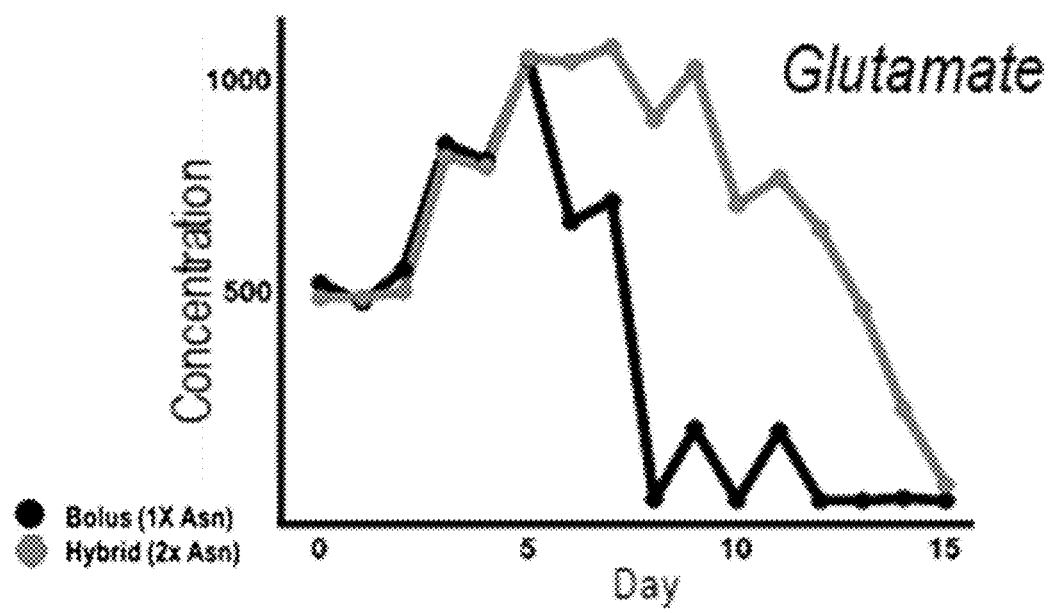
Figure 15D:
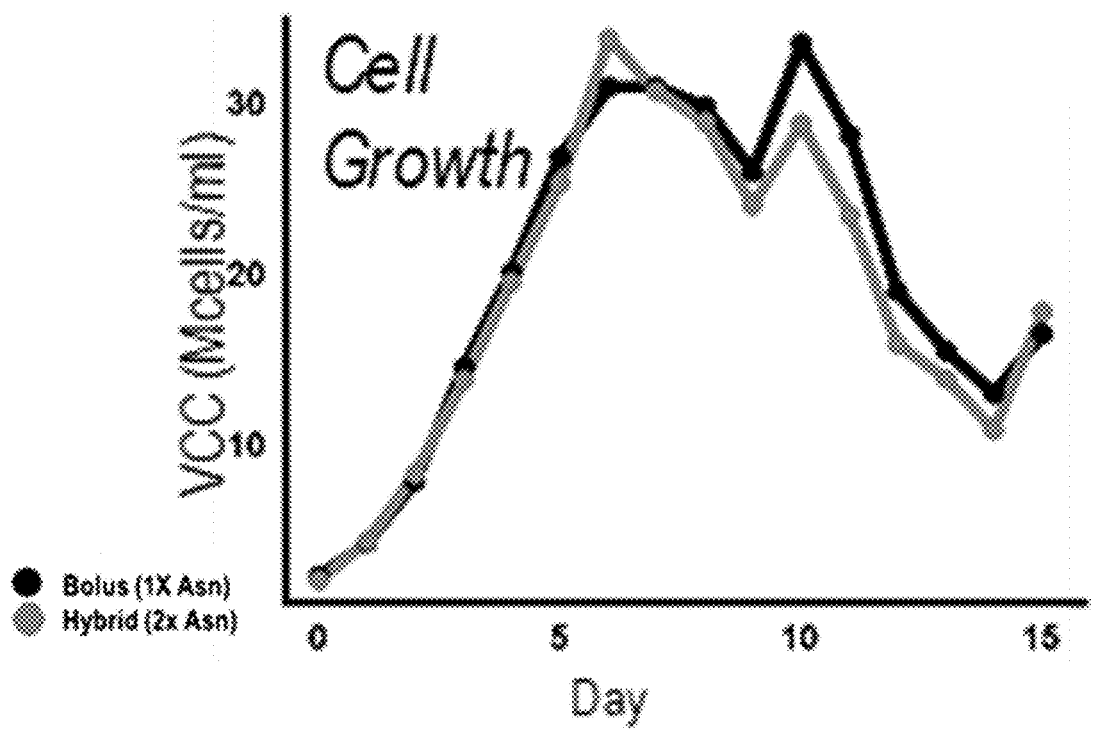
Figures 15E, 15F:
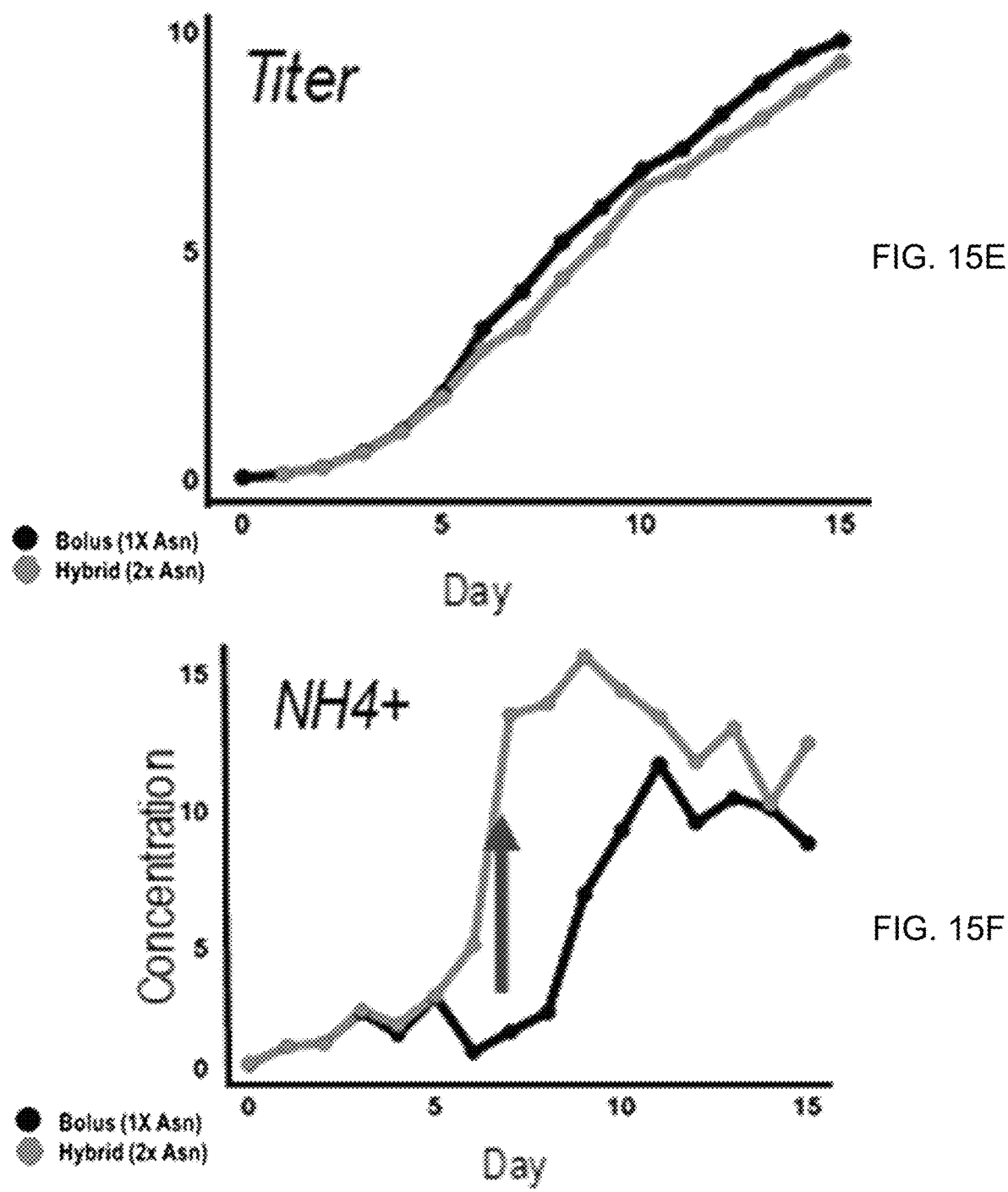
Figure 15G:
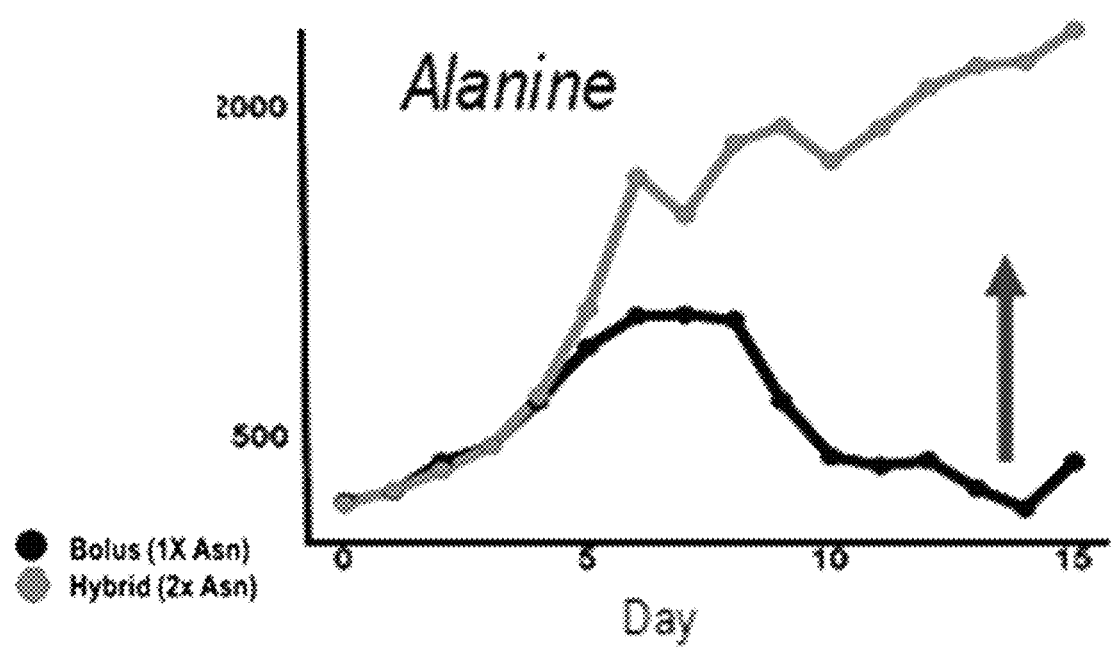

With reference to FIGS. 15A-15G, in a first exemplary cell line, a hybrid feed approach was found to delay asparagine and related metabolite depletion (FIG. 15A illustrating extracellular asparagine, FIG. 15B illustrating extracellular aspartate, and FIG. 15C illustrating extracellular glutamate), and resulted in comparable cell culture performance (viable cell count illustrated in FIG. 15D, culture productive illustrated in FIG. 15E), but was also found to increase by-product formation (FIG. 15F illustrates ammonium formation, FIG. 15G illustrates alanine formation).

With reference to FIGS. 16A-16E, in a second exemplary cell line, a hybrid feed approach was found to delay asparagine (FIG. 16A illustrating extracellular asparagine), but resulted in a decrease in cell culture productivity (viable cell count illustrated in FIG. 16B, culture productive illustrated in FIG. 16C). The hybrid feed approach was also found to increase by-product formation (FIG. 16D illustrates ammonium formation, FIG. 16E illustrates alanine formation).

In summary, the impacts of extracellular asparagine depletions in late fed-batch were addressed by identifying new asparagine supplement feed strategies. It was unexpectedly found that continuous asparagine supplementation is a more efficient platform for feeding asparagine. Continuous asparagine supplementation, particularly as an independent, separate asparagine feed, decreases consumption rates of asparagine and related metabolites.

Example 4—Mitigating and Controlling Asparagine Sequence Variants in Fed-Batch Cell Culture and Use of Asparagine Related Amino Acids as Surrogate Markers of Asparagine Sequence Variants The use of asparagine supplements to mitigate asparagine sequence variants, and the use of asparagine related amino acids as surrogate markers for asparagine sequence variants in a polypeptide of interest may be investigated using an AMBR250 bioreactor system and amino acid measurements, as described herein.

Figures 10A, 10B:
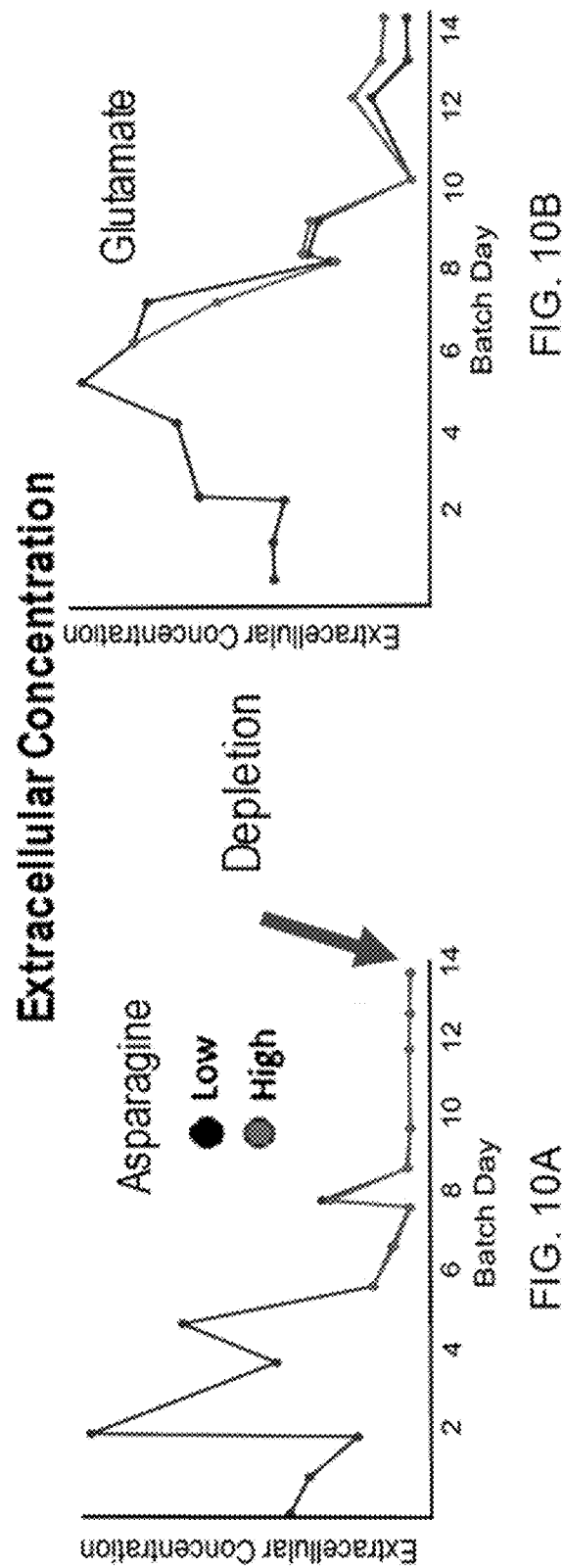

Referring back to FIGS. 10A-10D, illustrating the effect of asparagine levels in late fed-batch cell culture of an exemplary high consuming cell line 2, asparagine sequence variants were analyzed by mass spec on the last day of the fed batch cell culture. The low asparagine supplemented cell culture was found to have 0.30% asparagine sequence variant present, and the high asparagine supplemented cell culture was found to have 0.24% asparagine sequence variant present. These SV values are relatively low, and are in agreement with the higher levels of intracellular glutamate observed in the cell culture, as illustrated in FIG. 10D.

Similarly, with reference to FIGS. 11A-11D, illustrating the effect of asparagine levels in late fed-batch cell culture of an exemplary low consuming cell line, asparagine sequence variants were analyzed by mass spec on the last day of the fed batch cell culture. The low asparagine supplemented cell culture was found to have 0.11% asparagine sequence variant present, and the high asparagine supplemented cell culture was found to have 0.04% asparagine sequence variant present. Again, these SV values are relatively low, and are in agreement with the higher levels of intracellular glutamate observed in the cell culture, as illustrated in FIG. 11D.

Figure 17A:
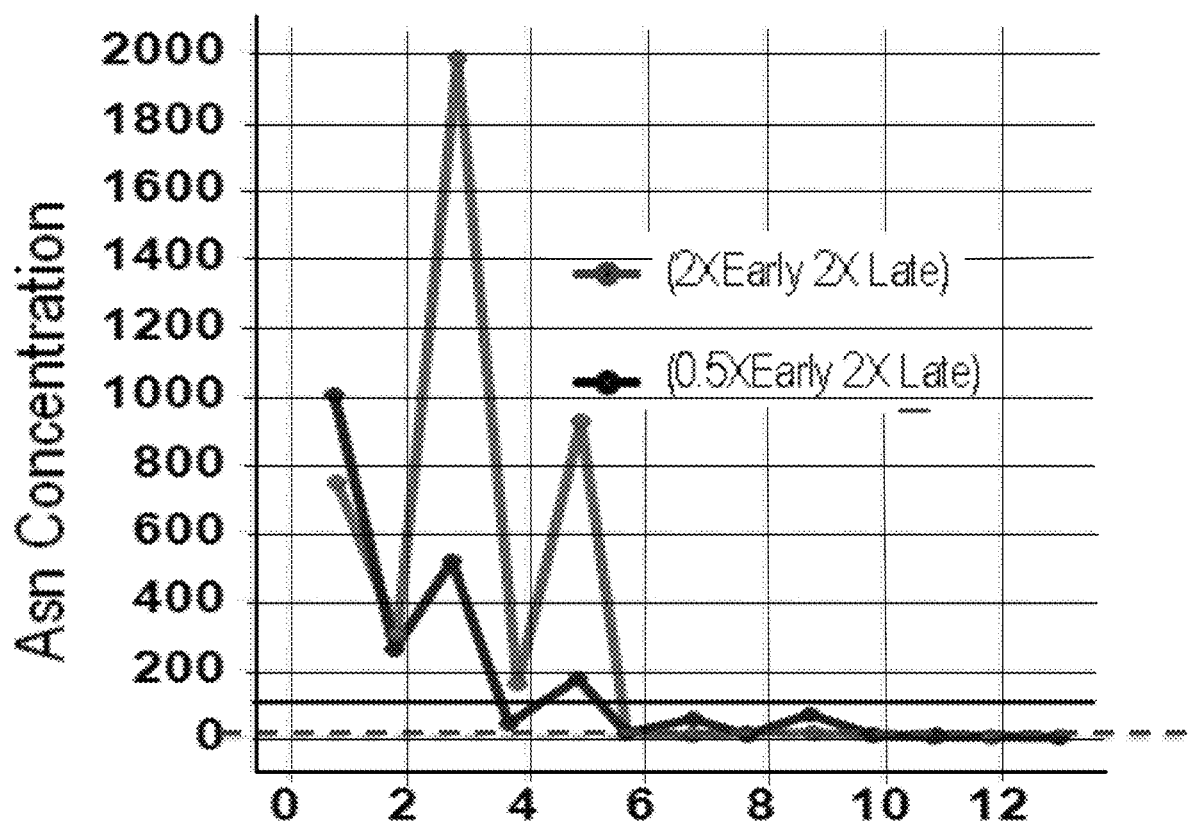
FIG. 17A, illustrates asparagine consumption in fed-batch cell culturing following asparagine feed strategies, in accordance with embodiments of the disclosure, with FIG. 17B showing the mitigation of the formation of asparagine sequence variants.
Figure 17B:
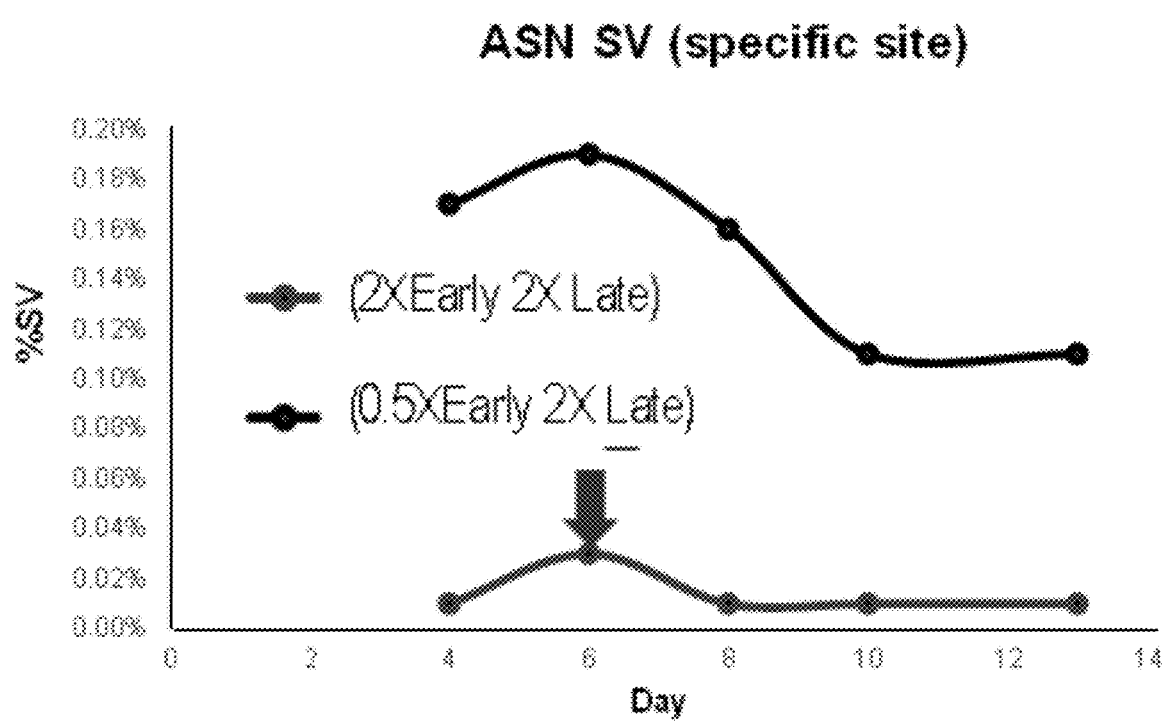

With reference to FIG. 17A-17B, it has been found that extracellular asparagine depletion in early stage fed-batch can be an indicator of Asn→Ser, asparagine sequence variant formation. As shown in FIG. 17A, high asparagine feed strategies (3× early stage @ 10.8 mM, 1.5× late stage) that maintain extracellular asparagine levels above a depletion limit of 0.1 mM (15 mg/L) until at least day 4 of early stage cell culture (e.g., through feed 2) are able to mitigate formation of asparagine sequence variants to levels below about 0.20% SV (FIG. 17B).

Figure 18A:
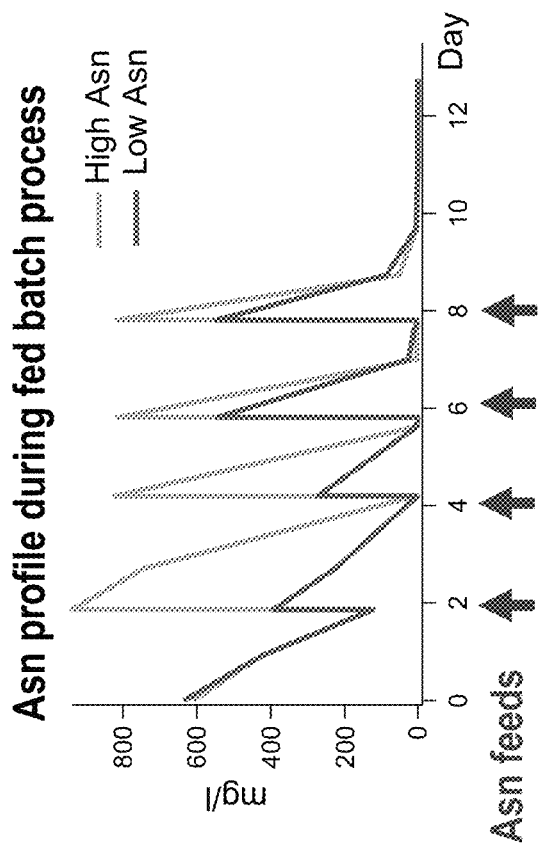
FIG. 18A, illustrates asparagine consumption in fed-batch cell culturing following asparagine feed strategies, in accordance with embodiments of the disclosure.
Figure 18B:
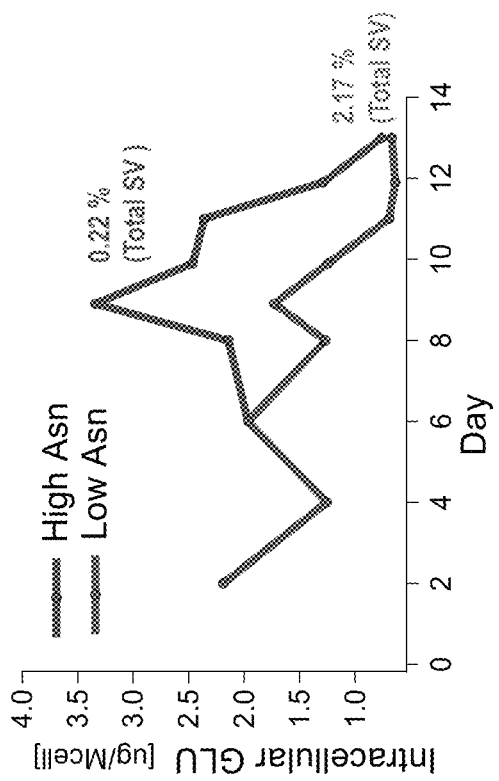
FIG. 18B illustrates intracellular glutamate levels, with FIG. 18C showing the mitigation of the formation of asparagine sequence variants, in accordance with embodiments of the disclosure.
Figure 18C:
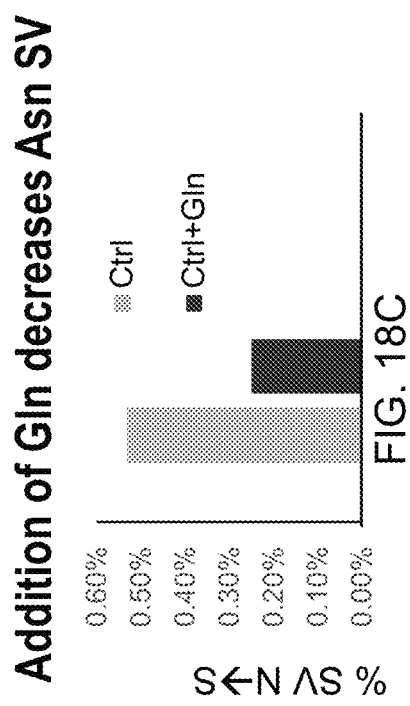

With reference to FIG. 18A, it has been found that lower asparagine levels in late feeds increase Asn→Ser, asparagine sequence variants, particularly after peak viable cell concentration. In the experiment depicted in FIG. 18A, asparagine levels in the early feeds were the same. FIG. 18B illustrates intracellular glutamate (Glu) levels for the high asparagine late feed strategy compared to the low asparagine late feed strategy. Further, it was unexpectedly found that the addition of Gln to the cell culture medium further mitigated the formation of asparagine sequence variants (FIG. 18C).

As shown, intracellular glutamate concentrations are inversely correlated with the presence of asparagine sequence variants. Higher intracellular glutamate levels are found in cell cultures with lower occurrences of asparagine sequence variants, and lower intracellular glutamate levels are found in cell cultures with higher occurrences of asparagine sequence variants. In this way, intracellular glutamate may be used as a surrogate marker of asparagine sequence variant amounts in a polypeptide of interest.

Figure 19A:
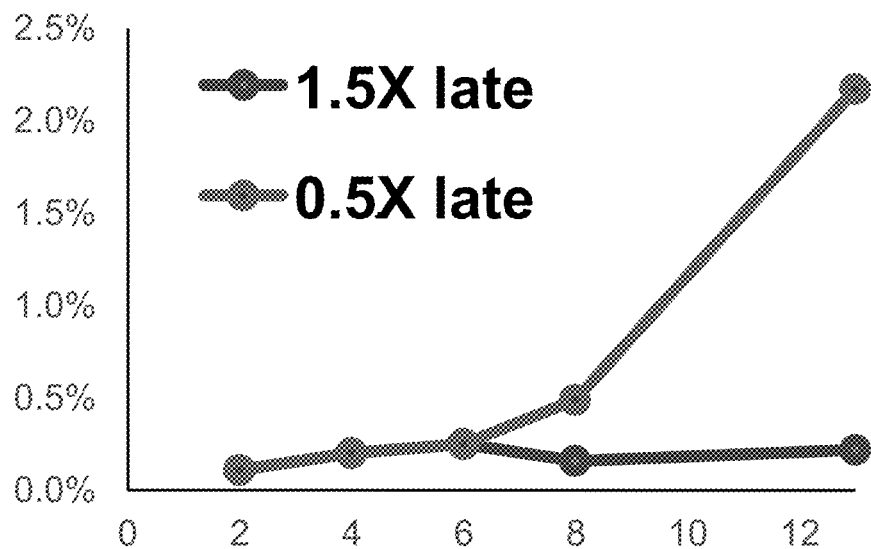
FIGS. 19A-19G illustrate correlations between asparagine, asparagine related amino acids and asparagine sequence variants for an exemplary cell line, in accordance with embodiments of the disclosure.
Figure 19B:
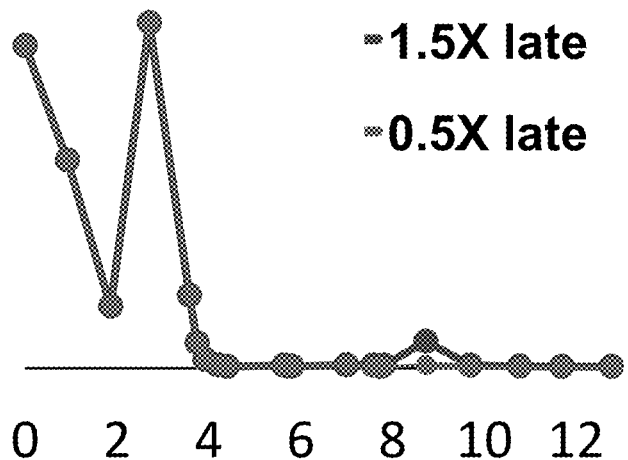
Figure 19C:
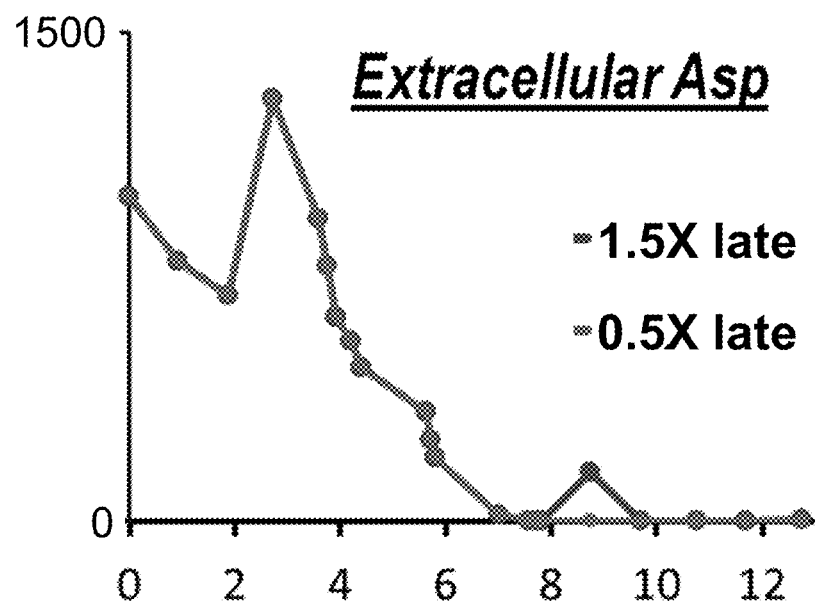
Figure 19D:
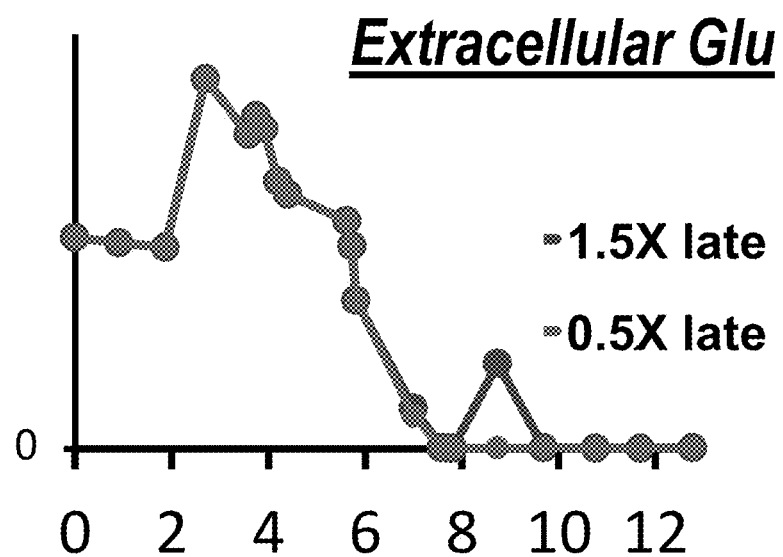
Figure 19E:
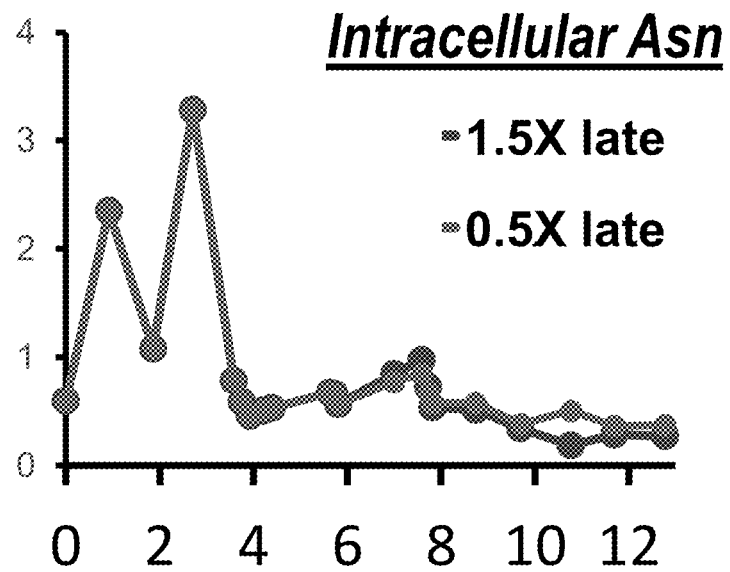
Figure 19F:
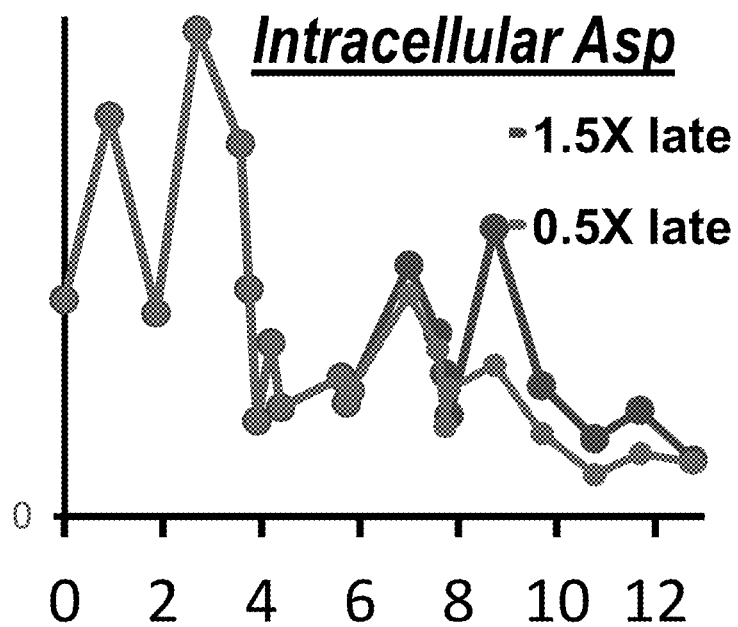
Figure 19G:
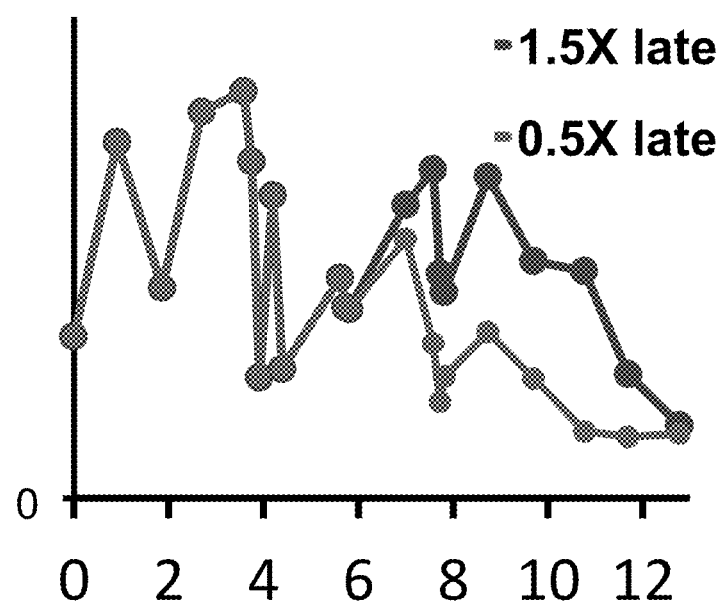

FIGS. 19A-19G illustrate correlations between asparagine, asparagine related amino acids and asparagine sequence variants for an exemplary cell line 1. FIGS. 19B-19D illustrate extracellular asparagine (FIG. 19B), aspartate (FIG. 19C), and glutamate (FIG. 19D), while FIGS. 19E-19G illustrate exemplary intracellular asparagine (FIG. 19E), aspartate (FIG. 19F), and glutamate (FIG. 19G). FIG. 19G illustrates that late stage fed-batch intracellular glutamate (Glu) can serve as a surrogate marker of asparagine sequence variants for a polypeptide produced using the high and low asparagine feed strategies of FIG. 19A. As shown, the high asparagine supplement feed results in high late stage fed-batch intracellular glutamate, and low asparagine sequence variants. The low asparagine supplement feed results in low late stage intracellular glutamate, and higher asparagine sequence variants. The surrogate intracellular glutamate measurements are in agreement with the mass spec asparagine sequence variant analysis. However, there is no clear trend regarding extracellular or intracellular asparagine or aspartate, or extracellular glutamate for this particular cell line.

FIGS. 20A-20D illustrate similar correlations between asparagine, asparagine related amino acids and asparagine sequence variants for another exemplary cell line (high consuming cell line). FIGS. 20B-20D illustrate extracellular asparagine (FIG. 20B), intracellular aspartate (FIG. 20C), and intracellular glutamate (FIG. 20D). FIGS. 20C and 20D illustrate that late stage fed-batch intracellular aspartate and intracellular glutamate can both serve as a surrogate markers of asparagine sequence variants for a polypeptide produced using the high and low asparagine feed strategies of FIG. 20A. As shown, the high asparagine supplement feed results in high late stage fed-batch intracellular aspartate and high late-stage fed-batch intracellular glutamate, and low asparagine sequence variants. The low asparagine supplement feed results in low late stage fed-batch intracellular aspartate and low late stage fed-batch intracellular glutamate, and higher asparagine sequence variants. The surrogate intracellular aspartate and intracellular glutamate measurements are in agreement with the mass spec asparagine sequence variant analysis.

Figure 21E:
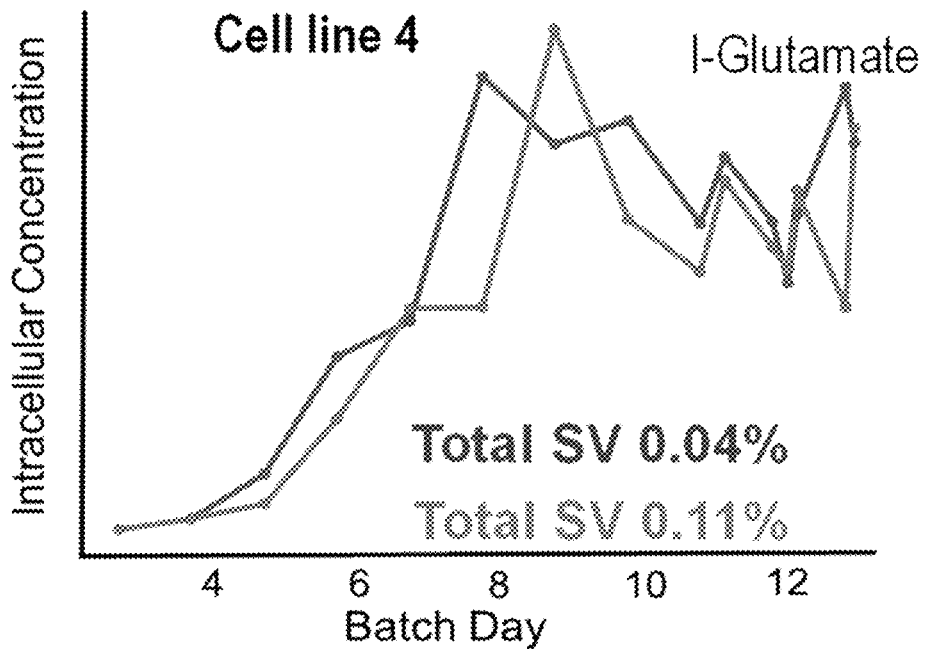
Figure 21F:
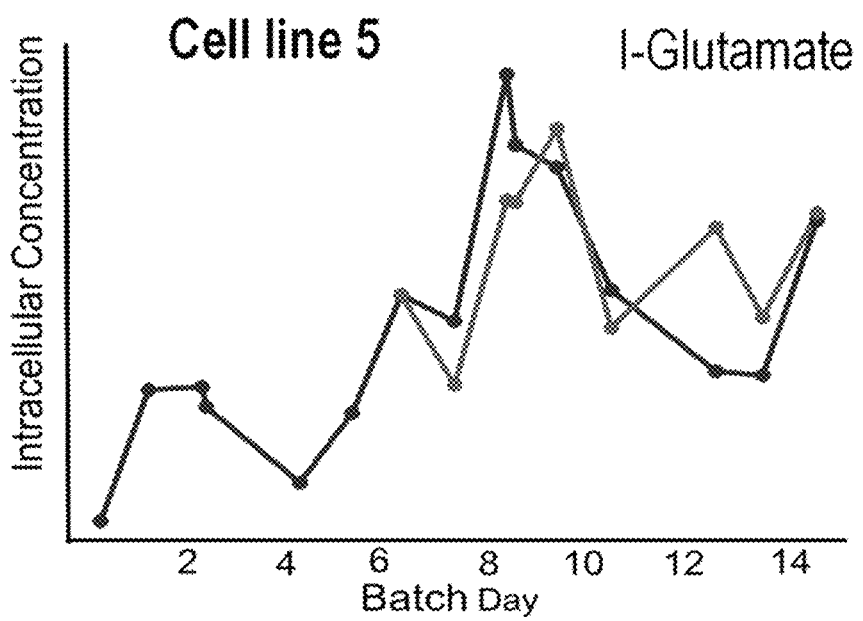

FIGS. 21A-21F illustrate that asparagine sequence variant trends for an exemplary cell line 1 agree with intracellular glutamate trends, showing that intracellular asparagine related amino acids can be used as surrogates of asparagine sequence variants. FIGS. 21A and 21C illustrate a high asparagine early feed strategy (FIG. 21A, sequence variant amounts as determined by mass spec, FIG. 21C, concentrations of intracellular glutamate). FIGS. 21B and 21D illustrate a low asparagine early feed strategy (FIG. 21B, sequence variant amounts as determined by mass spec, FIG. 21D, concentrations of intracellular glutamate). FIG. 21E shows intracellular glutamate levels for exemplary cell line 4 correlating with a higher occurrence and lower occurrence of asparagine sequence variants, with FIG. 21F showing a similar intracellular glutamate profile for another exemplary cell line 5.

FIGS. 22A-22H illustrate correlations between asparagine, asparagine related amino acids and asparagine sequence variants for exemplary cell lines. FIGS. 22A-22D illustrate extracellular asparagine (FIG. 22A), extracellular aspartate (FIG. 22B), extracellular glutamate (FIG. 22C) and extracellular glutamine (FIG. 22D) for exemplary cell line 1 for a high and low asparagine feed strategy. As shown, there is no clear trend observed for extracellular asparagine, aspartate, or glutamate and asparagine sequence variant formation. However, there is a correlation between late stage fed-batch extracellular glutamine and asparagine sequence variant formation (particularly assuming supplementation of asparagine above depletion limits in early stage fed-batch cell culture). A similar trend is shown in FIGS. 22E-22H for exemplary cell line 4, illustrating extracellular asparagine (FIG. 22E), extracellular aspartate (FIG. 22F), extracellular glutamate (FIG. 22G) and extracellular glutamine (FIG. 22H) for a high and low asparagine feed strategy.

Figure 23A:
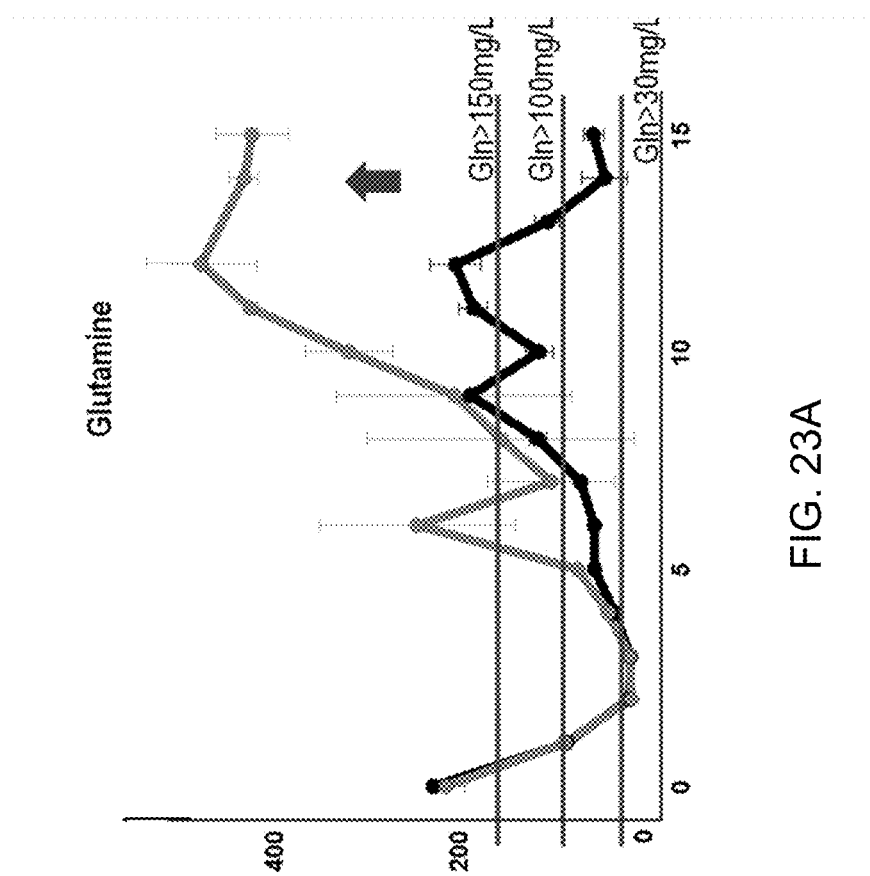
FIGS. 23A-23C further illustrate that extracellular glutamine can serve as a surrogate of asparagine sequence variants in late stage fed-batch cell culture.
Figure 23B:
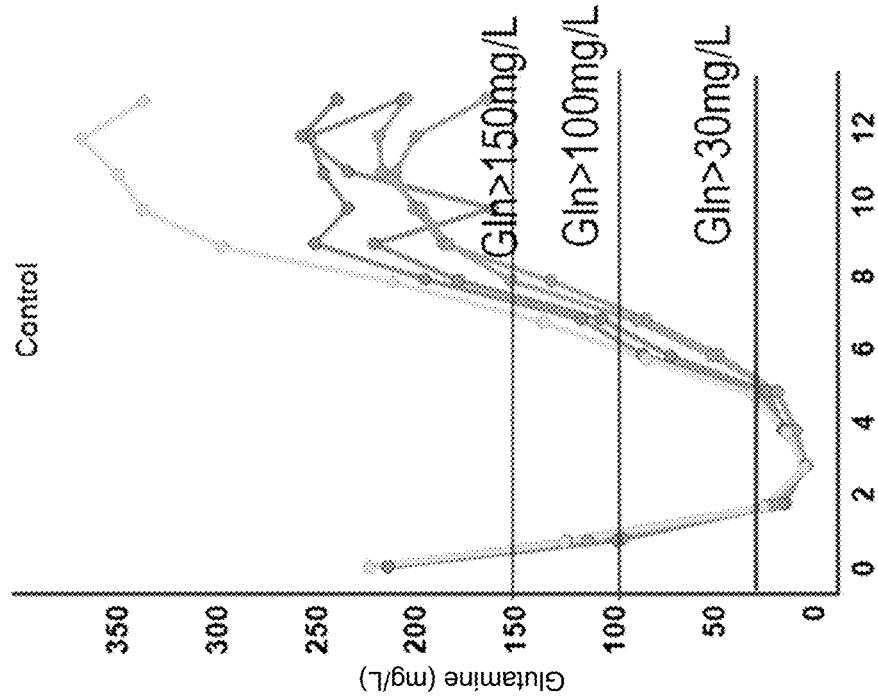
Figure 23C:
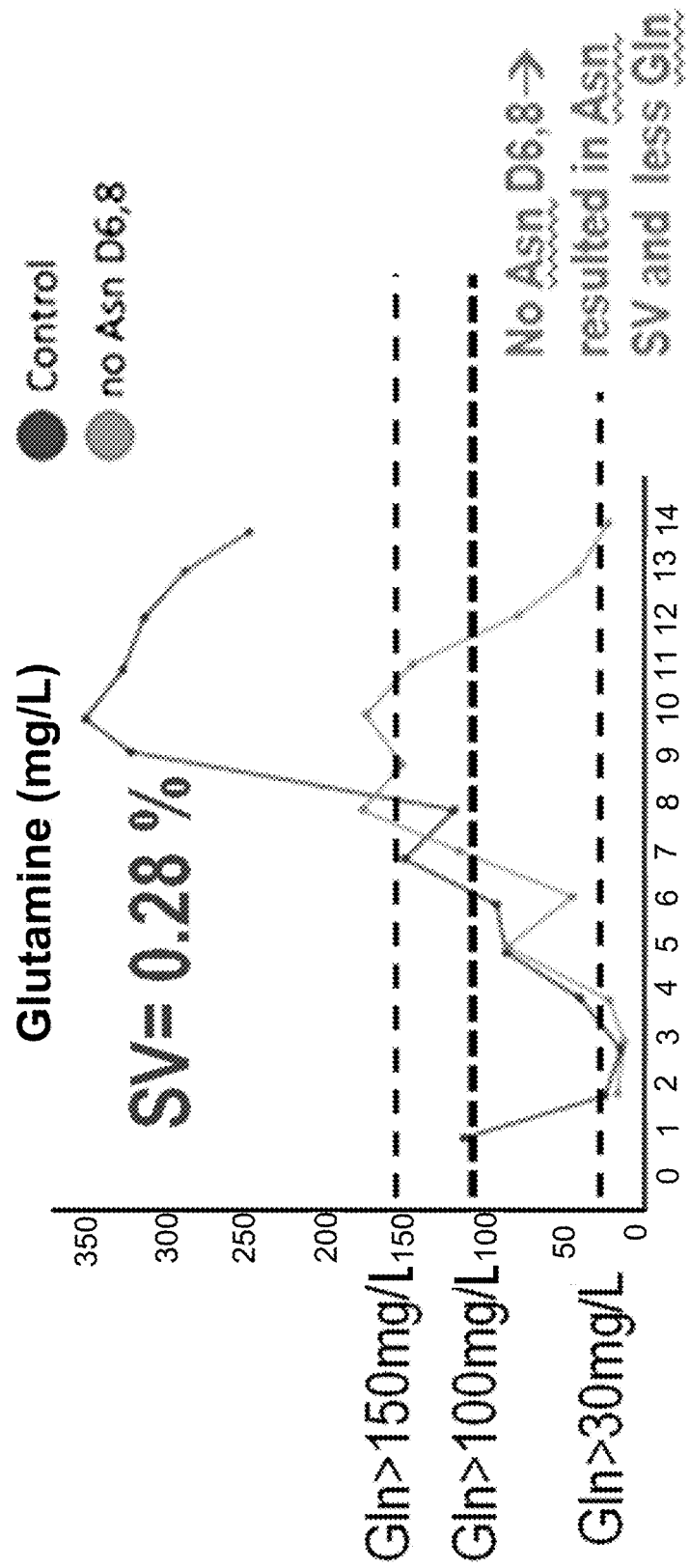

FIGS. 23A-23C further illustrate that extracellular glutamine can serve as a surrogate of asparagine sequence variants in late stage fed-batch cell culture. FIG. 23A shows that sufficient glutamine can be produced via high asparagine feed strategies in exemplary cell line 1 (e.g., above glutamine depletion limits). Similarly, FIG. 23B shows that sufficient glutamine can be produced via high asparagine feed strategies in exemplary cell line 1, correlating with embodiments wherein no asparagine sequence variant was detected by mass spec. And finally, FIG. 23C shows that when no asparagine is supplemented on day 6 and 8, asparagine sequence variants are detected and extracellular glutamine falls below depletion limits (i.e., insufficient glutamine is produced via asparagine feed strategies). However, when sufficient glutamine is produced via high asparagine feed strategies, extracellular glutamine correlates with asparagine sequence variant formation.

All publications and patent applications cited in this specification are herein incorporated by reference as if each individual publication or patent application were specifically, and individually, indicated to be incorporated by reference.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed:

1. A method for producing a recombinant protein of interest, the method comprising:
   propagating or maintaining CHO cells in a defined cell culture medium, wherein said CHO cells express a recombinant protein of interest;
   wherein the defined cell culture medium is supplemented with asparagine in an amount from about 3.6 mM to about 43.2 mM during early fed-batch cell culture and from about 2.6 mM to about 21.6 mM during late fed-batch cell culture, wherein the amount of asparagine supplemented during early fed-batch cell culture is greater than the amount of asparagine supplemented during late fed-batch cell culture, the supplementing begins on day 1 or later of the early fed-batch cell culture, and the supplementing is performed at intervals of about 2 days; and
   maintaining said cells in said asparagine supplemented cell culture medium for at least a portion of the early and late fed-batch cell culture to produce said recombinant protein of interest;
   wherein said recombinant protein of interest has reduced sequence variants compared to a recombinant protein of interest produced with a method with a lower amount of asparagine supplementation or no asparagine supplementation in early and/or late fed-batch cell culture.

2. The method of claim 1, wherein the asparagine supplement is provided as part of a bulk feed or as a separate asparagine supplement feed in early and/or late fed-batch cell culture.

3. The method of claim 1, wherein the asparagine supplement is provided continuously or as bolus in early and/or late fed-batch cell culture.

4. The method of claim 1, wherein the defined cell culture medium is supplemented with asparagine in an amount from about 7.2 mM to about 21.6 mM during early fed-batch cell culture and about 3.6 mM to about 10.8 mM during late fed-batch cell culture.

5. The method of claim 1, wherein said recombinant protein of interest is an Fc-fusion protein, a receptor-Fc-fusion protein, an antibody, an antibody fragment, or an scFv-Fc fusion protein.

6. The method of claim 1, wherein at least one additional cell culture performance parameter is improved by the asparagine supplementation, as compared to a method with a lower amount of asparagine supplementation or no asparagine supplementation in early and/or late fed batch culture, wherein the at least one additional cell culture performance parameter is selected from the group consisting of increased cell viability, increased cell growth rate, increased cell density, increased titer of the recombinant protein of interest, increased yield of the recombinant protein of interest, reduction in depletions of essential amino acids in at least a portion of the cell culture, reduction in the formation of at least one cell culture by-product in at least a portion of the cell culture, and improvement of at least one indicator of protein quality.

7. The method of claim 6, wherein the at least one cell culture by-product is selected from the group consisting of ammonium ions and alanine.

8. The method of claim 1, wherein the asparagine supplement is provided at least once, at least twice, at least three times, at least four times, at least five times, or continuously for at least a portion of the late fed-batch cell culture.

9. The method of claim 1, wherein the asparagine supplement is provided continuously beginning on day 5 or after of the fed-batch cell culture, and thereafter for at least a portion of the late fed-batch cell culture.

10. The method of claim 6, wherein the continuous asparagine supplement is discontinued on or after day 10 of the fed-batch cell culture.

11. The method of claim 1, wherein the asparagine supplement is provided continuously in early and/or late fed-batch cell culture.

12. The method of claim 1, wherein extracellular amino acid depletions in the cell culture of asparagine, aspartic acid, and glutamic acid are delayed by at least 1 day, at least 2 days, at least 3 days, or at least 4 days or more, as compared to a method with asparagine supplementation provided in early and/or late fed-batch cell culture as a bolus feed.

* * * * *